US011304456B2

(12) United States Patent
Connor

(10) Patent No.: US 11,304,456 B2
(45) Date of Patent: Apr. 19, 2022

(54) SMART BRA WITH OPTICAL SENSORS TO DETECT ABNORMAL BREAST TISSUE

(71) Applicant: Robert A. Connor, St. Paul, MN (US)

(72) Inventor: Robert A. Connor, St. Paul, MN (US)

(73) Assignee: Holovisions LLC, St. Paul, MN (US)

( * ) Notice: Subject to any disclaimer, the term of this patent is extended or adjusted under 35 U.S.C. 154(b) by 0 days.

(21) Appl. No.: 17/378,746

(22) Filed: Jul. 18, 2021

(65) Prior Publication Data

US 2021/0337885 A1   Nov. 4, 2021

Related U.S. Application Data

(63) Continuation-in-part of application No. 16/933,138, filed on Jul. 20, 2020.

(60) Provisional application No. 63/161,006, filed on Mar. 15, 2021, provisional application No. 62/879,485, filed on Jul. 28, 2019.

(51) Int. Cl.
 *A41C 3/00* (2006.01)
 *A61B 5/00* (2006.01)
 *D02G 3/44* (2006.01)

(52) U.S. Cl.
 CPC .......... *A41C 3/0064* (2013.01); *A61B 5/0075* (2013.01); *A61B 5/4312* (2013.01); *A61B 5/6802* (2013.01); *D02G 3/441* (2013.01); *D02G 3/448* (2013.01); *A61B 2562/0238* (2013.01)

(58) Field of Classification Search
 CPC ... A61B 5/0091; A61B 5/0075; A61B 5/6804; A41C 3/0064
 See application file for complete search history.

(56) References Cited

U.S. PATENT DOCUMENTS

| | | | |
|---|---|---|---|
| 5,876,339 | A | 3/1999 | Lemire |
| 5,999,836 | A | 12/1999 | Nelson et al. |
| 6,081,322 | A | 6/2000 | Barbour |
| 6,240,309 | B1 | 5/2001 | Yamashita et al. |
| 6,345,194 | B1 | 2/2002 | Nelson et al. |
| 6,571,116 | B2 | 5/2003 | Wake et al. |
| 6,640,133 | B2 | 10/2003 | Yamashita et al. |
| 6,738,658 | B2 | 5/2004 | Wake et al. |
| RE38,800 | E | 9/2005 | Barbour |
| 7,142,906 | B2 | 11/2006 | Yamashita et al. |
| 7,809,422 | B2 | 10/2010 | Corbeil et al. |
| 7,904,139 | B2 | 3/2011 | Chance |
| 8,027,711 | B2 | 9/2011 | Jones et al. |
| 8,224,426 | B2 | 7/2012 | Lilge et al. |
| 8,565,862 | B2 | 10/2013 | Intes et al. |
| 9,314,218 | B2 | 4/2016 | Stearns et al. |
| 9,495,516 | B2 | 11/2016 | Hielscher et al. |
| 9,513,276 | B2 | 12/2016 | Tearney et al. |
| 9,597,046 | B2 | 3/2017 | Goossen et al. |

(Continued)

OTHER PUBLICATIONS

Ahmed et al., 2021, "Differential Optical Absorption Spectroscopy-Based Refractive Index Sensor for Cancer Cell Detection," Optical Review, 28, 134-143.

(Continued)

*Primary Examiner* — Deborah L Malamud

(57) ABSTRACT

A smart bra to detect abnormal breast tissue with a plurality of light emitters which transmit near-infrared light into breast tissue and a plurality of light receivers which receive the light after it has passed through breast tissue, wherein changes in light intensity or spectral distribution in the light caused by passing through the breast tissue are used to identify abnormal breast tissue.

3 Claims, 23 Drawing Sheets

(56) References Cited

U.S. PATENT DOCUMENTS

| | | | |
|---|---|---|---|
| 9,724,489 B2 | 8/2017 | Barbour et al. |
| 9,770,220 B2 | 9/2017 | Stearns et al. |
| 9,993,159 B2 | 6/2018 | Islam |
| 10,111,594 B2 | 10/2018 | Hielscher et al. |
| 10,130,318 B2 | 11/2018 | Stearns et al. |
| 10,178,967 B2 | 1/2019 | Hielscher et al. |
| 10,200,655 B2 | 2/2019 | Kim et al. |
| 10,215,636 B2 | 2/2019 | Fujii et al. |
| 10,376,150 B2 | 8/2019 | Hielscher et al. |
| 10,506,181 B2 | 12/2019 | Delgado et al. |
| 10,653,346 B2 | 5/2020 | Zarandi et al. |
| 2002/0045833 A1 | 4/2002 | Wake et al. |
| 2004/0092826 A1 | 5/2004 | Corbeil et al. |
| 2005/0043596 A1 | 2/2005 | Chance |
| 2006/0058683 A1 | 3/2006 | Chance |
| 2006/0173352 A1 | 8/2006 | Lilge et al. |
| 2007/0287897 A1 | 12/2007 | Faris |
| 2009/0005692 A1 | 1/2009 | Intes et al. |
| 2010/0292569 A1 | 11/2010 | Hielscher et al. |
| 2013/0289394 A1 | 10/2013 | Hielscher et al. |
| 2013/0338496 A1 | 12/2013 | Hielscher et al. |
| 2014/0088415 A1 | 3/2014 | Hielscher et al. |
| 2014/0236003 A1 | 8/2014 | Hielscher et al. |
| 2014/0236021 A1 | 8/2014 | Islam |
| 2014/0243681 A1 | 8/2014 | Hielscher et al. |
| 2014/0330116 A1 | 11/2014 | Hielscher et al. |
| 2015/0119665 A1 | 4/2015 | Barbour et al. |
| 2015/0182121 A1 | 7/2015 | Barbour |
| 2015/0223697 A1 | 8/2015 | Hielscher et al. |
| 2015/0286785 A1 | 10/2015 | Hielscher et al. |
| 2016/0066811 A1 | 3/2016 | Mohamadi |
| 2017/0007187 A1 | 1/2017 | Breneisen et al. |
| 2017/0027480 A1 | 2/2017 | Hielscher et al. |
| 2017/0105625 A1 | 4/2017 | Eum |
| 2017/0209083 A1 | 7/2017 | Zarandi et al. |
| 2018/0070891 A1 | 3/2018 | Jepsen |
| 2018/0289264 A1 | 10/2018 | Islam |
| 2018/0335753 A1 | 11/2018 | Jepsen et al. |
| 2019/0072897 A1 | 3/2019 | Jepsen et al. |
| 2019/0239751 A1 | 8/2019 | Hielscher et al. |
| 2019/0282134 A1 | 9/2019 | Hielscher et al. |
| 2020/0116630 A1 | 4/2020 | Zhu |
| 2021/0038083 A1 | 2/2021 | Islam |

OTHER PUBLICATIONS

Altoe et al., 2019, "Diffuse Optical Tomography of the Breast: A Potential Modifiable Biomarker of Breast Cancer Risk with Neoadjuvant Chemotherapy," Biomedical Optics Express, Aug. 1, 2019, 10(8), 4305-4315.

Altoe et al., 2021, "Effects of Neoadjuvant Chemotherapy on the Contralateral Non-Tumor-Bearing Breast Assessed by Diffuse Optical Tomography," Breast Cancer Research, 2021, 23, 16.

Anderson et al., 2017, "Optical Mammography in Patients with Breast Cancer Undergoing Neoadjuvant Chemotherapy: Individual Clinical Response Index," Academic Radiology, Oct. 2017, 24(10), 1240-1255.

Angelo et al., 2018, "Review of Structured Light in Diffuse Optical Imaging," Journal of Biomedical Optics, Sep. 14, 2018, 24(7), 071602.

Applegate et al., 2018, "Multi-Distance Diffuse Optical Spectroscopy with a Single Optode via Hypotrochoidal Scanning," Optics Letters, 2018, 43, 747-750.

Chae et al., 2020, "Development of Digital Breast Tomosynthesis and Diffuse Optical Tomography Fusion Imaging for Breast Cancer Detection," Scientific Reports, 10, 13127 (2020).

Chitnis et al., 2016, "Towards a Wearable Near Infrared Spectroscopic Probe for Monitoring Concentrations of Multiple Chromophores in Biological Tissue In Vivo," Review of Scientific Instruments, Jun. 2016, 87(6), 065112.

Cochran et al., 2019, "Hybrid Time-Domain and Continuous-Wave Diffuse Optical Tomography Instrument with Concurrent, Clinical Magnetic Resonance Imaging for Breast Cancer Imaging," Journal of Biomedical Optics, Jan. 2019, 24(5), 1-11.

Durduran et al., 2010, 2010, "Diffuse Optics for Tissue Monitoring and Tomography," Reports on Progress in Physics, 2010, 73(7), 076701.

Fakayode et al., 2020, "Molecular (Raman, NIR, and FTIR) Spectroscopy and Multivariate Analysis in Consumable Products Analysis," Applied Spectroscopy Reviews, 55:8, 647-723.

Fantini et al., 2005, "Optical Spectroscopy and Imaging of Tissues," NSF Award # 0093840, Jun. 1, 2001.

Fantini et al., 2012, "Near-Infrared Optical Mammography for Breast Cancer Detection with Intrinsic Contrast," Annals of Biomedical Engineering, Feb. 2012, 40(2), 398-407.

Farmani et al., 2020, "Optical Nanosensors for Cancer and Virus Detections," Micro and Nano Technologies, Nanosensors for Smart Cities, Chapter 25, Han et al. editors, Elsevier, 2020, 419-432, ISBN 9780128198704.

Flexman et al., 2008, "The Design and Characterization of a Digital Optical Breast Cancer Imaging System," 30th Annual International Conference of the IEEE Engineering in Medicine and Biology Society, 2008, 3735-3738.

Ghijsen et al., 2018, "Quantitative Real-Time Optical Imaging of the Tissue Metabolic Rate of Oxygen Consumption," Journal of Biomedical Optics, Mar. 24, 2018, 23(3), 036013.

Grosenick et al., 2016, "Review of Optical Breast Imaging and Spectroscopy," Journal of Biomedical Optics, Sep. 2016, 21(9), 091311.

Gunther et al., 2018, "Dynamic Diffuse Optical Tomography for Monitoring Neoadjuvant Chemotherapy in Patients withBreast Cancer," Radiology, Jun. 2018; 287(3): 778-786.

Hoi et al., 2018, "Non-Contact Dynamic Diffuse Optical Tomography Imaging System for Evaluating Lower Extremity Vasculature," Biomedical Optics Express, 2018, 9, 5597-5614.

Imamura et al., 2018, "In Vivo Optical Imaging of Cancer Cell Function and Tumor Microenvironment," Cancer Science, 2018, 109, 912-918.

Intes et al., 2004, "Time-Domain Optical Mammography Softscan: Initial Results on Detection and Characterization of Breast Tumors," Proceedings SPIE 5578, Photonics North 2004: Photonic Applications in Astronomy, Biomedicine, Imaging, Materials Processing, and Education, Dec. 9, 2004.

Jeong et al., 2020, "Emerging Advanced Metasurfaces: Alternatives to Conventional Bulk Optical Devices," Microelectronic Engineering, 2020, vol. 220, 111146, ISSN 0167-9317.

Joshi et al., 2018, "Targeted Optical Imaging Agents in Cancer: Focus on Clinical Applications," Contrast Media and Molecular Imaging, Aug. 27, 2018.

Jung et al., 2015, "Non-Contact Deep Tissue Imaging using a Hand-Held Near-infrared Optical Scanner," Journal of Medical Diagnostic Methods, Mar. 24, 2015, 4(2), 1-10.

Khan, 2013, "Image Reconstruction in Diffuse Optical Tomography with Sparsity Constraints," NSF Award, 2009.

Kim et al., 2016, "US-Localized Diffuse Optical Tomography in Breast Cancer: Comparison with Pharmacokinetic Parameters of DCE-MRI and With Pathologic Biomarkers," BMC Cancer, Feb. 1, 2016, 16:50.

Koetse et al., 2007, "Optical Sensor Array Platform Based on Polymer Electronic Devices," Proceedings SPIE 6739, Electro-Optical Remote Sensing, Detection, and Photonic Technologies and Their Applications, 67391D, Nov. 7, 2007.

Koomson, 2019, "A Noninvasive Biological Research Tool for Measurement of Tissue and Cerebral Oxygenation," NSF Award # 1919038, Jul. 15, 2019.

Krishnamurthy, 2018, "Using Near-Infrared Spectroscopy to Study Static and Dynamic Hemoglobin Contrast Associated with Breast Cancer," Tufts University, Dissertation, 2018.

Leo et al., 2017, "Optical Imaging of the Breast: Basic Principles and Clinical Applications," American Journal of Roentgenology, 2017, 209:1, 230-238.

Li et al., 2018, "Sensitive and Wearable Optical Microfiber Sensor for Human Health Monitoring," Advanced Materials Technologies, 2018, 3, 1800296.

(56) References Cited

OTHER PUBLICATIONS

Liu et al., 2018, "Diffuse Optical Spectroscopy for Monitoring the Responses of Patients with Breast Cancer to Neoadjuvant Chemotherapy: A Meta-Analysis," Medicine, 2018, 97(41), 12683.
Liu et al., 2020, "Recent Progress in Flexible Wearable Sensors for Vital Sign Monitoring," Sensors, 2020, 20(14), 4009.
Liu et al., 2021, "Simultaneous Measurements of Tissue Blood Flow and Oxygenation Using a Wearable Fiber-Free Optical Sensor," Journal of Biomedical Optics, Jan. 29, 2021, 26(1), 012705.
Lutzweiler et al., 2013, "Optoacoustic Imaging and Tomography: Reconstruction Approaches and Outstanding Challenges in Image Performance and Quantification," Sensors, 2013, 13(3), 7345-7384.
Ma et al., 2020b, "Fiber-Free Parallel-Plane Continuous Wave Breast Diffuse Optical Tomography System," SPIE 11229, Advanced Biomedical and Clinical Diagnostic and Surgical Guidance Systems XVIII, Proceedings, 112290L, Feb. 21, 2020.
Mabou et al., 2018, "Breast Cancer Detection Using Infrared Thermal Imaging and a Deep Learning Model," Sensors, 2018, 18(9), 2799.
Moreno et al., 2019, "Evaluation on Phantoms of the Feasibility of a Smart Bra to Detect Breast Cancer in Young Adults," Sensors, 2019, 19(24), 5491.
Nguyen et al., 2020, "Preliminary Development of Optical Computed Tomography (Optical CT) Scanner Using Transillumination Imaging NAD," Conference: International Symposium on Applied Science 2019, Hochiminh City, Vietnam, May 14, 2020.
Pan et al., 2020, "A Multifunctional Skin-Like Wearable Optical Sensor Based on an Optical Micro-/Nanofibre," Nanoscale, 2020, Issue 33.
Park et al., 2013, "Multispectral Imaging Using Polydimethylsiloxane (PDMS) Embedded Vertical Silicon Nanowires," OSA Technical Digest (online) (Optical Society of America, 2013), paper CTu3O.1.
Park et al., 2015, "Vertically Stacked Photodetector Devices Containing Silicon Nanowires with Engineered Absorption Spectra," ACS Photonics, Mar. 16, 2015, 2(4), 544-549.
Perumal et al., 2019, "Near Infra-Red Polymeric Nanoparticle Based Optical Imaging in Cancer Diagnosis," Journal of Photochemistry and Photobiology, Biology, 2019, vol. 199, 111630, ISSN 1011-1344.
Pinti et al., 2018, "A Review on the Use of Wearable Functional Near-Infrared Spectroscopy in Naturalistic Environments," Japanese Psychology Research, Oct. 2018, 60(4), 347-373.
Qiu, 2018, "Implantable Ultra-Low Power VO2 MEMS Scanner Based Surface-Enhanced Raman Spectroscope for Wide-Field Tumor Imaging in Free Moving Small Animals," NSF Award, 2018.
Rahman et al., 2016, "Electromagnetic Performances Analysis of an Ultra-Wideband and Flexible Material Antenna in Microwave Breast Imaging: To Implement a Wearable Medical Bra," Scientific Reports, 2016, vol. 6, 38906.
Ray et al., 2017, "A Systematic Review of Wearable Systems for Cancer Detection: Current State and Challenges," Journal of Medical Systems, Oct. 2, 2017, 41(11), 180.
Robbins et al., 2021, "Two-Layer Spatial Frequency Domain Imaging of Compression-Induced Hemodynamic Changes in Breast Tissue," Journal of Biomedical Optics, May 24, 2021, 26(5), 056005.
Roblyer et al., 2020b, "Tracking Breast Cancer Therapies with Handheld and Wearable Diffuse Optics," Biophotonics Congress: Biomedical Optics 2020 (Translational, Microscopy, OCT, OTS, BRAIN), OSA Technical Digest (Optical Society of America, 2020), paper TM4B.1.
Shokoufi et al., 2017, "Novel Handheld Diffuse Optical Spectroscopy Probe for Breast Cancer Assessment: Clinical Study," Journal of Biomedical Science, 6(5), 34.
Soliman et al., 2010, "Functional Imaging Using Diffuse Optical Spectroscopy of Neoadjuvant Chemotherapy Response in Women with Locally Advanced Breast Cancer," Clinical Cancer Research, Apr. 20, 2010, 15, 2605-2614.
Spink et al., 2020, "High Optode-Density Wearable Probe for Monitoring Breast Tumor Dynamics During Neoadjuvant Chemotherapy," Biophotonics Congress: Biomedical Optics 2020 (Translational, Microscopy, OCT, OTS, BRAIN). OSA Technical Digest, paper TTu1B.2.
Spink et al., 2021, "High Optode-Density Wearable Diffuse Optical Probe for Monitoring Paced Breathing Hemodynamics in Breast Tissue," Journal of Biomedical Optics, Jun. 2, 2021, 26(6), 062708.
Tank et al., 2020, "Diffuse Optical Spectroscopic Imaging Reveals Distinct Early Breast Tumor Hemodynamic Responses to Metronomic and Maximum Tolerated Dose Regimens," Breast Cancer Research, 2020, 22, 29.
Teng et al., 2017, "Wearable Near-Infrared Optical Probe for Continuous Monitoring During Breast Cancer Neoadjuvant Chemotherapy Infusions," Journal of Biomedical Optics, 22(1), 14001.
Teng, 2018, "A Wearable Near-Infrared Diffuse Optical System for Monitoring in Vivo Breast Tumor Hemodynamics During Chemotherapy Infusions," Boston University, Dissertation, 2018.
Tromberg et al., 2016, "ACRIN 6691 Investigators. Predicting Responses to Neoadjuvant Chemotherapy in Breast Cancer," Cancer Research, Aug. 15, 2016, 76(20), 5933-5944.
Uddin et al., 2020a, "Optimal Breast Cancer Diagnostic Strategy Using Combined Ultrasound and Diffuse Optical Tomography," Biomedical Optics Express, 11(5), 2722-2737.
Upputuri, 2019, "Photoacoustic Imaging in the Second Near-Infrared Window: A Review," Journal of Biomedical Optics, Apr. 9, 2019, 24(4), 040901.
Vavadi et al., 2018, "Compact Ultrasound-Guided Diffuse Optical Tomography System for Breast Cancer Imaging," Journal of Biomedical Optics, 2018, 24(2), 1-9.
Wang et al., 2020, "Development of a Prototype of a Wearable Flexible Electro-Optical Imaging System for the Breast," Biophotonics Congress: Biomedical Optics 2020 (Translational, Microscopy, OCT, OTS, BRAIN), OSA Technical Digest, paper TM4B.4.
Yu et al., 2010, "Near-Infrared, Broad-Band Spectral Imaging of the Human Breast for Quantitative Oximetry: Applications to Healthy and Cancerous Breasts," Journal of Innovative Optical Health Sciences, Oct. 2010, 03(4):267-277.
Yuan et al., 2014, "Light-Emitting Diode-Based Multiwavelength Diffuse Optical Tomography System Guided by Ultrasound," Journal of Biomedical Optics, Dec. 4, 2014, 19(12) 126003.
Zhang et al., 2020, "Efficacy of Shear-Wave Elastography Versus Dynamic Optical Breast Imaging for Predicting the Pathological Response to Neoadjuvant Chemotherapy in Breast Cancer," European Journal of Radiology, 2020, 129, 109098.
Zhu et al., 2020, "A Review of Optical Breast Imaging: Multi-Modality Systems for Breast Cancer Diagnosis," European Journal of Radiology, Aug. 2020, 129:109067.
Zhu et al., 2021, "Early Assessment Window for Predicting Breast Cancer Neoadjuvant Therapy Using Biomarkers, Ultrasound, and Diffuse Optical Tomography," Breast Cancer Research and Treatment, 2021.

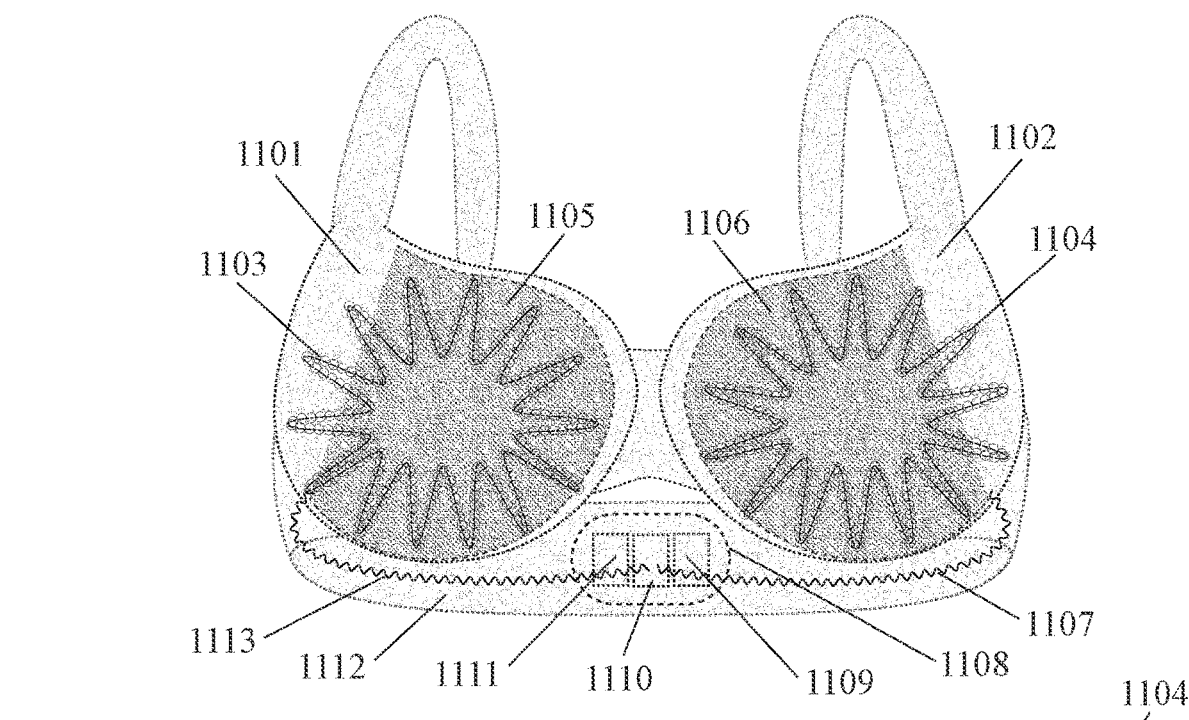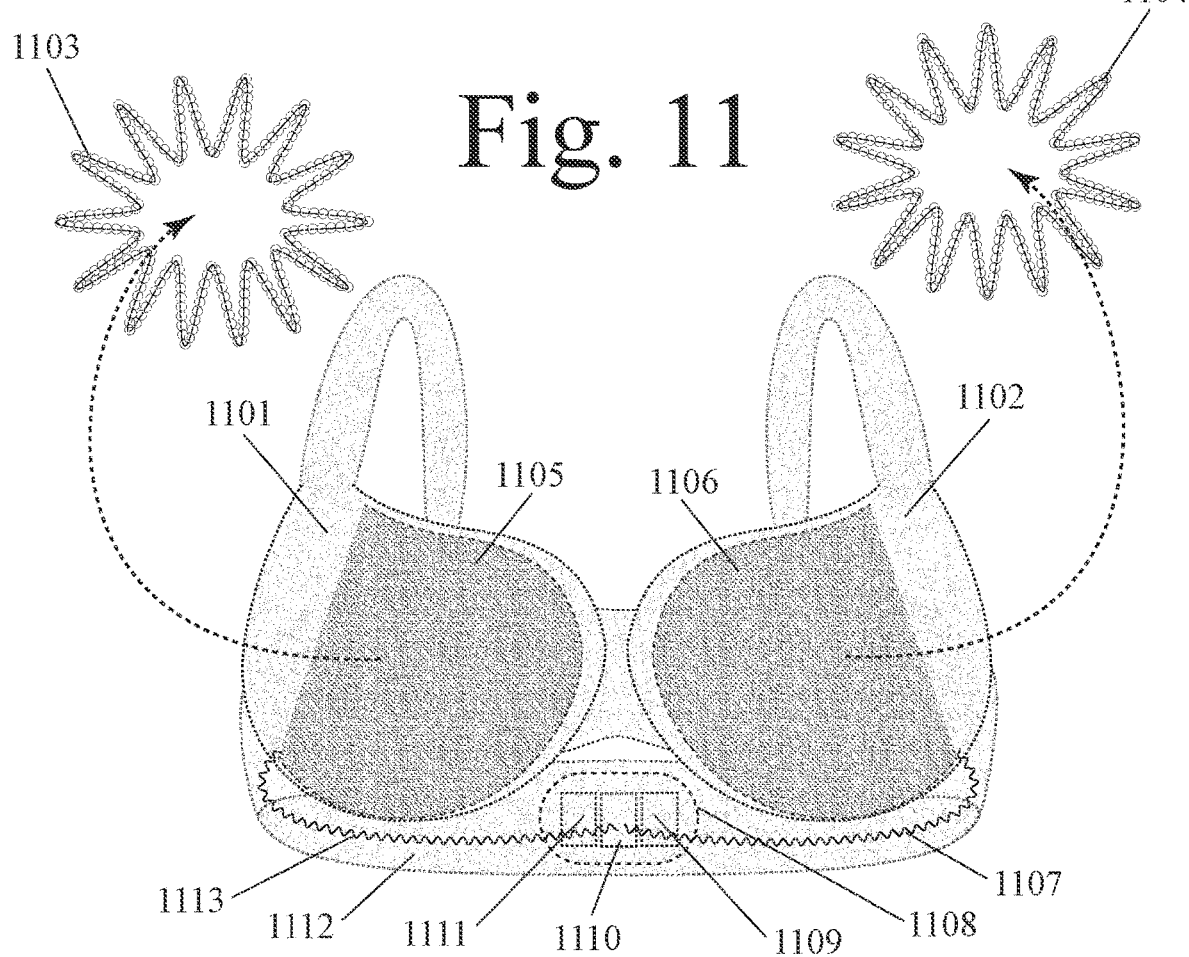
Fig. 11

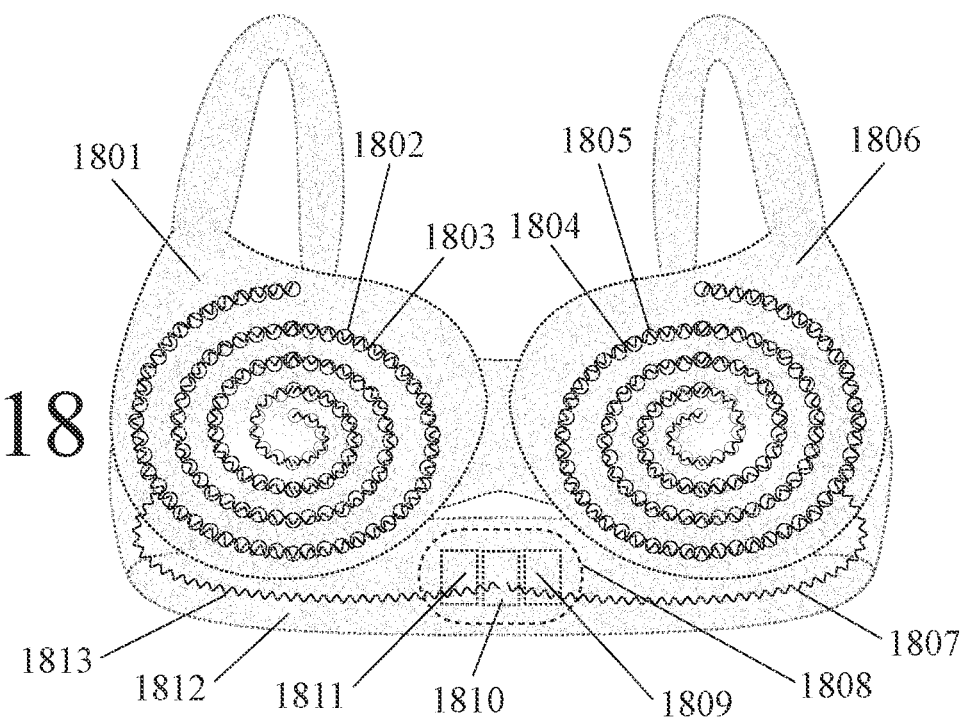
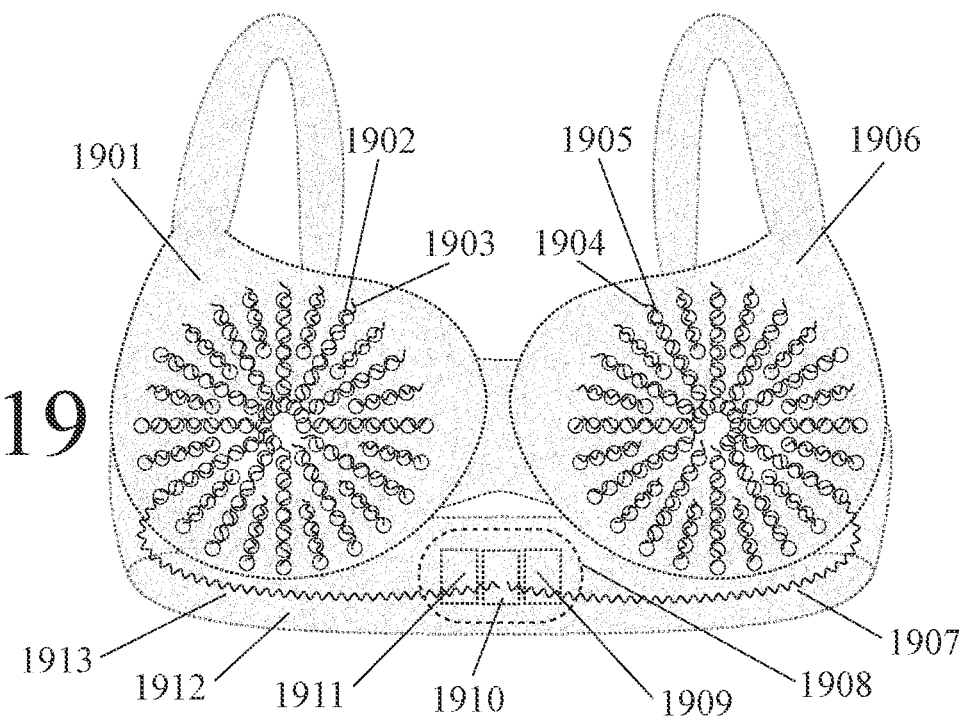

SMART BRA WITH OPTICAL SENSORS TO DETECT ABNORMAL BREAST TISSUE

CROSS-REFERENCE TO RELATED APPLICATIONS

This application claims the priority benefit of U.S. provisional application 63/161,006 filed on 2021 Mar. 15. This application is a continuation-in-part of U.S. application Ser. No. 16/933,138 filed on 2020 Jul. 20 which, in turn, claimed the priority benefit of U.S. provisional application 62/879,485 filed on 2019 Jul. 28. The entire contents of these related applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable medical devices for imaging and diagnosis.

INTRODUCTION

Breast cancer is the most common form of cancer in women and a leading cause of death. Breast imaging can serve a critical role in the early diagnosis and treatment of breast cancer. However, there are limitations to frequent use of the current breast imaging modalities. Current modalities of breast imaging and/or abnormal tissue detection include: x-ray mammography (most common), Magnetic Resonance Imaging (MRI), and ultrasonography. Limitations of x-ray mammography include exposure to ionizing radiation, lower accuracy for younger individuals and those with dense breast tissue, uncomfortable compression of the breast, relatively high false positive rate, and two-dimensional images. Limitations of Magnetic Resonance Imaging (MRI) include relatively low specificity, long exam times, and high cost. Limitations of ultrasound imaging include difficulty visualizing microcalcifications and strong dependence on examiner interpretation. General limitations of current modalities include required access to specialized facilities, examination time required, embarrassment and/or cultural barriers. There remains a need for a new breast imaging modality which can be used frequently and safely for breast imaging and tissue analysis.

During recent years, there has been increased investigation of the possibilities of optical breast imaging using safe non-ionizing radiation such as visible, ultraviolet, infrared, and near-infrared light energy. However, thus far there have been limitations to optical breast imaging. For example, with current stationary optical imaging devices, it can be difficult to get close optical communication between the breast and the light emitters and receivers of the device due to differences in the sizes and shapes of breasts. With current handheld optical imaging devices, it can be difficult to accurately measure absolute tissue locations to track changes over time and to get a comprehensive image of the complete breast.

REVIEW OF THE RELEVANT ART

In the patent literature, U.S. patent application 20050043596 (Chance, Feb. 24, 2005, "Optical Examination Device, System and Method") discloses a brush-form optical coupler with freely extending fiber end portions, sized and positioned to make optical contact with a subject, examination, and monitoring systems utilizing one or more of such couplers. U.S. patent application 20060058683 (Chance, Mar. 16, 2006, "Optical Examination of Biological Tissue Using Non-Contact Irradiation and Detection") and U.S. Pat. No. 7,904,139 (Chance, Mar. 8, 2011, "Optical Examination of Biological Tissue Using Non-Contact Irradiation and Detection") disclose an optical system for examination of biological tissue which includes a light source, a light detector, optics and electronics.

U.S. Pat. No. 6,081,322 (Barbour, Jun. 27, 2000, "NIR Clinical Opti-Scan System") and RE38800 (Barbour, Sep. 20, 2005, "NIR Clinical Opti-Scan System") disclose three-dimensional optical imaging techniques for the detection and three-dimensional imaging of absorbing and/or scattering structures in complex random media, such as human body tissue, by detecting scattered light. U.S. patent application 20150182121 (Barbour, Jul. 2, 2015, "Low-Cost Screening System for Breast Cancer Detection") discloses a portable and wearable tumor detector including a brassier and devices for optical tomography. U.S. patent application publication 20150119665 (Barbour et al., Apr. 30, 2015, "Self-Referencing Optical Measurement for Breast Cancer Detection") and U.S. Pat. No. 9,724,489 (Barbour et al., Aug. 8, 2017, "Self-Referencing Optical Measurement for Breast Cancer Detection") disclose obtaining optical data from a pair of breasts, employing a simultaneous bilateral referencing protocol, and employing a self-referencing data analysis method.

U.S. patent applications 20100292569 (Hielscher et al., Nov. 18, 2010, "Systems and Methods for Dynamic Imaging of Tissue Using Digital Optical Tomography") and 20150223697 (Hielscher et al., Aug. 13, 2015, "Systems and Methods for Dynamic Imaging of Tissue Using Digital Optical Tomography") disclose methods for imaging tissue using diffuse optical tomography including directing a amplitude modulated optical signals from optical signal sources. U.S. patent application 20140330116 (Hielscher et al., Nov. 6, 2014, "Systems and Methods for Simultaneous Multi-Directional Imaging for Capturing Tomographic Data") discloses devices, systems, and method for tomographic imaging in which light transmitted and backscattered surface light is imaged by an optical system that minimizes reflection back to the target object. U.S. patent applications 20130289394 (Hielscher et al., Oct. 31, 2013, "Dynamic Optical Tomographic Imaging Devices Methods and Systems"), 20170027480 (Hielscher et al., Feb. 2, 2017, "Dynamic Optical Tomographic Imaging Devices Methods and Systems"), and 20190282134 (Hielscher et al., Sep. 19, 2019, "Dynamic Optical Tomographic Imaging Devices Methods and Systems"), and U.S. patent Ser. No. 10/178,967 (Hielscher et al., Jan. 15, 2019, "Dynamic Optical Tomographic Imaging Devices Methods and Systems") disclose an optical tomographic systems for acquiring and displaying dynamic data representing changes in a target tissue sample to external provocation. U.S. patent applications 20130338496 (Hielscher et al., Dec. 19, 2013, "Medical Imaging Devices, Methods, and Systems") and 20140088415 (Hielscher et al., Mar. 27, 2014, "Medical Imaging Devices, Methods, and Systems") disclose devices, methods, and systems for generating optical tomographic data including volumetric and surface geometric data.

U.S. patent application publication 20140236003 (Hielscher et al., Aug. 21, 2014, "Interfacing Systems, Devices, and Methods for Optical Imaging") discloses an imaging interface with a plurality of concentric rings for diffuse optical tomography of breast tissue. U.S. patent applications 20140243681 (Hielscher et al., Aug. 28, 2014, "Compact Optical Imaging Devices, Systems, and Methods") and 20190239751 (Hielscher et al., Aug. 8, 2019, "Compact Optical Imaging Devices, Systems, and Methods"), and U.S. patent Ser. No. 10/111,594 (Hielscher et al., Oct. 30, 2018, "Compact Optical Imaging Devices, Systems, and Methods") disclose a handheld optical imaging system with a plurality of detectors. U.S. patent application 20150286785 (Hielscher et al., Oct. 8, 2015, "Systems, Methods, and Devices for Image Reconstruction Using Combined PDE-Constrained and Simplified Spherical Harmonics Algorithm") and U.S. Pat. No. 9,495,516 (Hielscher et al., Nov. 15, 2016, "Systems, Methods, and Devices for Image Reconstruction Using Combined PDE-Constrained and Simplified Spherical Harmonics Algorithm") disclose systems, methods, and devices for image reconstruction using combined PDE-constrained and simplified spherical harmonics (SPN) algorithms. U.S. patent Ser. No. 10/376,150 (Hielscher et al., Aug. 13, 2019, "Interfacing Systems, Devices, and Methods for Optical Imaging") discloses an imaging interface for diffuse optical tomography of breast with a plurality of concentric rings.

U.S. patent application publication 20140236021 (Islam, Aug. 21, 2014, "Near-Infrared Super-Continuum Lasers for Early Detection of Breast and Other Cancers") and U.S. Pat. No. 9,993,159 (Islam, Jun. 12, 2018, "Near-Infrared Super-Continuum Lasers for Early Detection of Breast and Other Cancers") disclose a system and method using near-infrared or short-wave infrared light sources for early detection and monitoring of breast cancer. U.S. patent application publication 20180289264 (Islam, Oct. 11, 2018, "High Signal-to-Noise Ratio Light Spectroscopy of Tissue") discloses a diagnostic system which delivers an optical beam to a nonlinear element that broadens a spectrum of the first optical beam to at least 10 nanometers through a nonlinear effect in the nonlinear element. U.S. patent application 20210038083 (Islam, Feb. 11, 2021, "Multi-Wavelength Wearable Device for Non-Invasive Blood Measurements in Tissue") discloses a system for measuring one or more physiological parameters with a wearable device that includes a light source comprising a driver and semiconductor sources that generate an output optical light.

U.S. patent application publication 20090005692 (Intes et al., Jan. 1, 2009, "Optical Imaging Method for Tissue Characterization") and U.S. Pat. No. 8,565,862 (Intes et al., Oct. 22, 2013, "Optical Imaging Method for Tissue Characterization") disclose a method for detecting and characterizing abnormalities within biological tissue by characterizing optical properties of the tissue. U.S. patent application publication 20180070891 (Jepsen, Mar. 15, 2018, "Imaging With Infrared Imaging Signals") discloses using an infrared imaging signal to image tissue. U.S. patent application publication 20180335753 (Jepsen et al., Nov. 22, 2018, "Co-Located Imaging and Display Pixel") discloses an optical transformation engine coupled between an image pixel and a display pixel. U.S. patent application publication 20190072897 (Jepsen et al., Mar. 7, 2019, "Applications of Diffuse Medium Imaging") discloses methods and an apparatus for imaging translucent materials.

U.S. Pat. No. 9,314,218 (Stearns et al., Apr. 19, 2016, "Integrated Microtomography and Optical Imaging Systems") and Ser. No. 10/130,318 (Stearns et al., Nov. 20, 2018, "Integrated Microtomography and Optical Imaging Systems") disclose an integrated microtomography and optical imaging system with a rotating table that supports an imaging object, an optical stage, and separate optical and microtomography imaging systems. U.S. Pat. No. 9,770,220 (Stearns et al., Sep. 26, 2017, "Integrated Microtomography and Optical Imaging Systems") discloses a rotating table that supports an imaging object, an optical stage, and separate optical and microtomography imaging systems. U.S. patent application 20170209083 (Zarandi et al., 2017, "Hand-Held Optical Scanner for Real-Time Imaging of Body Composition and Metabolism") and U.S. patent Ser. No. 10/653,346 (Zarandi et al., May 19, 2020, "Hand-Held Optical Scanner for Real-Time Imaging of Body Composition and Metabolism") disclose a handheld system for diffuse optical spectroscopic imaging of human tissue.

U.S. patent application 20060173352 (Lilge et al., 2006, "Optical Transillumination and Reflectance Spectroscopy to Quantify Disease Risk") discloses a method of illuminating tissue of a mammal with light having wavelengths covering a pre-selected spectral range, detecting light transmitted through, or reflected from, the volume of selected tissue, and obtaining a spectrum of the detected light. U.S. patent application 20200116630 (Zhu, 2020, "Compact Guided Diffuse Optical Tomography System for Imaging a Lesion Region") discloses a compact diffuse optical tomography system with laser diodes and a laser diode driver board. U.S. Pat. No. 5,876,339 (Lemire, Mar. 2, 1999, "Apparatus for Optical Breast Imaging") discloses an optical breast imager with an adjustable volume which encloses a patient's breast.

U.S. Pat. No. 5,999,836 (Nelson et al., Dec. 7, 1999, "Enhanced High Resolution Breast Imaging Device and Method Utilizing Non-Ionizing Radiation of Narrow Spectral Bandwidth") and U.S. Pat. No. 6,345,194 (Nelson et al., Feb. 5, 2002, "Enhanced High Resolution Breast Imaging Device and Method Utilizing Non-Ionizing Radiation of Narrow Spectral Bandwidth") disclose breast imaging using collimated non-ionizing radiation in the near ultraviolet, visible, infrared, and microwave regions. U.S. Pat. No. 6,240,309 (Yamashita et al., May 29, 2001, "Optical Measurement Instrument for Living Body"), U.S. Pat. No. 6,640,133 (Yamashita et al., Oct. 28, 2003, "Optical Measurement Instrument for Living Body"), and U.S. Pat. No. 7,142,906 (Yamashita et al., Nov. 28, 2006, "Optical Measurement Instrument for Living Body") disclose an optical measurement instrument which applies visible-infrared light to several positions on a patient.

U.S. patent application 20020045833 (Wake et al., Apr. 18, 2002, "Medical Optical Imaging Scanner Using Multiple Wavelength Simultaneous Data Acquisition for Breast Imaging") discloses a scanner for a medical optical imaging device with an illumination source which directs emitted light into a breast positioned below a support surface. U.S. Pat. No. 6,571,116 (Wake et al., May 27, 2003, "Medical Optical Imaging Scanner Using Multiple Wavelength Simultaneous Data Acquisition for Breast Imaging") and U.S. Pat. No. 6,738,658 (Wake et al., May 18, 2004, "Medical Optical Imaging Scanner Using Multiple Wavelength Simultaneous Data Acquisition for Breast Imaging") disclose a medical optical imaging device with an illumination source that directs emitted light into a breast positioned below a support surface.

U.S. patent application publication 20040092826 (Corbeil et al., May 13, 2004, "Method and Apparatus for Optical Imaging") and U.S. Pat. No. 7,809,422 (Corbeil et al., Oct. 5, 2010, "Method and Apparatus for Optical Imaging") disclose a platform with a cavity into which one of the person's breasts is suspended for optical imaging. U.S. patent application publication 20070287897 (Faris, Dec. 13, 2007, "Optical Vascular Function Imaging System and Method for Detection and Diagnosis of Cancerous Tumors") discloses an in-vivo optical imaging system and method of identifying unusual vasculature associated with tumors. U.S. Pat. No. 8,027,711 (Jones et al., Sep. 27, 2011, "Laser Imaging Apparatus with Variable Patient Positioning") discloses a tabletop to support a patient in front-down position and an opening to permit a breast of the patient to be vertically pendant below the tabletop.

U.S. Pat. No. 8,224,426 (Lilge et al., Jul. 17, 2012, "Optical Transillumination and Reflectance Spectroscopy to Quantify Disease Risk") discloses spectroscopic tissue volume measurements with non-ionizing radiation to detect pre-disease transformations in tissue. U.S. patent application publication 20160066811 (Mohamadi, Mar. 10, 2016, "Handheld and Portable Scanners for Millimeter Wave Mammography and Instant Mammography Imaging") discloses an array of ultra-wide band radio frequency sensors for breast imaging. U.S. Pat. No. 9,513,276 (Tearney et al., Dec. 6, 2016, "Method and Apparatus for Optical Imaging via Spectral Encoding") disclose a method, apparatus and arrangement for obtaining information associated with a sample such as a portion of an anatomical structure. U.S. patent application publication 20170007187 (Breneisen et al., Jan. 12, 2017, "Cancer Detector Using Deep Optical Scanning") discloses Deep Optical Scanning (DEOS) for the detection of breast cancer and the determination of response to therapy.

U.S. Pat. No. 9,597,046 (Goossen et al., Mar. 21, 2017, "Method and Device for Imaging Soft Body Tissue Using X-Ray Projection and Optical Tomography") discloses breast imaging using X-ray projection techniques and optical tomography techniques. U.S. patent application 20170105625 (Eum, Apr. 20, 2017, "Diagnostic Device of Optics Type for Breast") discloses an optical breast diagnostic apparatus with a hemispherical cover. U.S. patent Ser. No. 10/200,655 (Kim et al., Feb. 5, 2019, "Tomographic Imaging Methods, Devices, and Systems") discloses a multispectral bioluminescence optical tomography algorithm makes use of a partial differential equation (PDE) constrained approach. U.S. patent Ser. No. 10/215,636 (Fujii et al., Feb. 26, 2019, "Imaging Device Provided With Light Source That Emits Pulsed Light and Image Sensor") discloses an imaging device with a light source that emits pulsed light at different wavelengths. U.S. patent Ser. No. 10/506,181 (Delgado et al., Dec. 10, 2019, "Device for Optical Imaging") discloses the capture of an infrared image.

Turning now to non-patent literature, Chitnis et al., (2016), "Towards a Wearable Near Infrared Spectroscopic Probe for Monitoring Concentrations of Multiple Chromophores in Biological Tissue In Vivo" discloses a wearable multi-wavelength technology for functional near-infrared spectroscopy with an 8-wavelength light emitting diode (LED) source. Jung et al., (2015), "Non-Contact Deep Tissue Imaging using a Hand-Held Near-infrared Optical Scanner" discloses fiber-free non-contact near-infrared (NIR) imaging devices using wide-field detectors.

Koomson (2019), "PFI-TT: A Noninvasive Biological Research Tool for Measurement of Tissue and Cerebral Oxygenation," NSF Award, 2019 (abstract only viewed) investigates compact wearable devices with advanced NIRS capability. Liu et al., (2021), "Simultaneous Measurements of Tissue Blood Flow and Oxygenation Using a Wearable Fiber-Free Optical Sensor" discusses a wearable dual-wavelength diffuse speckle contrast flow oximetry (DSCFO) device for simultaneous measurements of blood flow and oxygenation variation in deep tissues. Moreno et al. (2019), "Evaluation on Phantoms of the Feasibility of a Smart Bra to Detect Breast Cancer in Young Adults", discloses the use of breast tissue phantoms to investigate the feasibility of quantifying breast density and detecting breast cancer tumors using a smart bra.

Pinti et al., (2018), "A Review on the Use of Wearable Functional Near-Infrared Spectroscopy in Naturalistic Environments" reviews the use of wearable fNIRS in naturalistic settings in the field of cognitive neuroscience. Rahman et al., (2016), "Electromagnetic Performances Analysis of an Ultra-Wideband and Flexible Material Antenna in Microwave Breast Imaging: To Implement a Wearable Medical Bra" discloses a compact and ultra-wide band antenna on a flexible substrate for microwave imaging. Ray et al. (2017), "A Systematic Review of Wearable Systems for Cancer Detection: Current State and Challenges" reviews cancer detection using wearable systems, including sensor-based smart systems with a microcontroller, Bluetooth module, and smart phone.

Robbins et al., (2021), "Two-Layer Spatial Frequency Domain Imaging of Compression-Induced Hemodynamic Changes in Breast Tissue" studied hemodynamic changes in response to localized breast compression using a handheld SFDI device. Roblyer et al., (2020b), "Tracking Breast Cancer Therapies with Handheld and Wearable Diffuse Optics" disclose an NIR-II imaging system, "Detection of Optically Luminescent Probes using Hyperspectral and Diffuse Imaging in Near-infrared" (DOLPHIN) for noninvasive real-time tracking of a 0.1 mm-sized fluorophore through the gastrointestinal tract of a mouse. Shokoufi et al. (2017), "Novel Handheld Diffuse Optical Spectroscopy Probe for Breast Cancer Assessment: Clinical Study", discloses a hand-held continuous-wave radio-frequency modulated diffuse optical spectroscopy probe.

Spink et al., (2020), "High Optode-Density Wearable Probe for Monitoring Breast Tumor Dynamics During Neoadjuvant Chemotherapy" disclose an NIR-II imaging system, "Detection of Optically Luminescent Probes using Hyperspectral and diffuse Imaging in Near-infrared" (DOLPHIN). Spink et al., (2021), "High Optode-Density Wearable Diffuse Optical Probe for Monitoring Paced Breathing Hemodynamics in Breast Tissue" discloses a high optodedensity wearable continuous wave diffuse optical probe for the monitoring of breathing hemodynamics in breast tissue.

Teng et al., (2017), "Wearable Near-Infrared Optical Probe for Continuous Monitoring During Breast Cancer Neoadjuvant Chemotherapy Infusions" presents a new continuous-wave wearable diffuse optical probe for investigating the hemodynamic response of locally advanced breast cancer patients during neoadjuvant chemotherapy infusions. Teng, (2018), "A Wearable Near-Infrared Diffuse Optical System for Monitoring in Vivo Breast Tumor Hemodynamics During Chemotherapy Infusions" discloses a new wearable diffuse optical device to investigate if very early time-points during a patient's first chemotherapy infusion are predictive of overall response (pCR versus non-pCR) to NAC. Wang et al., (2020), "Development of a Prototype of a Wearable Flexible Electro-Optical Imaging System for the Breast" discloses a wearable breast imaging system which combines a garment and a flexible electronic system.

Ahmed et al., (2021), "Differential Optical Absorption Spectroscopy-Based Refractive Index Sensor for Cancer Cell Detection" discloses a spectroscopic optical sensor for cancerous cell detection in various parts of the human body. Altoe et al., (2019), "Diffuse Optical Tomography of the Breast: A Potential Modifiable Biomarker of Breast Cancer Risk with Neoadjuvant Chemotherapy" studied whether a diffuse optical tomography breast imaging system (DOTBIS) can provide a comparable optical-based image index of mammographic breast density. Altoe et al., (2021), "Changes in Diffuse Optical Tomography Images During Early Stages of Neoadjuvant Chemotherapy Correlate with Tumor Response in Different Breast Cancer Subtypes" studied changes in optically derived parameters acquired with a diffuse optical tomography breast imaging system (DOTBIS) in the tumor volume of patients with breast carcinoma receiving neoadjuvant chemotherapy (NAC). Altoe et al., (2021), "Effects of Neoadjuvant Chemotherapy on the Contralateral Non-Tumor-Bearing Breast Assessed by Diffuse Optical Tomography" studied whether changes in optically derived parameters acquired with a diffuse optical tomography breast imager system (DOTBIS) in the contralateral non-tumor-bearing breast in patients administered neoadjuvant chemotherapy (NAC) for breast cancer are associated with pathologic complete response (pCR).

Anderson et al., (2017), "Optical Mammography in Patients with Breast Cancer Undergoing Neoadjuvant Chemotherapy: Individual Clinical Response Index" discloses an optical mammography study to develop quantitative measures of pathologic response to neoadjuvant chemotherapy (NAC) in patients with breast cancer. Angelo et al., (2018), "Review of Structured Light in Diffuse Optical Imaging" discloses diffuse optical imaging probes in living tissue enabling structural, functional, metabolic, and molecular imaging. Applegate et al., (2018), "Multi-Distance Diffuse Optical Spectroscopy with a Single Optode via Hypotrochoidal Scanning" studied a new method of frequency-domain diffuse optical spectroscopy (FD-DOS) to rapidly acquire a wide range of source-detector (SD) separations by mechanically scanning a single SD pair.

Chae et al., (2020), "Development of Digital Breast Tomosynthesis and Diffuse Optical Tomography Fusion Imaging for Breast Cancer Detection" studied a new digital breast tomosynthesis (DBT)/DOT fusion imaging technique for breast cancer detection. Cochran et al., (2019), "Hybrid Time-Domain and Continuous-Wave Diffuse Optical Tomography Instrument with Concurrent, Clinical Magnetic Resonance Imaging for Breast Cancer Imaging" discusses diffuse optical tomography (DOT) for three-dimensional (3-D) maps of tissue optical and physiological properties in human tissue. Durduran et al. (2010), "Diffuse Optics for Tissue Monitoring and Tomography" discloses using near-infrared or diffuse optical spectroscopy to measure tissue hemodynamics.

Fakayode et al., (2020), "Molecular (Raman, NIR, and FTIR) Spectroscopy and Multivariate Analysis in Consumable Products Analysis" reviews the use of Raman, near-infrared (NIR), and Fourier-transform infrared (FTIR) spectrometers to evaluate consumable products such as food. Fantini et al., (2001), "Optical Spectroscopy and Imaging of Tissues" studies development of new improved methods and instrumentation for biomedical applications of near-infrared spectroscopy and imaging. Fantini (2005), "Optical Spectroscopy and Imaging of Tissues", NSF Award, 2005 (abstract only viewed), researched techniques for optical spectroscopy and imaging of biological tissues. Fantini et al., (2012), "Near-Infrared Optical Mammography for Breast Cancer Detection with Intrinsic Contrast" reviews optical methods to detect breast cancer on the basis of increased opacity. Farmani et al., (2020), "Optical Nanosensors for Cancer and Virus Detections" discusses photonic crystal (PhC)-based optical nanosensors.

Flexman et al., (2008), "The Design and Characterization of a Digital Optical Breast Cancer Imaging System" discusses how optical imaging has the potential to play a major role in breast cancer screening and diagnosis due to its ability to image cancer characteristics such as angiogenesis and hypoxia. Ghijsen et al., (2018), "Quantitative Real-Time Optical Imaging of the Tissue Metabolic Rate of Oxygen Consumption" discloses a noncontact method for quantitatively mapping tMRO2 over a wide, scalable field of view. Grosenick et al. (2016), "Review of Optical Breast Imaging and Spectroscopy reviews the monitoring neoadjuvant chemotherapy and breast cancer risk assessment via optical breast imaging and spectroscopy. Gunther et al. (2018), "Dynamic Diffuse Optical Tomography for Monitoring Neoadjuvant Chemotherapy in Patients with Breast Cancer" identifies dynamic optical imaging features associated with pathologic response in patients with breast cancer during neoadjuvant chemotherapy.

Hoi et al., (2018), "Non-Contact Dynamic Diffuse Optical Tomography Imaging System for Evaluating Lower Extremity Vasculature" discloses a multi-view non-contact dynamic diffuse optical tomographic imaging system for the clinical evaluation of vasculature in the lower extremities. Imamura et al., (2018), "In Vivo Optical Imaging of Cancer Cell Function and Tumor Microenvironment" discusses in vivo optical imaging using fluorescence and bioluminescence. Intes et al., (2004), "Time-Domain Optical Mammography Softscan: Initial Results on Detection and Characterization of Breast Tumors" presents initial results obtained using a breast-imaging system developed by Advanced Research Technologies comprising a 4-wavelength time-resolved scanning system. Jeong et al., (2020), "Emerging Advanced Metasurfaces: Alternatives to Conventional Bulk Optical Devices" discusses the use of optical metasurfaces as color filters, metalenses, beam generators or splitters, and metaholograms.

Joshi et al., (2018), "Targeted Optical Imaging Agents in Cancer: Focus on Clinical Applications" discusses molecular imaging for in vivo visualization of cancer over time based on biological mechanisms of disease activity Khan (2013), "Image Reconstruction in Diffuse Optical Tomography With Sparsity Constraints", NSF Award, 2013 (abstract only viewed), researched the use of sparsity-constrained regularization for solving the diffuse optical tomography inverse problem. Kim et al. (2016), "US-Localized Diffuse Optical Tomography in Breast Cancer: Comparison With Pharmacokinetic Parameters of DCE-MRI and With Pathologic Biomarkers" discloses correlating parameters of ultrasonography-guided diffuse optical tomography with the pharmacokinetic features of dynamic contrast-enhanced MRI and pathologic markers of breast cancer. Koetse et al., (2007), "Optical Sensor Array Platform Based on Polymer Electronic Devices" discusses devices based on polymer semiconductors fabricated with thin film technology.

Krishnamurthy, (2018), "Using Near-Infrared Spectroscopy to Study Static and Dynamic Hemoglobin Contrast Associated with Breast Cancer" discloses an instrument for diffuse optical mammography with parallel plate geometry. Leo et al., (2017), "Optical Imaging of the Breast: Basic Principles and Clinical Applications" summarizes the physical principles, technology features, and first clinical applications of optical imaging techniques to the breast. Li et al., (2018), "Sensitive and Wearable Optical Microfiber Sensor for Human Health Monitoring" discloses a sensor with a hybrid plasmonic microfiber knot resonator embedded in a polydimethylsiloxane membrane.

Liu et al., (2018), "Diffuse Optical Spectroscopy for Monitoring the Responses of Patients with Breast Cancer to Neoadjuvant Chemotherapy: A Meta-Analysis" investigated the potential of diffuse optical spectroscopy (DOT) for monitoring the responses of patients with breast cancer to neoadjuvant chemotherapy (NAC). Liu et al., (2020), "Recent Progress in Flexible Wearable Sensors for Vital Sign Monitoring" discusses the development of flexible electronic materials, as well as the wide development and application of smartphones, the cloud, and wireless systems, flexible wearable sensor technology. Lutzweiler et al. (2013), "Optoacoustic Imaging and Tomography: Reconstruction Approaches and Outstanding Challenges in Image Performance and Quantification" reviews optoacoustic imaging from image reconstruction and quantification perspectives. Ma et al., (2020b), "Fiber-Free Parallel-Plane Continuous Wave Breast Diffuse Optical Tomography System" discusses near infrared diffuse optical tomography (DOT) for detecting breast cancer.

Mabou et al. (2018), "Breast Cancer Detection Using Infrared Thermal Imaging and a Deep Learning Model" discloses the use of infrared digital imaging for breast cancer detection based on thermal comparison between a healthy breast and a breast with cancer. Nguyen et al., (2020), "Preliminary Development of Optical Computed Tomography (Optical CT) Scanner Using Transillumination Imaging NAD" discusses the use of near-infrared transillumination imaging for biomedical applications such as human biometrics and animal experiments. Pan et al., (2020), "A Multifunctional Skin-Like Wearable Optical Sensor Based on an Optical Micro-/Nanofibre" discusses multifunctional skin-like sensors for next-generation healthcare, robotics, and bioelectronics.

Park et al., (2013), "Multispectral Imaging with Vertical Silicon Nanowires" reports on the demonstration of a compact multispectral imaging system that uses vertical silicon nanowires for a filter array. Park et al., (2015), "Vertically Stacked Photodetector Devices Containing Silicon Nanowires with Engineered Absorption Spectra" discloses a vertically stacked photodetector device containing silicon nanowire photodetectors formed above a silicon substrate that also contains a photodetector. Perumal et al., (2019), "Near Infra-Red Polymeric Nanoparticle Based Optical Imaging in Cancer Diagnosis" reviews the recent progress in NIRF polymeric nanoparticles used for optical imaging particularly on cancer diagnosis. Qiu (2018), "Implantable Ultra-low Power VO2 MEMS Scanner Based Surface-Enhanced Raman Spectroscope for Wide-field Tumor Imaging in Free Moving Small Animals", NSF Award, 2018 (abstract only viewed) discloses tumor-targeting surface enhanced Raman scattering nanoparticles based on multiplexed Raman spectroscopy.

Soliman et al. (2010), "Functional Imaging Using Diffuse Optical Spectroscopy of Neoadjuvant Chemotherapy Response in Women with Locally Advanced Breast Cancer" discloses functional imaging with tomographic near-infrared diffuse optical spectroscopy to measure tissue concentration of deoxyhemoglobin, oxyhemoglobin, percent water, and scattering power. Tank et al., (2020), "Diffuse Optical Spectroscopic Imaging Reveals Distinct Early Breast Tumor Hemodynamic Responses to Metronomic and Maximum Tolerated Dose Regimens" reports on a dual-center study which examined 54 breast tumors receiving NAC measured with DOSI before therapy and the first week following chemotherapy administration.

Tromberg et al. (2016), "Predicting Responses to Neoadjuvant Chemotherapy in Breast Cancer: ACRIN 6691 Trial of Diffuse Optical Spectroscopic Imaging" investigates whether changes from baseline to mid-therapy in a diffuse optical spectroscopic imaging (DOSI)-derived imaging endpoint, the tissue optical index, predict pathologic complete response in women undergoing breast cancer neoadjuvant chemotherapy. Uddin et al., (2020a), "Optimal Breast Cancer Diagnostic Strategy Using Combined Ultrasound and Diffuse Optical Tomography" presents a two-stage diagnostic strategy that is both computationally efficient and accurate. Upputuri, (2019), "Photoacoustic Imaging in the Second Near-Infrared Window: A Review" discusses photoacoustic (PA) imaging that combines optical excitation and ultrasound detection.

Vavadi et al., (2018), "Compact Ultrasound-Guided Diffuse Optical Tomography System for Breast Cancer Imaging" discusses an ultrasound-guided DOT system. Yu et al., (2010), "Near-Infrared, Broad-Band Spectral Imaging of the Human Breast for Quantitative Oximetry: Applications to Healthy and Cancerous Breasts" discusses the examination of ten human subjects with a previously developed instrument for near-infrared diffuse spectral imaging of the female breast. Yuan et al., (2014), "Light-Emitting Diode-Based Multiwavelength Diffuse Optical Tomography System Guided by Ultrasound" discloses a low-cost DOT system using LEDs of four wavelengths in the NIR spectrum as light sources.

Zhang et al., (2020), "Efficacy of Shear-Wave Elastography Versus Dynamic Optical Breast Imaging for Predicting the Pathological Response to Neoadjuvant Chemotherapy in Breast Cancer" discusses the value of shear-wave elastography (SWE) parameters and dynamic optical breast imaging features for predicting pathological responses to neoadjuvant chemotherapy (NACT) in breast cancer (BC). Zhu et al., (2020), "A Review of Optical Breast Imaging: Multi-Modality Systems for Breast Cancer Diagnosis" reviews optical breast imaging using multi-modality platforms. Zhu et al., (2021), "Early Assessment Window for Predicting Breast Cancer Neoadjuvant Therapy Using Biomarkers, Ultrasound, and Diffuse Optical Tomography" assesses the utility of tumor biomarkers, ultrasound (US) and US-guided diffuse optical tomography (DOT) in early prediction of breast cancer response to neoadjuvant therapy (NAT).

SUMMARY OF THE INVENTION

In an example, a wearable device for breast tissue imaging and/or identifying abnormal tissue in a breast can be embodied in a wearable garment with a plurality of light emitters and light receivers. Near-infrared light from the light emitters can be directed into the tissue and the light receivers can receive the light after it has been reflected from the tissue and/or transmitted through the tissue. Changes in the intensity and/or spectrum of the light caused by its reflection from tissue and/or transmission through the tissue can be analyzed to create an image of the breast tissue and/or identify abnormal tissue in the breast. Since breast tissue scatters light in the infrared range, data from a plurality of light emitters and light receivers is needed to more accurately create an image and/or locate areas of abnormal tissue.

In an example, portions of a smart bra can be made from elastic and/or stretchable material. In an example, there can be a layer of opaque fabric between light emitters and receivers and the outer surface of a bra cup. In an example, light emitters and light receivers can be distributed around the outer perimeter of a bra cup. In an example, light emitters and light receivers can be distributed around the concave surface of a bra cup.

In an example, a light emitter can be an LED. In an example, a light emitter can emit near-infrared light. In an example, a light emitter can emit coherent light. In an example, a light emitter can emit light at different wavelengths at different times. In an example, different light emitters can emit light at different wavelengths. In an example, a light emitter can be oriented to emit light along a vector which is substantially perpendicular to a breast surface. In an example, a light emitter can be oriented to emit light toward the center of the breast. In an example, electromagnetic energy can be transmitted to a light emitter through an undulating wire, conductive thread, or conductive yarn. In an example, a smart bra can comprise elastic and/or stretchable conductive threads or yarns. In an example, a smart bra can comprise undulating, sinusoidal, and/or zigzagging conductive threads or yarns.

In an example, changes and/or differences in the intensity of light received by light receivers after traveling through breast tissue along different light paths can be analyzed to create a (3D) image which shows (variation in) breast tissue density. In an example, changes and/or differences in the spectrum of light received by light receivers after traveling through breast tissue along different light paths can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap. In an example, an electronics housing can be removably attached to a front of portion of a smart bra. In an alternative example, a battery, data processor, or data transmitter can be part of a smart bra at a location other than inside the electronics housing. In an example, an electronics housing can be removed from a smart bra before a smart bra is washed and reattached after washing. In an example, an electronics housing can fit into a pocket in a smart bra and be removed from the pocket before the smart bra is washed. In an example, an array of light emitters can be removed from a smart bra before the smart bra is washed and reattached after washing. In an example, a data transmitter can be in wireless communication with a cell phone, smart watch, smart glasses, tablet computer, or laptop computer. In an example, data from a smart bra can be used to create an image of a breast and/or analyze the composition of breast tissue. In an example, data from a smart bra can be used to identify the presence and/or location of (potentially) malignant tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra which is configured to be worn on a person's breasts; wherein the smart bra further comprises a concave hub-and-spoke array of undulating wires; wherein the smart bra further comprises a plurality of light emitters connected to the wires and wherein the light emitters transmit light into breast tissue; and wherein the smart bra further comprises a plurality of light receivers connected to the wires and wherein the light receivers receive the light after it has passed through breast tissue; and wherein changes in the light caused by passing through the breast tissue are used to identify abnormal breast tissue.

In an example, a smart bra to detect abnormal breast tissue can comprise: a smart bra which is configured to be worn on a person's breasts; wherein the smart bra further comprises a concave array of optical sensor clusters; wherein an optical sensor cluster further comprises one or more light emitters which transmit light into breast tissue and/or one or more light receivers which receive the light after it has passed through breast tissue; wherein changes in the light caused by passing through the breast tissue are used to identify abnormal breast tissue; wherein the smart bra further comprises a power source; and wherein the smart bra further comprises a data processor; wherein the smart bra further comprises elastic electroconductive yarns, threads, or filaments; and wherein the optical sensor clusters are connected to the power source and/or to the data processor by the yarns, threads, or filaments.

In an example, a smart bra to detect abnormal breast tissue can comprise: a smart bra which is configured to be worn on a person's breasts; wherein the smart bra further comprises a plurality of light emitters which transmit light into breast tissue; wherein the smart bra further comprises a plurality of conformable transparent light guides which are configured to be between the light emitters and the person's body; wherein the smart bra further comprises a plurality of light receivers which receive the light after it has passed through breast tissue; and wherein changes in the light caused by passing through the breast tissue are used to identify abnormal breast tissue.

INTRODUCTION TO THE FIGURES

FIG. 11 shows a smart bra with a pocket for an array of light emitters and receivers.

FIG. 18 shows a smart bra with a spiral or helical array of light emitters and receivers.

FIG. 19 shows a smart bra with a sunburst array of light emitters and receivers.

DETAILED DESCRIPTION OF THE FIGURES

Figure 1:
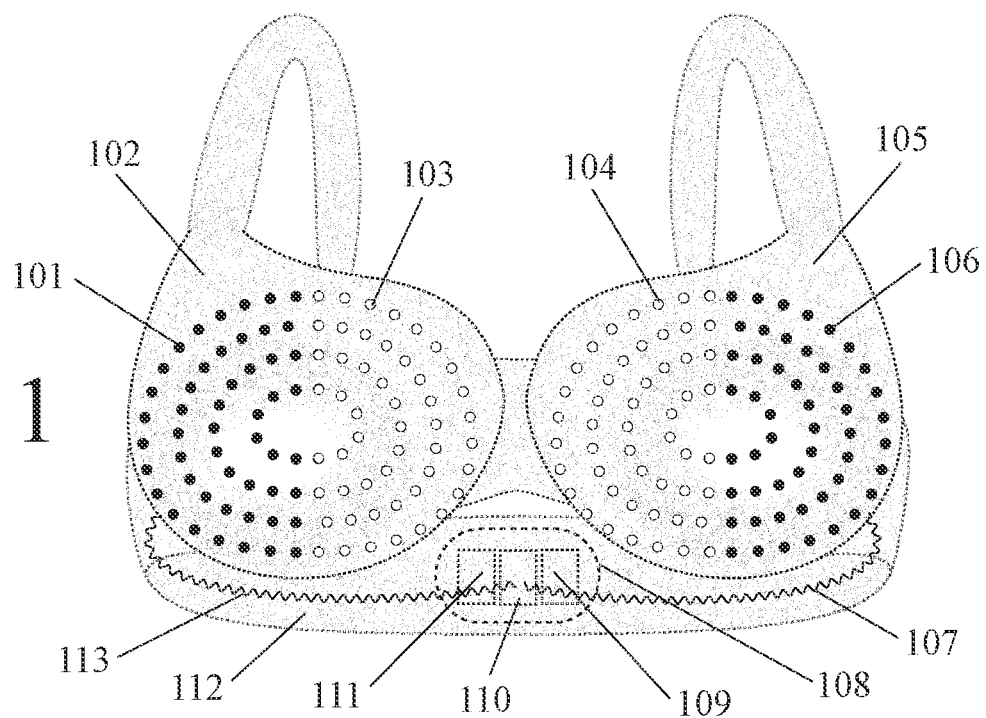
FIG. 1 shows a smart bra with a nested array of rings, with light emitters on a first side of a bra cup and light receivers on a second side of the cup.

FIG. 1 shows an example of a smart bra for optical analysis of breast tissue comprising: a garment worn by a person, wherein the garment further comprises; a first cup 102 worn on the person's right breast; a nested array of rings with light emitters (including 103) and light receivers (including 101) on the first cup, wherein light emitters are on a first side (e.g. left side) of the first cup and light receivers are on a second side (e.g. right side) of the first cup, and wherein light from light emitters received by light receivers is analyzed to create an image of a breast and/or to identify breast tissue composition; a second cup 105 worn on the person's left breast; a nested array of rings with light emitters (including 104) and light receivers (including 106) on the second cup, wherein light emitters are on a first side (e.g. right side) of the second cup and light receivers are on a second side (e.g. left side) of the second cup, and wherein light from light emitters received by light receivers is analyzed to create an image of a breast and/or to identify breast tissue composition; a back strap 112 across the person's back; an electronics housing 108, wherein the electronics housing further comprises a battery 110, data processor 109, and a data transmitter 111; and one or more electromagnetic energy pathways (e.g. undulating wires or conductive threads), 113 and 107, between one or more components in the electronics housing and the first and second cups.

In an example, the garment can be a smart bra. In an example, portions of the garment can be made from elastic and/or stretchable material. In an example, there can be a layer of opaque fabric between light emitters and receivers and the outer surface of a cup. In an example, there can be both light emitters and light receivers in a nested ring. In an example, rings can be concentric as well as nested. In an example, a ring of light emitters and light receivers can be circular, oval, elliptical, or egg-shaped. In an example, light emitters can be distributed around a first half of a ring and light receivers can be distributed around a second half of the ring. In an example, light emitters can be in nested semicircular arcs and light receivers can be in nested semicircular arcs.

In an example, there can be a spoke and ring array of light emitters and light receivers on a cup. In an example, light emitters can be on a first (right or left) side of a cup and light receivers can be on a second (left or right) side of the cup. In an example, light emitters can be on an upper portion of a cup and light receivers can be on a lower portion of the cup, or vice versa. In an example, light emitters can be distributed around the perimeter of a cup and light receivers can be distributed around the concavity of the cup. In an example, light receivers can be distributed around the perimeter of a cup and light emitters can be distributed around the concavity of the cup.

In an example, there can be three nested rings of light emitters and light receivers in each cup. In an example, there can be four nested rings of light emitters and light receivers in each cup. In an example, there can be five or more nested rings of light emitters and light receivers in each cup. In an example, nested rings can be substantially equidistant from each other. In an example, nested rings which are closer to the center of the array can be closer together than nested rings which are farther from the center of the array. In an example, nested rings which are closer to the center of the array can be farther apart than nested rings which are closer to the center of the array. In an example, there can be six nested rings of light emitters and light receivers in each cup.

In an example, a light emitter can be an LED. In an example, a light emitter can emit near-infrared light. In an example, a light emitter can emit coherent light. In an example, a light emitter can emit light at different wavelengths at different times. In an example, different light emitters in an array can emit light at different wavelengths. In an example, electromagnetic energy can be transmitted to a light emitter through an undulating wire, conductive thread, or conductive yarn. In an example, a garment can comprise elastic and/or stretchable conductive threads or yarns. In an example, a garment can comprise undulating, sinusoidal, and/or zigzagging conductive threads or yarns.

In an example, a light emitter can be positioned so as to emit light along a vector which is substantially perpendicular to a breast surface. In an example, a light emitter can be positioned so as to emit light toward the centroid of the breast. In an example, a light emitter can be positioned so as to emit light toward a particular light receiver. In an example, an array of light emitters and light receivers can comprise pairs of light emitters and light receivers which are in optical communication with each other. In an example, light from a light emitter can be received by multiple light emitters after diffusion through breast tissue. In an example, proximal pairs of light emitters in the same ring can be equidistant from each other. In an example, proximal pairs of light emitters in a ring which is closer to the center of the array can be closer together than proximal pairs of light emitters in a ring which is farther from the center of the array. In an example, proximal pairs of light emitters in a ring which is farther from the center of the array can be closer together than proximal pairs of light emitters in a ring which is closer to the center of the array.

In an example, changes and/or differences in the intensity of light received by light receivers along different light path vectors and/or between different pairs of light emitters and light receivers can be analyzed to create a (3D) image which shows (variation in) breast tissue density. In an example, changes and/or differences in the intensity of light received by light receivers after traveling through breast tissue along different light path vectors and/or between different pairs of light emitters and light receivers can be analyzed to create a (3D) image which shows (variation in) breast tissue density.

In an example, changes and/or differences in the spectrum of light received by light receivers along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, electronics housing can be removably attached to a back strap. In an example, electronics housing can be removably attached to a front of portion of a garment. In an alternative example, a battery, data processor, or data transmitter can be part of a garment at a location other than inside the electronics housing. In an example, electronics housing can be removed from a garment before a garment is washed and reattached after washing. In an example, electronics housing can fit into a pocket in a garment and be removed from the pocket before the garment is washed. In an example, an array of light emitters can be removed from a garment before the garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 2:
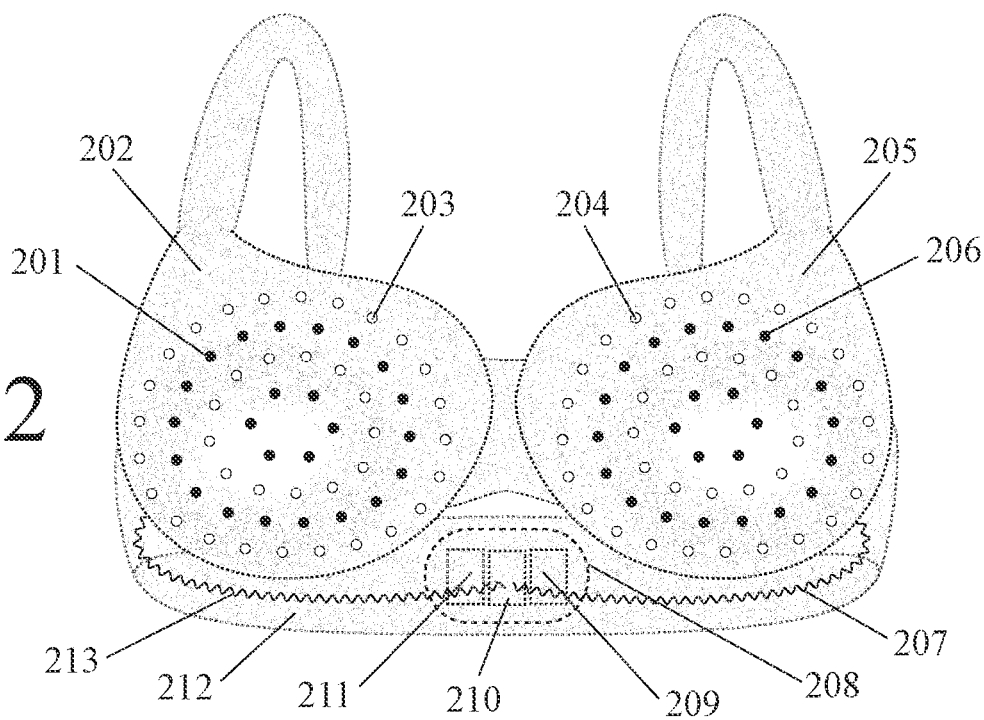
FIG. 2 shows a smart bra with a nested array of rings, with light emitters on some rings and light receivers on other rings.

FIG. 2 shows an example of a smart bra for optical analysis of breast tissue comprising: a garment worn by a person, wherein the garment further comprises; a first cup 202 worn on the person's right breast; nested rings of light emitters (including 203) and nested rings of light receivers (including 201) on the first cup, and wherein light from light emitters received by light receivers is analyzed to create an image of a breast and/or to identify breast tissue composition; a second cup 205 worn on the person's left breast; nested rings of light emitters (including 204) and nested rings of light receivers (including 206) on the second cup, and wherein light from light emitters received by light receivers is analyzed to create an image of a breast and/or to identify breast tissue composition; a back strap 212 across the person's back; an electronics housing 208, wherein the electronics housing further comprises a battery 210, data processor 209, and a data transmitter 211; and one or more electromagnetic energy pathways (e.g. undulating wires or conductive threads), 213 and 207, between one or more components in the electronics housing and the first and second cups.

In an example, portions of the garment can be made from elastic and/or stretchable material. In an example, the garment can be a smart bra. In an example, there can be a layer of opaque fabric between light emitters (and receivers) and the outer surface of a cup. In an example, rings can be concentric as well as nested. In an example, light emitter rings can be nested and/or concentric with respect to light receiver rings, in addition to being nested/or concentric with respect to each other. In an example, a ring of light emitters or receivers can be circular, oval, elliptical, or egg-shaped. In an example, there can be alternating rings of light emitters and light receivers as one moves outward from the center of a cup. In an example, there can be an equal number of rings of light emitters and light receivers in each cup. In an example, there can be two rings each of light emitters and light receivers in each cup. In an example, there can be three rings each of light emitters and light receivers in each cup. In an example, there can be four or more rings each of light emitters and light receivers in each cup. In an example, the number of rings of light emitters can be greater than the number of rings of light receivers. In an example, the number of rings of light emitters can be less than the number of rings of light receivers.

In an example, a light emitter can be an LED. In an example, a light emitter can emit near-infrared light. In an example, a light emitter can emit coherent light. In an example, a light emitter can emit light at different wavelengths at different times. In an example, different light emitters in an array can emit light at different wavelengths. In an example, electromagnetic energy can be transmitted to a light emitter through an undulating wire, conductive thread, or conductive yarn. In an example, a garment can comprise elastic and/or stretchable conductive threads or yarns. In an example, a garment can comprise undulating, sinusoidal, and/or zigzagging conductive threads or yarns. In an example, a light emitter can be positioned so as to emit light along a vector which is substantially perpendicular to a breast surface. In an example, a light emitter can be positioned so as to emit light toward the centroid of the breast. In an example, a light emitter can be positioned so as to emit light toward a particular light receiver. In an example, light from a light emitter can be received by multiple light emitters after diffusion through breast tissue.

In an example, rings can be substantially equidistant from each other. In an example, rings which are closer to the center of the array can be closer together than rings which are farther from the center of the array. In an example, rings which are closer to the center of the array can be farther apart than nested rings which are closer to the center of the array. In an example, light emitters or receivers in the same ring can be equidistant from each other. In an example, light emitters or receivers in a ring which is closer to the center of the array can be closer together than those in a ring which is farther from the center of the array. In an example, light emitters or receiver in a ring which is farther from the center of the array can be closer together than those in a ring which is closer to the center of the array.

In an example, changes and/or differences in the intensity of light received by light receivers along different light path vectors and/or between different pairs of light emitters and light receivers can be analyzed to create a (3D) image which shows (variation in) breast tissue density. In an example, changes and/or differences in the intensity of light received by light receivers after traveling through breast tissue along different light path vectors and/or between different pairs of light emitters and light receivers can be analyzed to create a (3D) image which shows (variation in) breast tissue density. In an example, changes and/or differences in the spectrum of light received by light receivers along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap. In an example, an electronics housing can be removably attached to a front of portion of a garment. In an alternative example, a battery, data processor, and/or data transmitter can be part of a garment at a location other than inside the electronics housing. In an example, an electronics housing can be removed from a garment before a garment is washed and reattached after washing. In an example, an electronics housing can fit into a pocket in a garment and be removed from the pocket before the garment is washed. In an example, an array of light emitters can be removed from a garment before the garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 3:
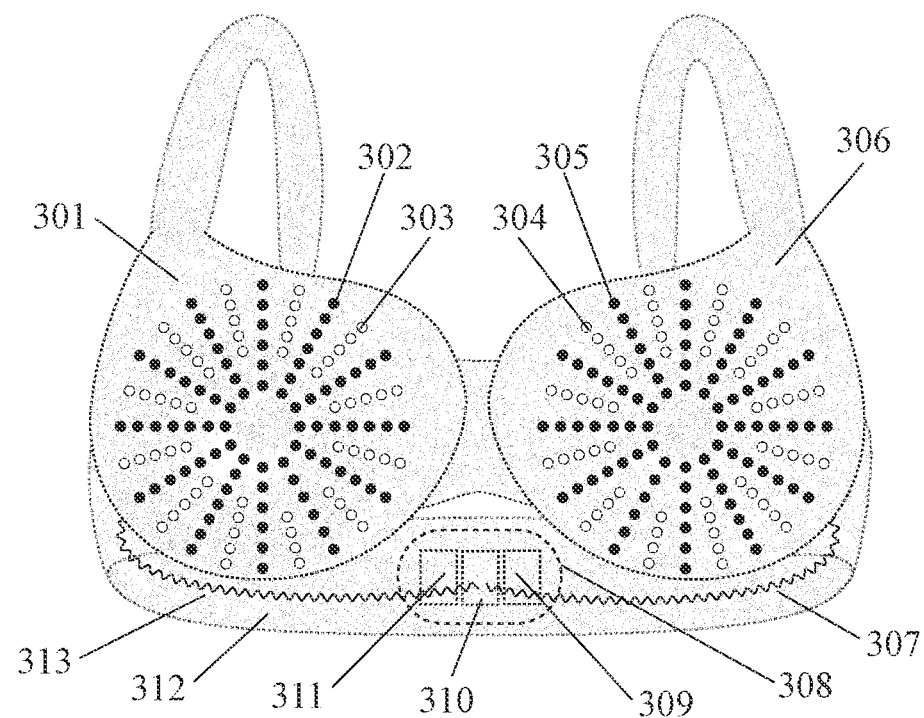
FIG. 3 shows a smart bra with radial spokes, with light emitters on some spokes and light receivers on other spokes.

FIG. 3 shows an example of a smart bra for optical analysis of breast tissue comprising: a garment worn by a person, wherein the garment further comprises; a first cup 301 worn on the person's right breast; radial spokes of light emitters (including 303) and radial spokes of light receivers (including 302) on the first cup, and wherein light from light emitters received by light receivers is analyzed to create an image of a breast and/or to identify breast tissue composition; a second cup 306 worn on the person's left breast; radial spokes of light emitters (including 304) and radial spokes of light receivers (including 305) on the second cup, and wherein light from light emitters received by light receivers is analyzed to create an image of a breast and/or to identify breast tissue composition; a back strap 312 across the person's back; an electronics housing 308, wherein the electronics housing further comprises a battery 310, data processor 309, and a data transmitter 311; and one or more electromagnetic energy pathways (e.g. undulating wires or conductive threads), 313 and 307, between one or more components in the electronics housing and the first and second cups.

In an example, portions of a garment can be made from elastic and/or stretchable material. In an example, a garment can be a smart bra. In an example, there can be opaque fabric between light emitters (and receivers) and the outer surface of a cup. In an example, there can be alternating spokes of light emitters and light receivers as one moves clockwise around a cup. In an example, there can be an equal number of spokes of light emitters and light receivers in a cup. In an example, there can be two spokes each of light emitters and light receivers in a cup. In an example, there can be three spokes each of light emitters and light receivers in a cup. In an example, there can be four or more spokes each of light emitters and light receivers in a cup. In an example, the number of spokes of light emitters can be greater than the number of spokes of light receivers in a cup. In an example, the number of spokes of light emitters can be less than the number of spokes of light receivers in a cup.

In an example, a light emitter can be an LED. In an example, a light emitter can emit near-infrared light. In an example, a light emitter can emit coherent light. In an example, a light emitter can emit light at different wavelengths at different times. In an example, different light emitters in an array can emit light at different wavelengths. In an example, electromagnetic energy can be transmitted to a light emitter through an undulating wire, conductive thread, or conductive yarn. In an example, a garment can comprise elastic and/or stretchable conductive threads or yarns. In an example, a garment can comprise undulating, sinusoidal, and/or zigzagging conductive threads or yarns. In an example, a light emitter can be positioned so as to emit light along a vector which is: substantially perpendicular to a breast surface; directed toward the centroid of the breast; and/or directed toward a particular light receiver. In an example, light from a light emitter can be received by multiple light emitters after diffusion through breast tissue.

In an example, light emitters or receivers in the same spoke can be equidistant from each other. In an example, light emitters or receivers on a spoke which are closer to the center of a cup can be closer together than those on the spoke which are farther from the center of the cup. In an example, light emitters or receivers in a spoke which are farther from the center of a cup can be closer together than those on the spoke which are farther from the center of the cup. In an example, there can be variation in the distance from the most central point of different spokes and the center of the cup (or the center of the array of spokes). In an example (as shown in FIG. 3), the ends of spokes of light receivers can be closer to the center of a cup than the ends of spokes of light emitters. In an alternative example, the ends of spokes of light emitters can be closer to the center of a cup than the ends of spokes of light receivers. In an example, there can be two (or more) hub-and-spoke arrays of light emitters and/or light receivers in a cup, wherein different hub-and-spoke arrays have different size central hubs.

In an example, changes and/or differences in the intensity of light received by light receivers along different light path vectors and/or between different pairs of light emitters and light receivers can be analyzed to create a (3D) image which shows (variation in) breast tissue density. In an example, changes and/or differences in the intensity of light received by light receivers after traveling through breast tissue along different light path vectors and/or between different pairs of light emitters and light receivers can be analyzed to create a (3D) image which shows (variation in) breast tissue density. In an example, changes and/or differences in the spectrum of light received by light receivers along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap. In an example, an electronics housing can be removably attached to a front of portion of a garment. In an alternative example, a battery, data processor, and/or data transmitter can be part of a garment at a location other than inside the electronics housing. In an example, an electronics housing can be removed from a garment before a garment is washed and reattached after washing. In an example, an electronics housing can fit into a pocket in a garment and be removed from the pocket before the garment is washed. In an example, an array of light emitters can be removed from a garment before the garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 4:
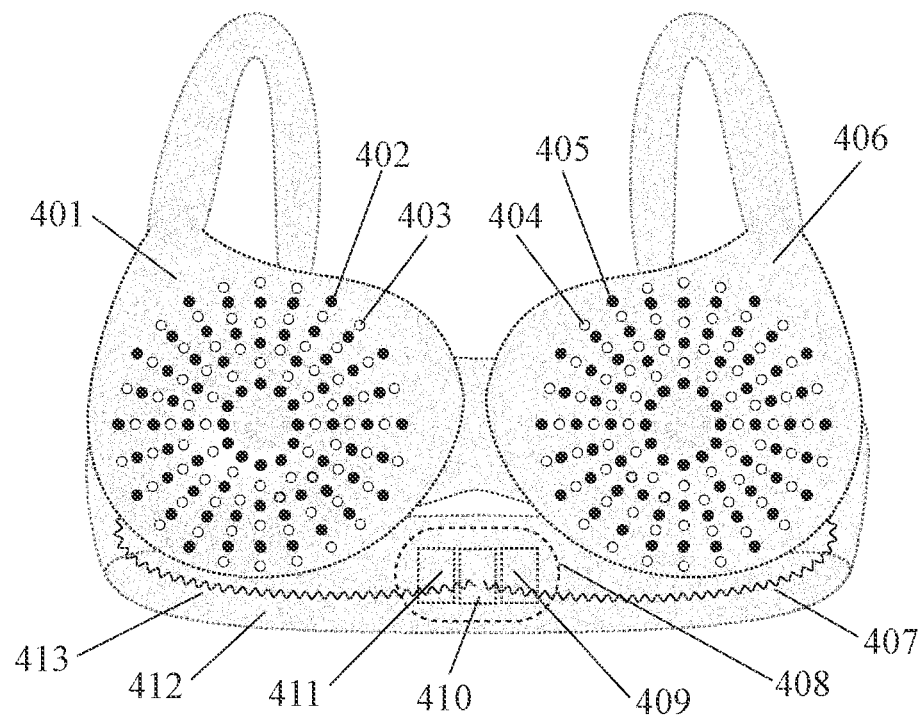
FIG. 4 shows a smart bra with radial spokes, with alternating light emitters and receivers on a spoke.

FIG. 4 shows an example of a smart bra for optical analysis of breast tissue comprising: a garment worn by a person, wherein the garment further comprises; a first cup 401 worn on the person's right breast, with radial spokes of alternating light emitters (including 403) and light receivers (including 402) on the first cup, wherein light from light emitters received by light receivers is analyzed to create an image of a breast and/or to identify breast tissue composition; a second cup 406 worn on the person's left breast, with radial spokes of alternating light emitters (including 404) and light receivers (including 405) on the second cup, wherein light from light emitters received by light receivers is analyzed to create an image of a breast and/or to identify breast tissue composition; a back strap 412 across the person's back; an electronics housing 408, wherein the electronics housing further comprises a battery 410, data processor 409, and a data transmitter 411; and one or more electromagnetic energy pathways (e.g. undulating wires or conductive threads), 413 and 407, between one or more components in the electronics housing and the first and second cups.

In an example, portions of a garment can be made from elastic and/or stretchable material. In an example, a garment can be a smart bra. In an example, there can be an equal number light emitters and light receivers on a spoke. In an example, there can be more light emitters than light receivers on a spoke. In an example, there can be more light receivers than light emitters on a spoke. In an example, there can be six spokes per cup. In an example, there can be eight spokes per cup. In an example, there can be twelve or more spokes per cup.

In an example, light emitters or receivers in the same spoke can be pair-wise equidistant. In an example, light emitters or receivers on a spoke which are closer to the center of a cup can be closer together than those on the spoke which are farther from the center of the cup. In an example, light emitters or receivers in a spoke which are farther from the center of a cup can be closer together than those on the spoke which are farther from the center of the cup. In an example, there can be variation in the distance from the most central ends of different spokes and the center of the cup (or the center of the array of spokes). In an example, the central ends of different spokes can be different distances from the center of the cup (or center of the spoke array). In an example, there can be two (or more) hub-and-spoke arrays with different size central hubs.

In an example, a light emitter can be an LED. In an example, a light emitter can emit near-infrared light and/or coherent light. In an example, a light emitter can emit light at different wavelengths at different times. In an example, different light emitters in an array can emit light at different wavelengths. In an example, a garment can comprise: undulating or zigzag wires; or elastic and/or stretchable conductive threads or yarns. In an example, a light emitter can be positioned so as to emit light along a vector which is: substantially perpendicular to a breast surface; directed toward the centroid of the breast; and/or directed toward a particular light receiver. In an example, light from a light emitter can be received by multiple light emitters after diffusion through breast tissue.

In an example, changes and/or differences in the intensity of light received by light receivers after traveling through breast tissue along different light path vectors and/or between different pairs of light emitters and light receivers can be analyzed to create a (3D) image which shows (variation in) breast tissue density. In an example, changes and/or differences in the spectrum of light received by light receivers after traveling through breast tissue along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap or a front of portion of a garment. In an alternative example, a battery, data processor, and/or data transmitter can be part of a garment at a location other than inside the electronics housing. In an example, an electronics housing and/or an array of light emitters and receivers can be removed from a garment before a garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 5:
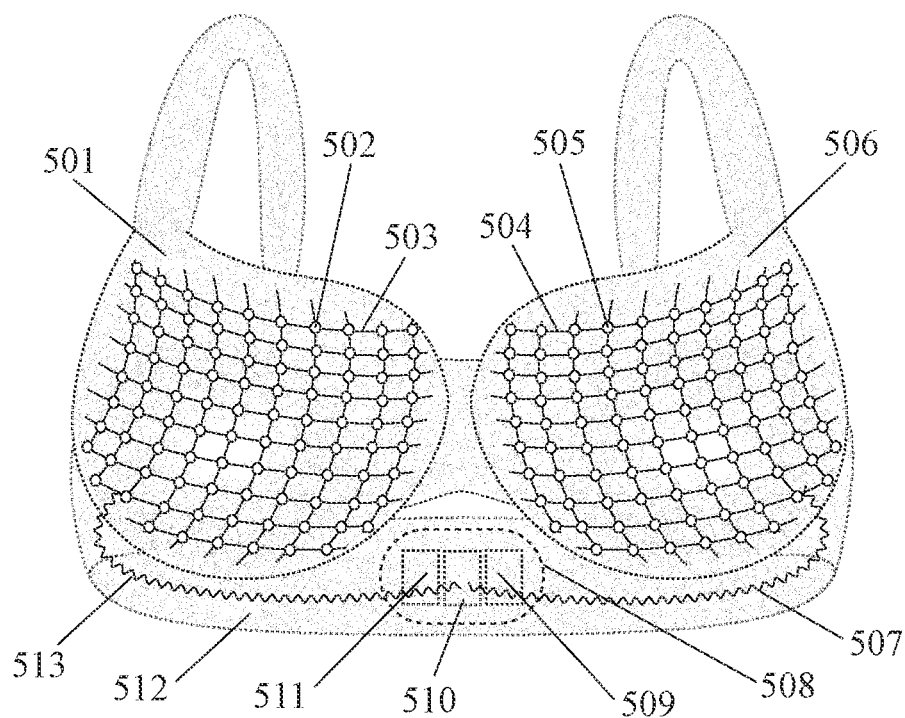
FIG. 5 shows a smart bra with light emitters and receivers on a quadrilateral grid of flexible electromagnetic pathways.

FIG. 5 shows an example of a smart bra for optical analysis of breast tissue comprising: a garment worn by a person, wherein the garment further comprises; a first cup 501 worn on the person's right breast, wherein the first cup further comprises an array or matrix (including 502) of light emitters and light receivers connected by a grid 503 of flexible electromagnetic energy pathways (e.g. wires, conductive threads, or conductive yarns), wherein light from light emitters received by light receivers is analyzed to create an image of a breast and/or to identify breast tissue composition; a second cup 506 worn on the person's left breast, wherein the second cup further comprises an array or matrix (including 505) of light emitters and light receivers connected by a grid 504 of flexible electromagnetic energy pathways (e.g. wires, conductive threads, or conductive yarns), wherein light from light emitters received by light receivers is analyzed to create an image of a breast and/or to identify breast tissue composition; a back strap 512 across the person's back; an electronics housing 508, wherein the electronics housing further comprises a battery 510, data processor 509, and a data transmitter 511; and one or more electromagnetic energy pathways (e.g. undulating wires or conductive threads), 513 and 507, between one or more components in the electronics housing and the first and second cups.

In an example, light emitters and/or light receivers can be located where linear elements (e.g. rows and columns) in a grid of electromagnetic energy pathways intersect. In an example, application of electromagnetic energy to two intersecting pathways in a grid can activate a light emitter at the intersection of those two pathways. In an example, a grid can have quadrilateral elements. In an example, intersecting rows and columns in a grid can form quadrilateral openings. In an example, a grid can have hexagonal elements. In an example, intersecting linear elements in a grid can form hexagonal openings. In an example, light emitters and/or light receivers which are closer to the center of a cup can be closer together than those which are farther from the center of the cup (or the center of the grid). In an example, light emitters and/or light receivers which are father from the center of a cup can be closer together than those which are closer to the center of the cup (or the center of the grid). In an example, light emitters and light receivers can alternate as one spans a grid in a lateral (left to right) manner. In an example, light emitters and light receivers can alternate as one spans a grid in a descending (up to down) manner.

In an example, a light emitter can be an LED which emits near-infrared light and/or coherent light. In an example, a single light emitter can emit light at different wavelengths at different times. In an example, two or more different light emitters in an array or matrix can emit light at different wavelengths. In an example, a light emitter can emit light along a vector which: perpendicular to a breast surface; toward a breast centroid; and/or toward a particular light receiver. In an example, light from a light emitter can be received by multiple light emitters after diffusion through breast tissue. In an example, changes and/or differences in the intensity and/or spectral distribution of light received by light receivers after traveling through breast tissue along different light path vectors and/or between different pairs of light emitters and light receivers can be analyzed to create a (3D) image which shows (variation in) breast tissue density and/or composition. In an example, changes and/or differences in the spectrum of light received by light receivers after traveling through breast tissue can be analyzed to identify (potentially) malignant tissue.

In an example, an electronics housing can be removably attached to a back strap or a front of portion of a garment. In an alternative example, a battery, a data processor, or a data transmitter can be inside the electronics housing. In an example, an electronics housing and/or an array of light emitters and receivers can be removed from a garment before the garment is washed and can be reattached after washing. In an example, data from a garment can be used to create an image of a breast and/or to analyze the composition of breast tissue. In an example, data from a garment can be used to identify the presence and/or location of (potentially) malignant tissue.

Figure 6:
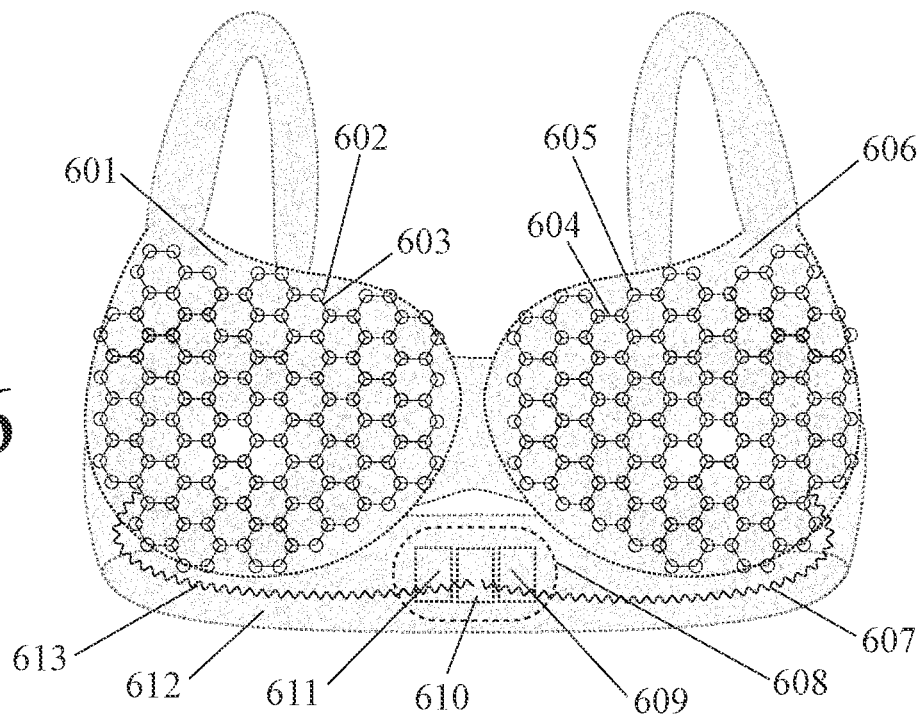
FIG. 6 shows a smart bra with light emitters and receivers on a hexagonal grid of flexible electromagnetic pathways.

FIG. 6 shows an example of a smart bra for optical analysis of breast tissue comprising: a garment worn by a person, wherein the garment further comprises; a first cup 601 worn on the person's right breast, wherein the first cup further comprises a hexagonal-element array or matrix (including 602) of light emitters and light receivers connected by a hexagonal-element grid 603 of flexible electromagnetic energy pathways (e.g. wires, conductive threads, or conductive yarns), wherein light from light emitters received by light receivers is analyzed to create an image of a breast and/or to identify breast tissue composition; a second cup 606 worn on the person's left breast, wherein the second cup further comprises a hexagonal-element array or matrix (including 605) of light emitters and light receivers connected by a hexagonal-element grid 604 of flexible electromagnetic energy pathways (e.g. wires, conductive threads, or conductive yarns), wherein light from light emitters received by light receivers is analyzed to create an image of a breast and/or to identify breast tissue composition; a back strap 612 across the person's back; an electronics housing 608, wherein the electronics housing further comprises a battery 610, data processor 609, and a data transmitter 611; and one or more electromagnetic energy pathways (e.g. undulating wires or conductive threads), 613 and 607, between one or more components in the electronics housing and the first and second cups.

In an example, light emitters and/or light receivers can be located where linear elements in a grid of electromagnetic energy pathways intersect. In an example, a grid can have hexagonal elements. In an example, intersecting linear elements in a grid can form hexagonal openings. In an example, light emitters and/or light receivers which are closer to the center of a cup can be closer together than those which are farther from the center of the cup (or the center of the grid). In an example, light emitters and/or light receivers which are father from the center of a cup can be closer together than those which are closer to the center of the cup (or the center of the grid). In an example, light emitters and light receivers can alternate as one spans a grid in a lateral (left to right) manner. In an example, light emitters and light receivers can alternate as one spans a grid in a descending (up to down) manner.

In an example, a light emitter can be an LED which emits near-infrared light and/or coherent light. In an example, a single light emitter can emit light at different wavelengths at different times. In an example, two or more different light emitters in an array or matrix can emit light at different wavelengths. In an example, a light emitter can emit light along a vector which: perpendicular to a breast surface; toward a breast centroid; and/or toward a particular light receiver. In an example, light from a light emitter can be received by multiple light emitters after diffusion through breast tissue. In an example, changes and/or differences in the intensity and/or spectral distribution of light received by light receivers after traveling through breast tissue along different light path vectors and/or between different pairs of light emitters and light receivers can be analyzed to create a (3D) image which shows (variation in) breast tissue density and/or composition. In an example, changes and/or differences in the spectrum of light received by light receivers after traveling through breast tissue can be analyzed to identify (potentially) malignant tissue.

In an example, an electronics housing can be removably attached to a back strap or a front of portion of a garment. In an alternative example, a battery, a data processor, or a data transmitter can be inside the electronics housing. In an example, an electronics housing and/or an array of light emitters and receivers can be removed from a garment before the garment is washed and can be reattached after washing. In an example, data from a garment can be used to create an image of a breast and/or to analyze the composition of breast tissue. In an example, data from a garment can be used to identify the presence and/or location of (potentially) malignant tissue.

Figure 7:
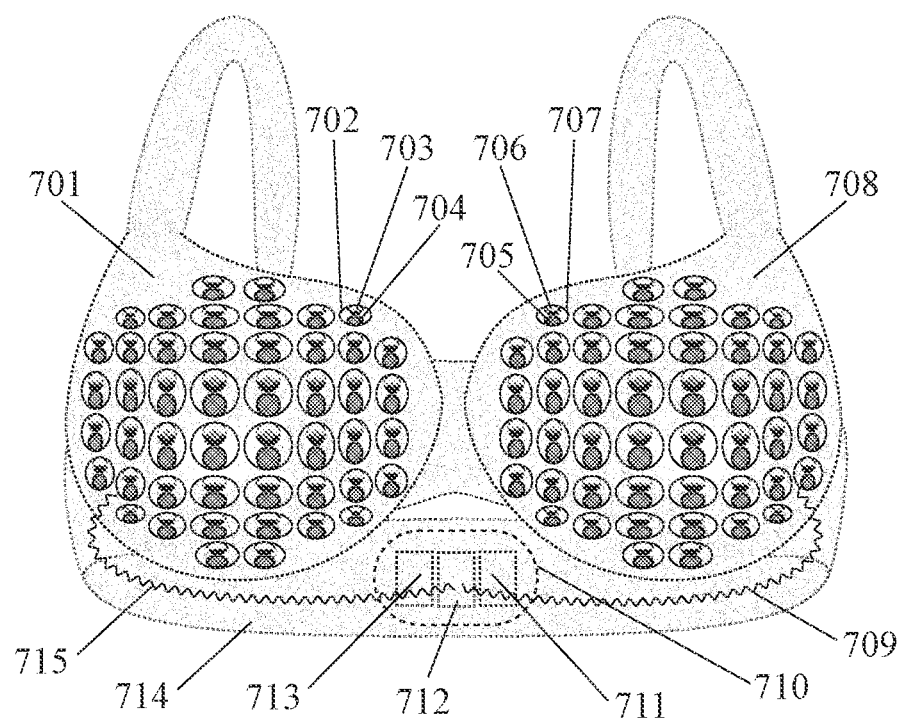
FIG. 7 shows a smart bra with an array of imaging components, each having a light emitter and a light receiver.

FIG. 7 shows an example of a smart bra for optical analysis of breast tissue comprising: a garment worn by a person, wherein the garment further comprises; a first cup 701 worn on the person's right breast, wherein the first cup further comprises an array of imaging components 702, wherein each imaging component includes a light emitter 703 and a light receiver 704, and wherein light from the light emitter received by the light receiver is analyzed as part of the creation of an image of a breast and/or identification of breast tissue composition; a second cup 708 worn on the person's left breast, wherein the second cup further comprises an array of imaging components 705, wherein each imaging component includes a light emitter 706 and a light receiver 707, and wherein light from the light emitter received by the light receiver is analyzed as part of the creation of an image of a breast and/or identification of breast tissue composition; a back strap 714 across the person's back; an electronics housing 710, wherein the electronics housing further comprises a battery 712, data processor 711, and a data transmitter 713; and one or more electromagnetic energy pathways (e.g. undulating wires or conductive threads), 715 and 709, between one or more components in the electronics housing and the first and second cups.

In an example, each imaging component can include a single light emitter and a single light receiver. In an example, each imaging component can include two light emitters and a one light receiver. In an example, each imaging component can include two light emitters which emit light at two different wavelengths, respectively, and a one light receiver. In an example, each imaging component can include two light emitters at different distances from a light emitter. In an example, each imaging component can include two light emitters at different orientations and/or angles from a light emitter. In an example, the orientations of light emitters relative to light receivers in different imaging components on a cup can be symmetric (e.g. reflected) relative to the center of the cup. In an example, different light emitters in an imaging component can emit light at different times. In an example, different light emitters in an imaging component can emit light at different frequencies at different times. In an example, imaging components which are closer to the center of a cup can be closer together than those which are farther from the center of the cup (or the center of the grid). In an example, imaging components which are father from the center of a cup can be closer together than those which are closer to the center of the cup (or the center of the grid).

In an example, each imaging component can include three light emitters and a one light receiver. In an example, each imaging component can include three light emitters which emit light at three different wavelengths, respectively, and a one light receiver. In an example, each imaging component can include three light emitters at different distances from a light emitter. In an example, each imaging component can include three light emitters at different orientations and/or angles from a light emitter. In an example, each imaging component can include four or more light emitters and a one light receiver. In an example, each imaging component can include four or more light emitters which emit light at four or more different wavelengths, respectively, and a one light receiver. In an example, each imaging component can include four or more light emitters at different distances from a light emitter. In an example, each imaging component can include four or more light emitters at different orientations and/or angles from a light emitter.

In an example, a light emitter can be an LED which emits near-infrared light and/or coherent light. In an example, a single light emitter can emit light at different wavelengths at different times. In an example, two or more different light emitters in an array or matrix can emit light at different wavelengths. In an example, a light emitter can emit light along a vector which: perpendicular to a breast surface; toward a breast centroid; and/or toward a particular light receiver. In an example, changes and/or differences in the intensity and/or spectral distribution of light received by light receivers after traveling through breast tissue can be analyzed to create a (3D) image which shows (variation in) breast tissue density and/or composition. In an example, changes and/or differences in the spectrum of light received by light receivers after traveling through breast tissue can be analyzed to identify (potentially) malignant tissue.

In an example, an electronics housing can be removably attached to a back strap or a front of portion of a garment. In an alternative example, a battery, a data processor, or a data transmitter can be inside the electronics housing. In an example, an electronics housing and/or an array of light emitters and receivers can be removed from a garment before the garment is washed and can be reattached after washing. In an example, data from a garment can be used to create an image of a breast and/or to analyze the composition of breast tissue. In an example, data from a garment can be used to identify the presence and/or location of (potentially) malignant tissue.

Figure 8:
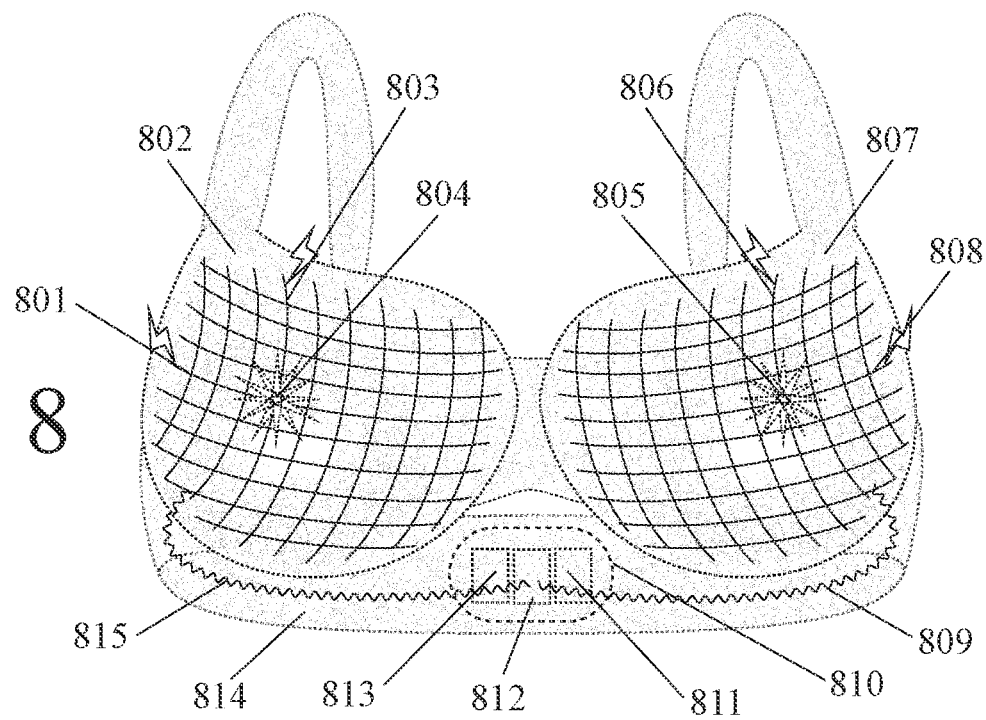
FIG. 8 shows a smart bra with a grid of electromagnetic pathways, wherein sending electromagnetic energy into intersecting pathways causes light emission where they intersect.

FIG. 8 shows an example of a smart bra for optical analysis of breast tissue comprising: a garment worn by a person, wherein the garment further comprises; a first cup 802 worn on the person's right breast, wherein the first cup further comprises a grid of intersecting (or overlapping) electromagnetic energy pathways, and wherein application of electromagnetic energy to a subset (801 and 803) of the intersecting electromagnetic energy pathways causes light emission from a location 804 where they intersect, and wherein changes in light emitted from the location caused by the light traveling through breast tissue are analyzed as part of the creation of an image of a breast and/or identification of breast tissue composition; a second cup 807 worn on the person's left breast, wherein the second cup further comprises a grid of intersecting (or overlapping) electromagnetic energy pathways, and wherein application of electromagnetic energy to a subset (806 and 808) of the intersecting electromagnetic energy pathways causes light emission from the location 805 where they intersect, and wherein changes in light emitted from the location caused by the light traveling through breast tissue are analyzed as part of the creation of an image of a breast and/or identification of breast tissue composition; a back strap 814 across the person's back; an electronics housing 810, wherein the electronics housing further comprises a battery 812, data processor 811, and a data transmitter 813; and one or more electromagnetic energy pathways (e.g. undulating wires or conductive threads), 815 and 809, between one or more components in the electronics housing and the first and second cups.

In an example, a grid can have quadrilateral elements. In an example, intersecting linear elements in a grid can form quadrilateral openings. In an example, a grid can have hexagonal elements. In an example, intersecting linear elements in a grid can form hexagonal openings. In an example, a grid can be more dense (e.g. having elements closer together) toward the center of a cup than toward the periphery of a cup. In an example, a grid can be less dense (e.g. having elements farther apart) toward the center of a cup than toward the periphery of a cup. In an example a cup can comprise a photoactive layer which emits light when excited by electromagnetic energy. In an example, application of electromagnetic energy to two or more pathways in a grid can cause such a photoactive layer to emit light at the intersection of these two or more pathways.

In an example, a cup can further comprise light receivers which receive light emitted from the intersection of two or more pathways in a grid. In an example, changes and/or differences in the intensity and/or spectral distribution of light received by light receivers after traveling through breast tissue can be analyzed to create a (3D) image which shows (variation in) breast tissue density and/or composition. In an example, changes and/or differences in the spectrum of light received by light receivers after traveling through breast tissue can be analyzed to identify (potentially) malignant tissue.

In an example, an electronics housing can be removably attached to a back strap or a front of portion of a garment. In an alternative example, a battery, a data processor, or a data transmitter can be inside the electronics housing. In an example, an electronics housing and/or an array of light emitters and receivers can be removed from a garment before the garment is washed and can be reattached after washing. In an example, data from a garment can be used to create an image of a breast and/or to analyze the composition of breast tissue. In an example, data from a garment can be used to identify the presence and/or location of (potentially) malignant tissue.

Figure 9:
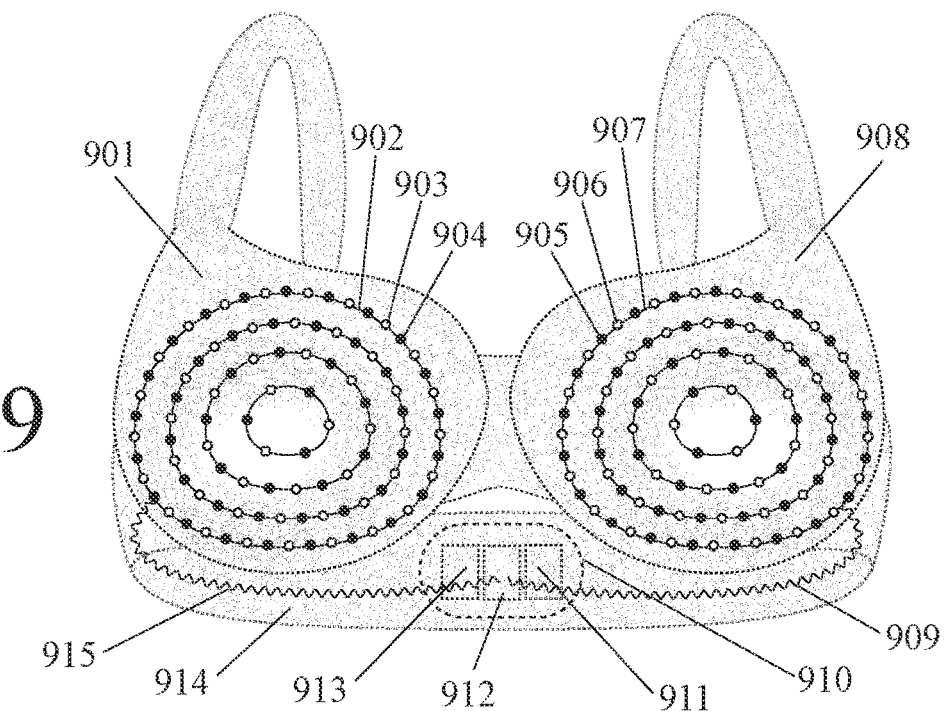
FIG. 9 shows a smart bra with a nested array of rings, with alternating light emitters and receivers on a ring.

FIG. 9 shows an example of a smart bra for optical analysis of breast tissue comprising: a garment worn by a person, wherein the garment further comprises; a first cup 901 worn on the person's right breast, wherein the first cup further comprises (concentric) nested rings (such as 902) of light emitters (such as 903) and light receivers (such as 904), wherein there is an alternating sequence of light emitters and light receivers around each ring, and wherein light from light emitters received by light receivers is analyzed to create an image of a breast and/or to identify breast tissue composition; a second cup 908 worn on the person's left breast, wherein the second cup further comprises (concentric) nested rings (such as 907) of light emitters (such as 906) and light receivers (such as 905), wherein there is an alternating sequence of light emitters and light receivers around each ring, and wherein light from light emitters received by light receivers is analyzed to create an image of a breast and/or to identify breast tissue composition; a back strap 914 across the person's back; an electronics housing 910, wherein the electronics housing further comprises a battery 912, data processor 911, and a data transmitter 913; and one or more electromagnetic energy pathways (e.g. undulating wires or conductive threads), 915 and 909, between one or more components in the electronics housing and the first and second cups.

In an example, rings of light emitters and receivers can be concentric as well as nested. In an example, a ring can be circular, oval, elliptical, or egg-shaped. In an example, there can be four rings in each cup. In an example, there can be five rings in each cup. In an example, there can be six or more rings in each cup. In an example, rings can be substantially equidistant. In an example, rings which are closer to the center of the cup can be closer together than rings which are farther from the center of the cup. In an example, rings which are closer to the center of the cup can be farther apart than nested rings which are closer to the center of the cup. In an example, light emitters and receivers in the same ring can be equidistant. In an example, light emitters and receivers in a ring which is closer to the center of a cup can be closer together than those in a ring which is farther from the center of the cup. In an example, light emitters and receiver in a ring which is farther from the center of a cup can be closer together than those in a ring which is closer to the center of the cup.

In an example, a light emitter can be an LED. In an example, a light emitter can emit near-infrared light and/or coherent light. In an example, a light emitter can emit light at different wavelengths at different times. In an example, different light emitters in an ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and reattached after washing.

Figure 10:
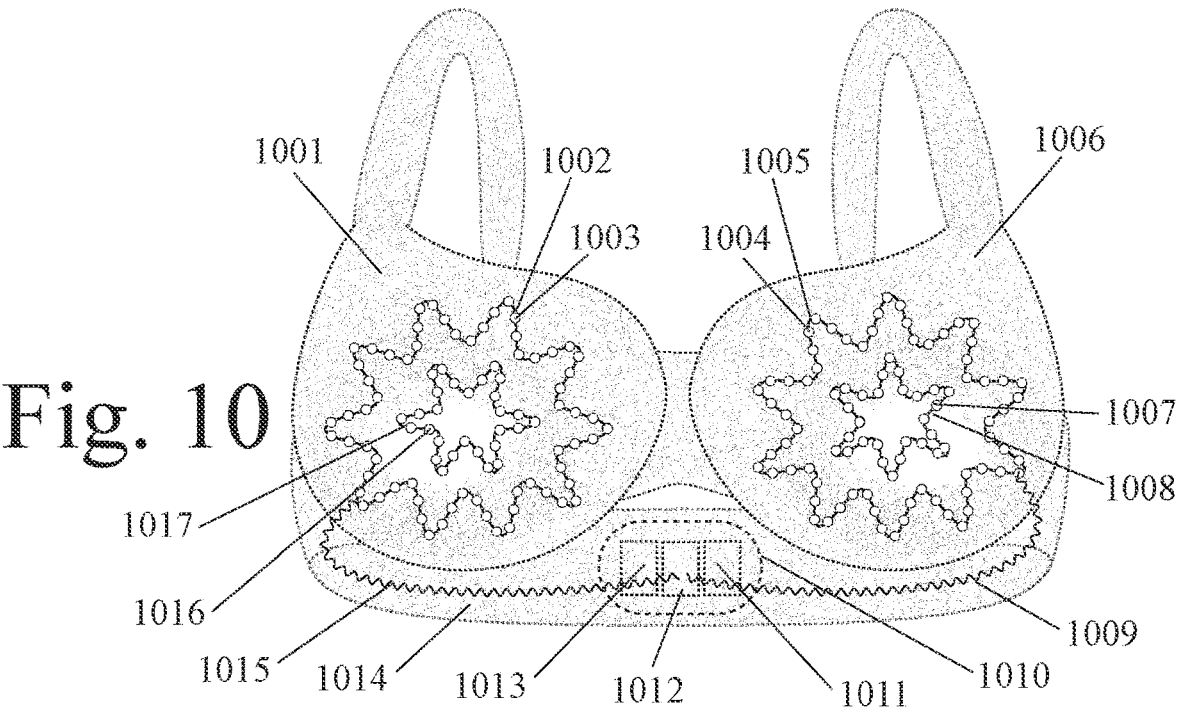
FIG. 10 shows a smart bra with nested sinusoidal rings of light emitters and receivers.

FIG. 10 shows an example of a smart bra for optical analysis of breast tissue comprising: a garment worn by a person, wherein the garment further comprises; a first cup 1001 worn on the person's right breast, wherein the first cup further comprises a plurality of nested sinusoidal rings (such as 1002 and 1017) of light emitters (such as 1003) and light receivers (such as 1016), wherein light from light emitters received by light receivers is analyzed to create an image of a breast and/or to identify breast tissue composition; a second cup 1006 worn on the person's left breast, wherein the second cup further comprises a plurality of nested sinusoidal rings (such as 1005 and 1008) of light emitters (such as 1004) and light receivers (such as 1007), wherein light from light emitters received by light receivers is analyzed to create an image of a breast and/or to identify breast tissue composition; a back strap 1014 across the person's back; an electronics housing 1010, wherein the electronics housing further comprises a battery 1012, data processor 1011, and a data transmitter 1013; and one or more electromagnetic energy pathways (e.g. undulating wires or conductive threads), 1015 and 1009, between one or more components in the electronics housing and the first and second cups.

In an example, rings of light emitters and receivers can be concentric as well as nested. In an example, there can be two sinusoidal rings in each cup. In an example, there can be three sinusoidal rings in each cup. In an example, there can be four or more sinusoidal rings in each cup. In an example, each ring may have only light emitters or only light receivers. In an example, the same ring may have both light emitters and light receivers. In an example, a sinusoidal ring can have four undulations. In an example, a sinusoidal ring can have five undulations (e.g. a rounded five-pointed-star shape). In an example, a sinusoidal ring can have six undulations (e.g. a rounded six-pointed-star shape). In an example, a sinusoidal ring can have eight or more undulations. In an example, the undulations of proximal undulating rings can interdigitate.

In an example, a light emitter can be an LED. In an example, a light emitter can emit near-infrared light and/or coherent light. In an example, a light emitter can emit light at different wavelengths at different times. In an example, different light emitters in a ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

FIG. 11 shows an example of a smart bra for optical analysis of breast tissue comprising: a garment worn by a person, wherein the garment further comprises; a first cup 1101 worn on the person's right breast, wherein the first cup further comprises a pocket (or pouch) 1105, wherein the first cup further comprises an array 1103 of light emitters and light receivers which can be inserted into the pocket and removed from the pocket, and wherein light from light emitters received by light receivers is analyzed to create an image of a breast and/or to identify breast tissue composition; a second cup 1102 worn on the person's left breast, wherein the second cup further comprises a pocket (or pouch) 1106, wherein the second cup further comprises an array 1104 of light emitters and light receivers which can be inserted into the pocket and removed from the pocket, and wherein light from light emitters received by light receivers is analyzed to create an image of a breast and/or to identify breast tissue composition; a back strap 1112 across the person's back; an electronics housing 1108, wherein the electronics housing further comprises a battery 1110, data processor 1109, and a data transmitter 1111; and one or more electromagnetic energy pathways (e.g. undulating wires or conductive threads), 1113 and 1107, between one or more components in the electronics housing and the first and second cups. The upper portion of FIG. 11 shows this garment at a first point in time wherein arrays of light emitters and receivers have been inserted into pockets (or pouches) on the cups. The lower portion of FIG. 11 shows this garment at a second point in time wherein arrays of light emitters and receivers have been removed from pockets (or pouches) on the cups.

In an example, a light emitter can be an LED. In an example, a light emitter can emit near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing can also be detached from a garment before washing and then reattached after washing.

Figure 12:
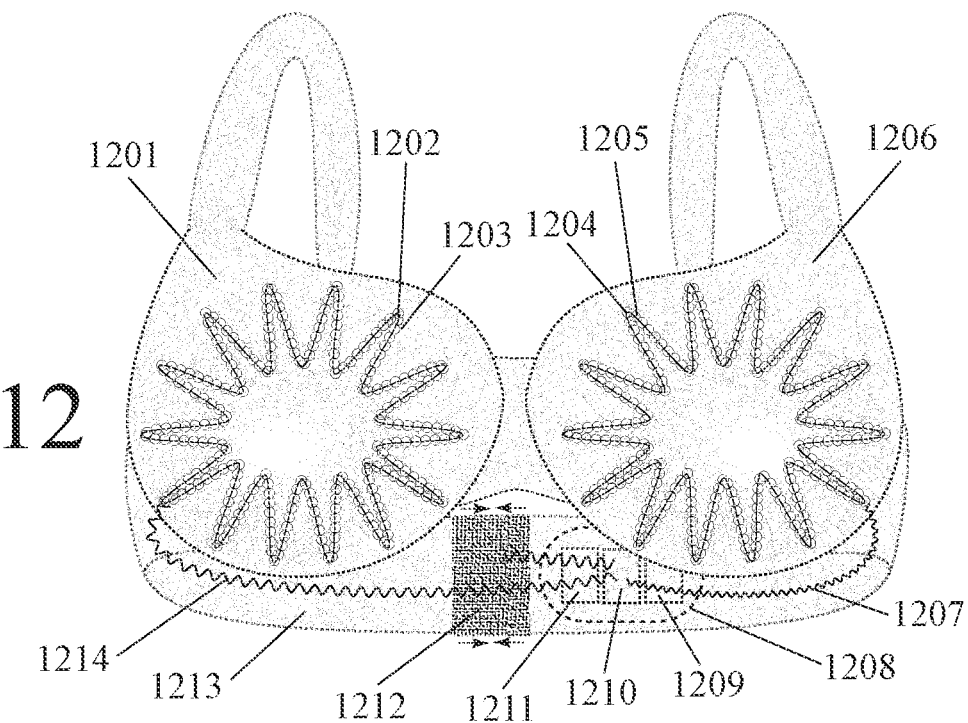
FIG. 12 shows a smart bra with an electromagnetically-contracting back strap.

FIG. 12 shows an example of a smart bra for optical analysis of breast tissue comprising: a garment worn by a person, wherein the garment further comprises; a first cup 1201 worn on the person's right breast, wherein the first cup further comprises an array of light emitters (such as 1202) and light receivers (such as 1203), and wherein light from light emitters received by light receivers is analyzed to create an image of a breast and/or to identify breast tissue composition; a second cup 1206 worn on the person's left breast, wherein the second cup further comprises an array of light emitters (such as 1204) and light receivers (such as 1205), and wherein light from light emitters received by light receivers is analyzed to create an image of a breast and/or to identify breast tissue composition; an electronics housing 1208, wherein the electronics housing further comprises a battery 1210, data processor 1209, and a data transmitter 1211; one or more electromagnetic energy pathways (e.g. undulating wires or conductive threads), 1214 and 1207, between one or more components in the electronics housing and the first and second cups; a back strap 1213 across the person's back; and an electromagnetically-activated contracting portion 1212 of the back strap, wherein contraction of the contracting portion is automatically controlled by the data processor in order to adjust the fit of the garment.

In an example, an electromagnetically-activated contracting portion of a back strap can be piezoelectric. In an example, transmission of electromagnetic energy through the contracting portion can cause that portion to shrink, thereby increasing the tightness of the garment fit. In an example, transmission of electromagnetic energy through the contracting portion can cause that portion to expand, thereby making the garment less tight. In an example, when a contracting portion is activated, it pulls the ends of the back strap together, thereby increasing the tightness of the garment. In an example, the contracting portion can be selectively activated when a garment is to be used for tissue scanning and/or image creation.

In an example, a light emitter can be an LED. In an example, a light emitter can emit near-infrared light and/or coherent light. In an example, a light emitter can emit light at different wavelengths at different times. In an example, different light emitters in a ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing can also be detached from a garment before washing and then reattached after washing.

Figure 13:
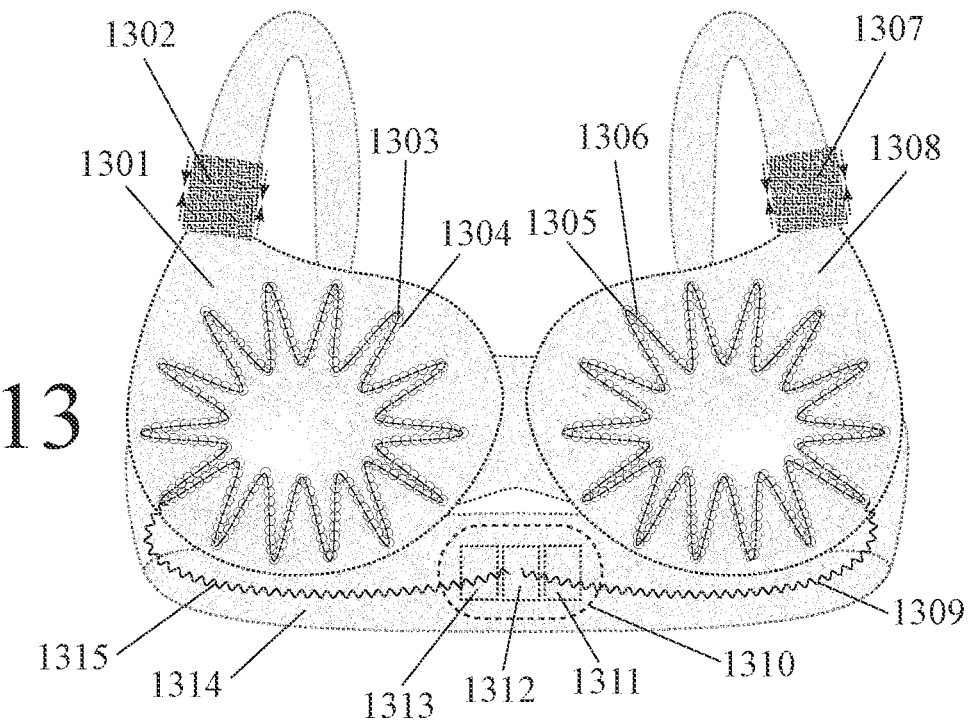
FIG. 13 shows a smart bra with electromagnetically-contracting shoulder straps.

FIG. 13 shows an example of a smart bra for optical analysis of breast tissue comprising: a garment worn by a person, wherein the garment further comprises; a first cup 1301 worn on the person's right breast, wherein the first cup further comprises an array of light emitters (such as 1303) and light receivers (such as 1304), and wherein light from light emitters received by light receivers is analyzed to create an image of a breast and/or to identify breast tissue composition; a second cup 1308 worn on the person's left breast, wherein the second cup further comprises an array of light emitters (such as 1305) and light receivers (such as 1306), and wherein light from light emitters received by light receivers is analyzed to create an image of a breast and/or to identify breast tissue composition; a back strap 1314 across the person's back; an electronics housing 1310, wherein the electronics housing further comprises a battery 1313, data processor 1312, and a data transmitter 1311; one or more electromagnetic energy pathways (e.g. undulating wires or conductive threads), 1315 and 1309, between one or more components in the electronics housing and the first and second cups; a first electromagnetically-activated contracting portion 1302 on a first shoulder strap; and a second electromagnetically-activated contracting portion 1307 on a second shoulder strap, wherein contractions of the first and second contracting portions are automatically controlled by the data processor in order to adjust the fit of the garment.

In an example, an electromagnetically-activated contracting portion can be piezoelectric. In an example, transmission of electromagnetic energy through a contracting portion can cause that portion to shrink, thereby increasing the tightness of the garment fit. In an example, transmission of electromagnetic energy through a contracting portion can cause that portion to expand, thereby making the garment less tight. In an example, contracting portions can be selectively activated when a garment is to be used for tissue scanning and/or image creation.

In an example, a light emitter can be an LED. In an example, a light emitter can emit near-infrared light and/or coherent light. In an example, a light emitter can emit light at different wavelengths at different times. In an example, different light emitters in a ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing can also be detached from a garment before washing and then reattached after washing.

Figure 14:
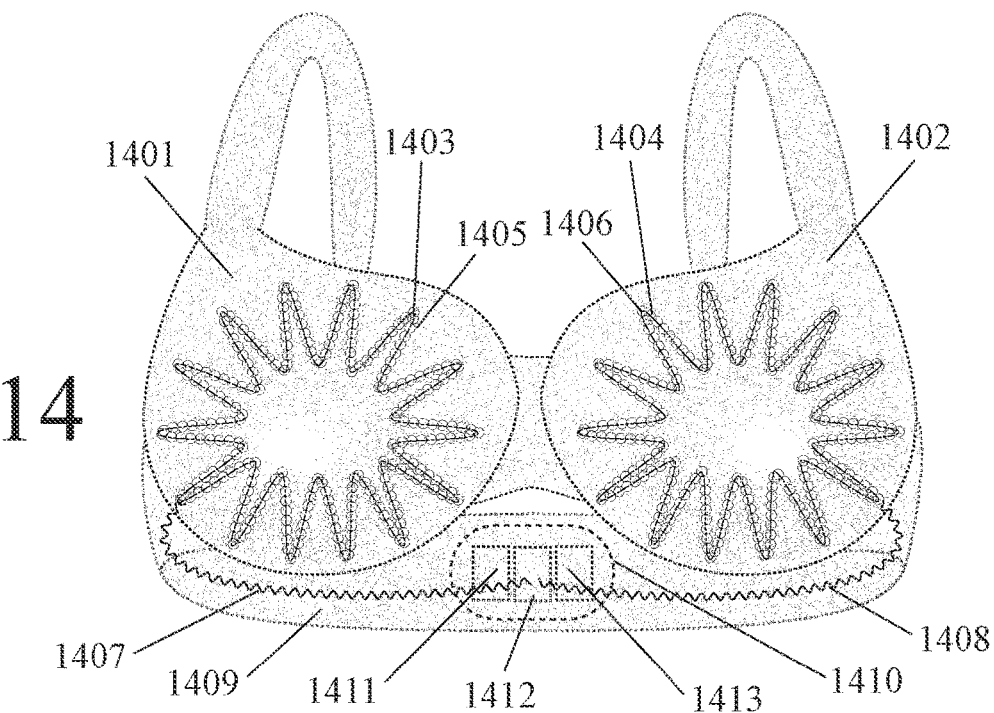
FIG. 14 shows a smart bra with conductive sinusoidal rings with light emitters and receivers.

FIG. 14 shows an example of a smart bra for optical analysis of breast tissue comprising: a garment worn by a person, wherein the garment further comprises; a first cup 1401 worn on the person's right breast, wherein the first cup further comprises a conductive sinusoidal ring 1403 which conducts electromagnetic energy and a sinusoidal ring 1405 of light emitters and light receivers which are connected to the conductive sinusoidal ring, and wherein light from light emitters received by light receivers is analyzed to create an image of a breast and/or to identify breast tissue composition; a second cup 1402 worn on the person's left breast, wherein the second cup further comprises a conductive sinusoidal ring 1406 which conducts electromagnetic energy and a sinusoidal ring 1404 of light emitters and light receivers which are connected to the conductive sinusoidal ring, and wherein light from light emitters received by light receivers is analyzed to create an image of a breast and/or to identify breast tissue composition; a back strap 1409 across the person's back; an electronics housing 1410, wherein the electronics housing further comprises a battery 1411, data processor 1412, and a data transmitter 1413; and one or more electromagnetic energy pathways (e.g. undulating wires or conductive threads), 1407 and 1408, between one or more components in the electronics housing and the first and second cups.

In an example, a sinusoidal ring can be created by applying sinusoidal oscillations to a circle, oval, or ellipse. In an example, a sinusoidal ring can have four undulations. In an example, a sinusoidal ring can have five undulations (e.g. a rounded five-pointed-star shape). In an example, a sinusoidal ring can have six undulations (e.g. a rounded six-pointed-star shape). In an example, a sinusoidal ring can have eight or more undulations.

In an example, a light emitter can be an LED which emits near-infrared light and/or coherent light. In an example, a light emitter can emit light at different wavelengths at different times. In an example, different light emitters in a ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 15:
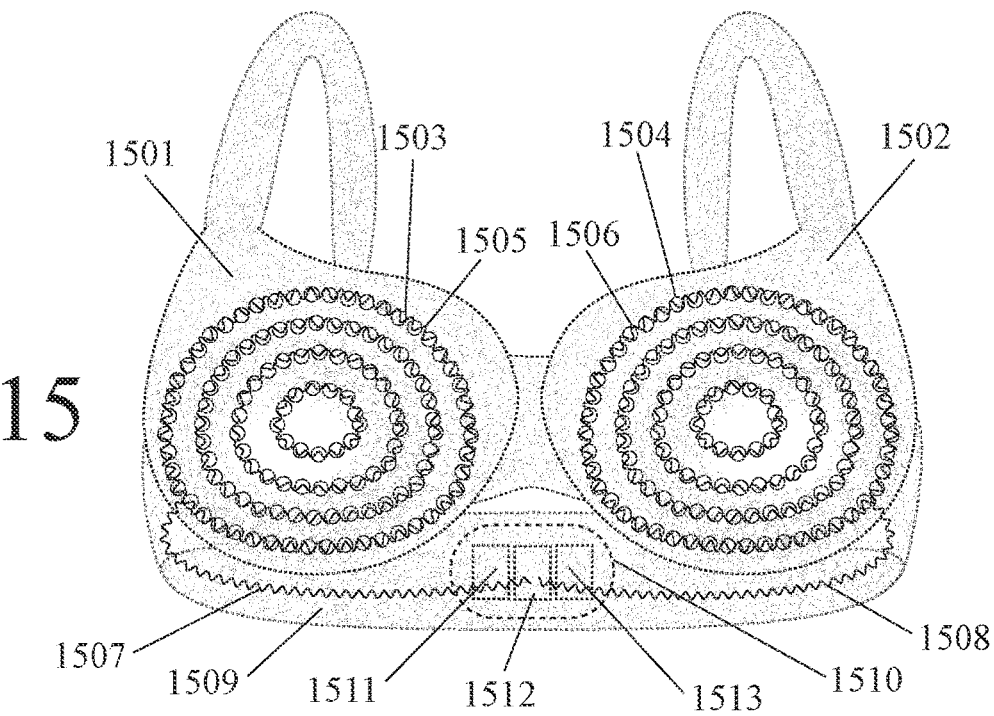
FIG. 15 shows a smart bra with nested conductive rings with light emitters and receivers.

FIG. 15 shows an example of a smart bra for optical analysis of breast tissue comprising: a garment worn by a person, wherein the garment further comprises; a first cup 1501 worn on the person's right breast, wherein the first cup further comprises a plurality of nested conductive rings (including 1505), wherein there are a plurality of light emitters and light receivers (including 1503) on each conductive ring, and wherein light from light emitters received by light receivers is analyzed to create an image of a breast and/or to identify breast tissue composition; a second cup 1502 worn on the person's left breast, wherein the second cup further comprises a plurality of nested conductive rings (including 1506), wherein there are a plurality of light emitters and light receivers (including 1504) on each conductive ring, and wherein light from light emitters received by light receivers is analyzed to create an image of a breast and/or to identify breast tissue composition; a back strap 1509 across the person's back; an electronics housing 1510, wherein the electronics housing further comprises a battery 1511, data processor 1512, and a data transmitter 1513; and one or more electromagnetic energy pathways (e.g. undulating wires or conductive threads), 1507 and 1508, between one or more components in the electronics housing and the first and second cups.

In an example, a ring can be circular, oval, or elliptical. In an example, a conductive ring can be made with an undulating (e.g. sinusoidal) wire. In an example, a conductive ring can be made with a conductive thread or yarn. In an example, a conductive ring can be made with an elastomeric (silicone-based) polymer which has been coated, impregnated, or doped with conductive particles. In an example, there can be four rings in a plurality of nested conductive rings. In an example, there can be five rings in a plurality of nested conductive rings. In an example, there can be six or more rings in a plurality of nested conductive rings. In an example, nested conductive rings can be concentric as well as nested.

In an example, a ring may have only light emitters or light receivers. In an example, there can be an alternating sequence of rings with light emitters and rings with light receivers, as one moves away from the center of a cup. In an example, rings which are closer to the center of the cup can be closer together than rings which are farther from the center of the cup. In an example, rings which are closer to the center of the cup can be farther apart than rings which are farther from the center of the cup. In an example, a ring may have a combination of light emitters and light receivers. In an example, a ring may have an alternating sequence of light emitters and light receivers around its circumference. In an example light emitters and/or light receivers on rings which are closer to the center of the cup can be closer together than those on rings which are farther from the center of the cup. In an example light emitters and/or light receivers on rings which are closer to the center of the cup can be farther apart than those on rings which are farther from the center of the cup.

In an example, a light emitter can be an LED which emits near-infrared light and/or coherent light. In an example, a light emitter can emit light at different wavelengths at different times. In an example, different light emitters in a ring can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 16:
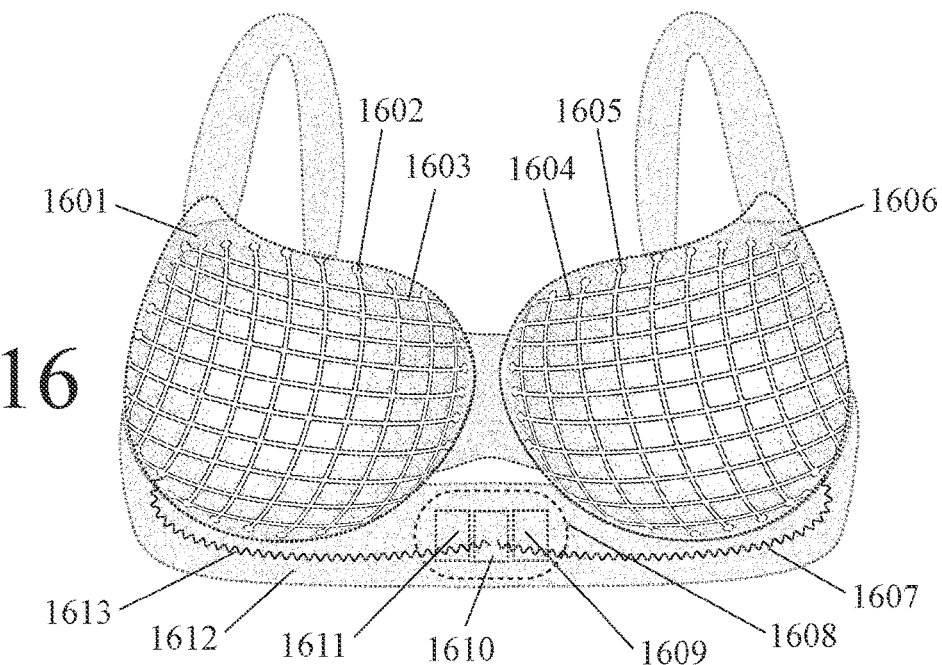
FIG. 16 shows a smart bra with a quadrilateral grid of optical fibers.

FIG. 16 shows an example of a smart bra for optical analysis of breast tissue comprising: a garment worn by a person, wherein the garment further comprises; a first cup 1601 worn on the person's right breast, wherein the first cup further comprises a grid (or array) of optical fibers (including 1603) which are in optical communication with light emitters (including 1602), and wherein changes in light emitted from the optical fibers caused by that light traveling through breast tissue are analyzed as part of the creation of an image of a breast and/or identification of breast tissue composition; a second cup 1606 worn on the person's left breast, wherein the second cup further comprises a grid (or array) of optical fibers (including 1604) which are in optical communication with light emitters (including 1605), and wherein changes in light emitted from the optical fibers caused by that light traveling through breast tissue are analyzed as part of the creation of an image of a breast and/or identification of breast tissue composition; a back strap 1612 across the person's back; an electronics housing 1608, wherein the electronics housing further comprises a battery 1611, data processor 1610, and a data transmitter 1609; and one or more electromagnetic energy pathways (e.g. undulating wires or conductive threads), 1613 and 1607, between one or more components in the electronics housing and the first and second cups.

In an example, two or more light emitters which are in optical communication with two or more intersecting (or overlapping) optical fibers can be activated simultaneously, resulting in light emission from the intersection of the two or more optical fibers. In an example, a grid of optical fibers can have quadrilateral openings or gaps between fibers. In an example, a grid of optical fibers can have hexagonal openings or gaps between fibers. In an example, a proximal end of an optical fiber in a grid (or array) of optical fibers can be defined as the end which is closest to a light emitter and a distal end of the optical fiber can be defined as the end which is farthest from the light emitter. In an example, the distal end of an optical fiber can curve toward the surface of a breast. In an example, the distal end of an optical fiber can be substantially perpendicular to the surface of a breast.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 17:
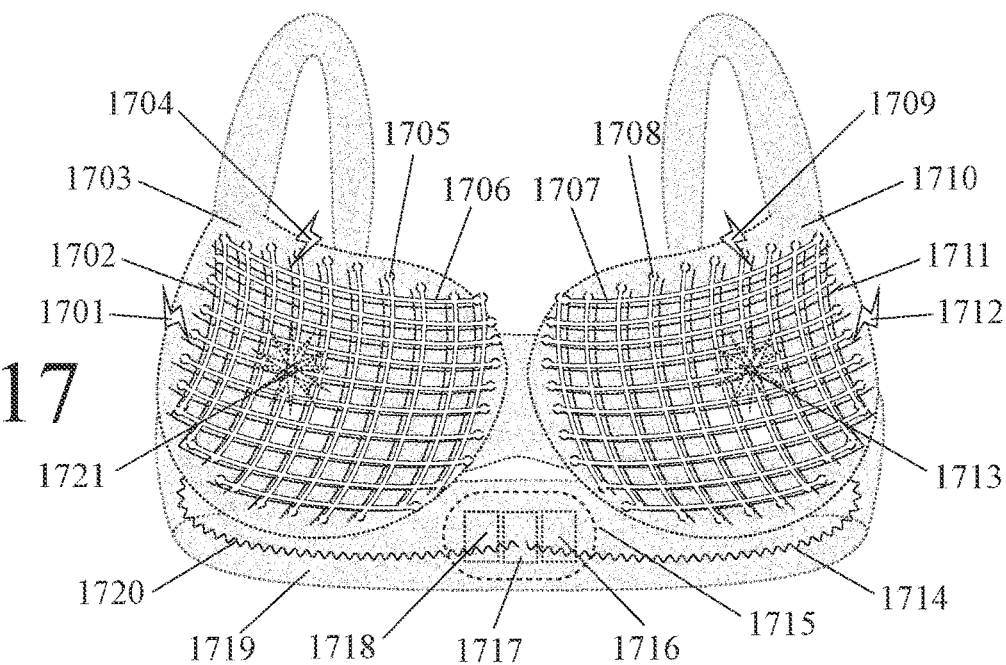
FIG. 17 shows a smart bra with an electroconductive grid and micromirrors.

FIG. 17 shows an example of a smart bra for optical analysis of breast tissue comprising: a garment worn by a person, wherein the garment further comprises; a first cup 1703 worn on the person's right breast, wherein the first cup further comprises a grid of optical fibers (including 1706) which are in optical communication with light emitters (including 1705), wherein the first cup further comprises a grid of electroconductive pathways (including 1702), wherein application of electromagnetic energy (1701 and 1704) via two electroconductive pathways moves a micromirror at the intersection of two optical fibers which causes light emission 1721 from that intersection, and wherein changes in this light caused by travel through breast tissue are analyzed as part of the creation of an image of a breast and/or identification of breast tissue composition; a second cup 1710 worn on the person's left breast, wherein the second cup further comprises a grid of optical fibers (including 1707) which are in optical communication with light emitters (including 1708), wherein the second cup further comprises a grid of electroconductive pathways (including 1711), wherein application of electromagnetic energy (1709 and 1712) via two electroconductive pathways moves a micromirror at the intersection of two optical fibers which causes light emission 1713 from that intersection, and wherein changes in this light caused by travel through breast tissue are analyzed as part of the creation of an image of a breast and/or identification of breast tissue composition; a back strap 1719 across the person's back; an electronics housing 1715, wherein the electronics housing further comprises a battery 1718, data processor 1717, and a data transmitter 1716; and one or more electromagnetic energy pathways (e.g. undulating wires or conductive threads), 1720 and 1714, between one or more components in the electronics housing and the first and second cups.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

FIG. 18 shows an example of a smart bra for optical analysis of breast tissue comprising: a garment worn by a person, wherein the garment further comprises; a first cup 1801 worn on the person's right breast, wherein the first cup further comprises a spiral (or helical) array of light emitters and light receivers (including 1802) connected to electromagnetic pathways (e.g. wires or conductive threads) 1803, and wherein light from light emitters received by light receivers is analyzed to create an image of a breast and/or to identify breast tissue composition; a second cup 1806 worn on the person's left breast, wherein the second cup further comprises a spiral (or helical) array of light emitters and light receivers (including 1805) connected to electromagnetic pathways (e.g. wires or conductive threads) 1804, and wherein light from light emitters received by light receivers is analyzed to create an image of a breast and/or to identify breast tissue composition; a back strap 1812 across the person's back; an electronics housing 1808, wherein the electronics housing further comprises a battery 1811, data processor 1810, and a data transmitter 1809; and one or more electromagnetic energy pathways (e.g. undulating wires or conductive threads), 1813 and 1807, between one or more components in the electronics housing and the first and second cups.

In an example, a light emitter can be an LED which emits near-infrared light and/or coherent light. In an example, a light emitter can emit light at different wavelengths at different times. In an example, different light emitters in a spiral can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

FIG. 19 shows an example of a smart bra for optical analysis of breast tissue comprising: a garment worn by a person, wherein the garment further comprises; a first cup 1901 worn on the person's right breast, wherein the first cup further comprises a sunburst array of radial spokes with light emitters and light receivers (including 1902) connected by electromagnetic pathways (including 1903) such as wires or conductive threads, and wherein light from light emitters received by light receivers is analyzed to create an image of a breast and/or to identify breast tissue composition; a second cup 1906 worn on the person's left breast, wherein the second cup further comprises a sunburst array of radial spokes with light emitters and light receivers (including 1905) connected by electromagnetic pathways (including 1904) such as wires or conductive threads, and wherein light from light emitters received by light receivers is analyzed to create an image of a breast and/or to identify breast tissue composition; a back strap 1912 across the person's back; an electronics housing 1908, wherein the electronics housing further comprises a battery 1911, data processor 1910, and a data transmitter 1909; and one or more electromagnetic energy pathways (e.g. undulating wires or conductive threads), 1913 and 1907, between one or more components in the electronics housing and the first and second cups.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 20:
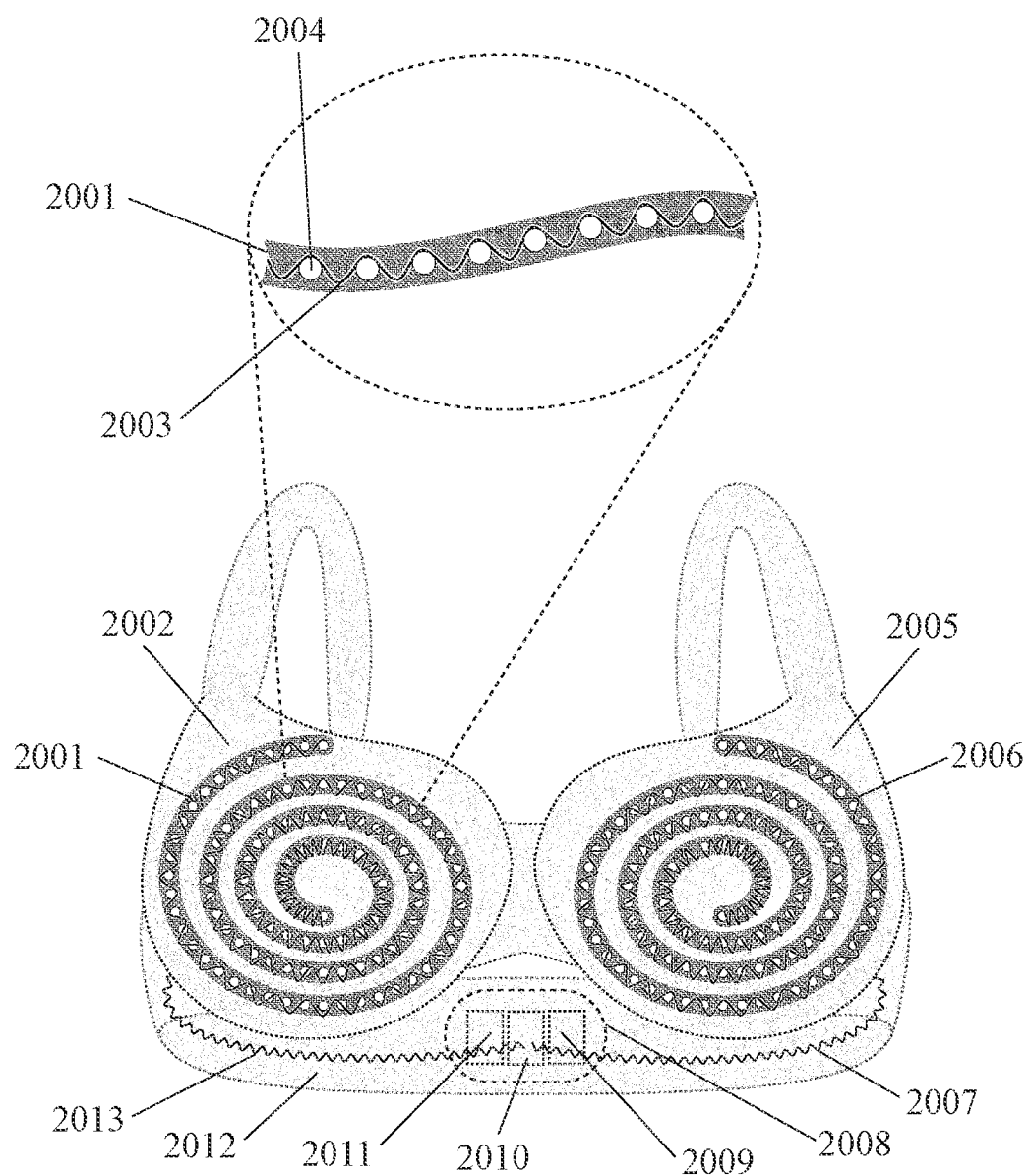
FIG. 20 shows a smart bra with a flexible or elastic strip, an undulating wire or conductive thread, and a series of light emitters and receivers.

FIG. 20 shows an example of a smart bra for optical analysis of breast tissue comprising: a garment worn by a person, wherein the garment further comprises; a first cup 2002 worn on the person's right breast, wherein the first cup further comprises a flexible and/or elastic strip 2001 with a longitudinal electroconductive pathway (e.g. an undulating wire or conductive thread) 2003 and a longitudinal series of light emitters and light receivers (including 2004), wherein the flexible and/or elastic strip is in a spiral (or helical) configuration on the first cup, and wherein light from the light emitters received by the light receivers is analyzed to create an image of a breast and/or to identify breast tissue composition; a second cup 2005 worn on the person's left breast, wherein the second cup further comprises a flexible and/or elastic strip 2006 with a longitudinal electroconductive pathway (e.g. an undulating wire or conductive thread) and a longitudinal series of light emitters and light receivers, wherein the flexible and/or elastic strip is in a spiral (or helical) configuration on the second cup, and wherein light from the light emitters received by the light receivers is analyzed to create an image of a breast and/or to identify breast tissue composition; a back strap 2012 across the person's back; an electronics housing 2008, wherein the electronics housing further comprises a battery 2011, data processor 2010, and a data transmitter 2009; and one or more electromagnetic energy pathways (e.g. undulating wires or conductive threads), 2013 and 2007, between one or more components in the electronics housing and the first and second cups.

The dotted oval in the upper portion of FIG. 20 provides a close-up view of the flexible and/or elastic strip with the longitudinal series of light emitters and light receivers. In an example, this flexible and/or elastic strip can be sewn into a cup in a spiral (or helical) configuration. In an example, light emitters in such a spiral or helix can be activated at different times in a spiral or helical sequence. In an example, a longitudinal series on a flexible and/or elastic strip can comprise an alternating sequence of light emitters and light receivers.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 21:
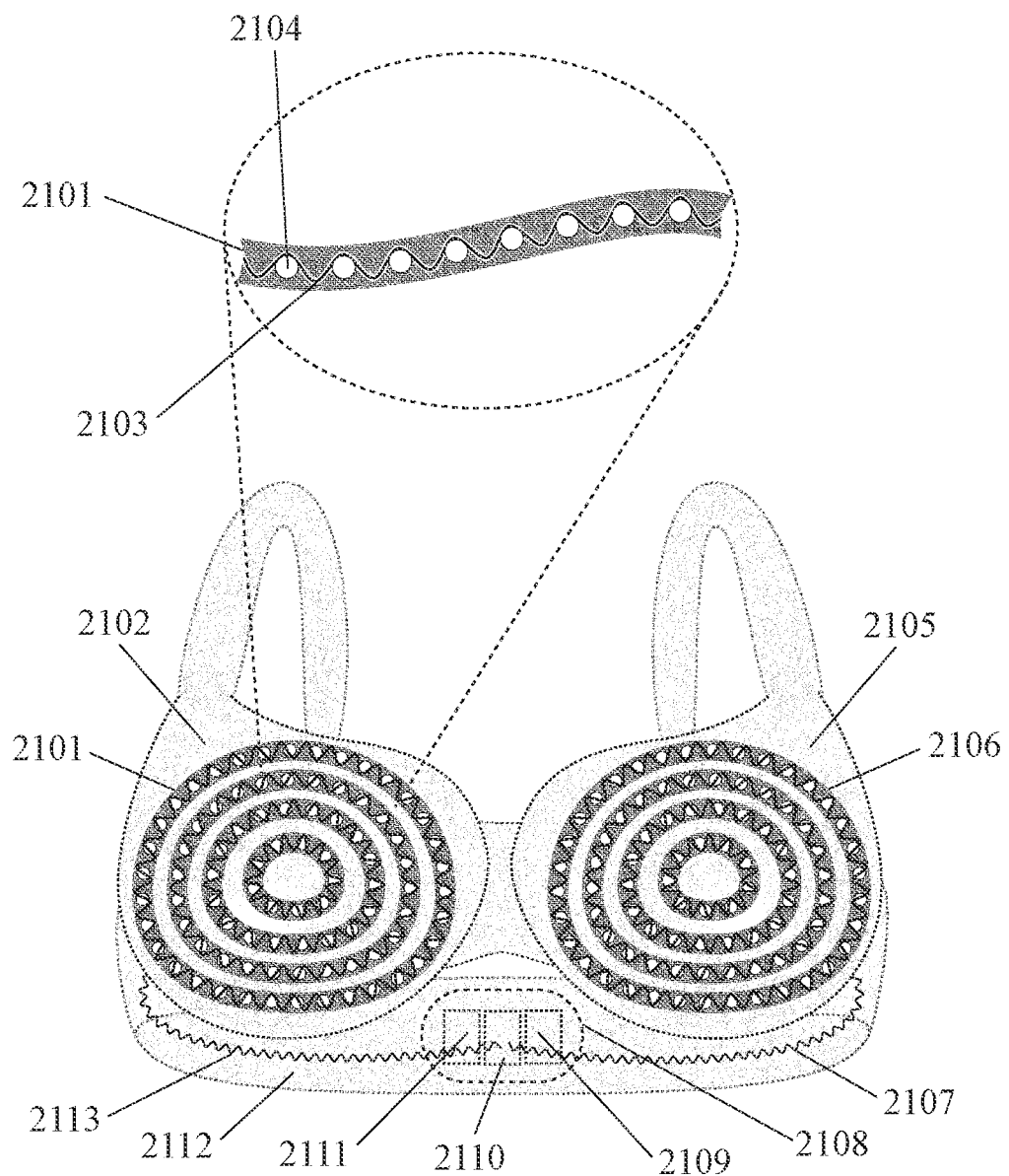
FIG. 21 shows a smart bra with flexible or elastic strips configured in nested rings, undulating wires or conductive threads, and light emitters and receivers.

FIG. 21 shows an example of a smart bra for optical analysis of breast tissue comprising: a garment worn by a person, wherein the garment further comprises; a first cup 2102 worn on the person's right breast, wherein the first cup further comprises flexible and/or elastic strips including 2101 with longitudinal electroconductive pathways (e.g. undulating wires or conductive threads) including 2103 and longitudinal series of light emitters and light receivers including 2104, wherein flexible and/or elastic strips are configured in nested rings on the first cup, and wherein light from the light emitters received by the light receivers is analyzed to create an image of a breast and/or to identify breast tissue composition; a second cup 2105 worn on the person's left breast, wherein the second cup further comprises flexible and/or elastic strips including 2106 with longitudinal electroconductive pathways (e.g. undulating wires or conductive threads) and longitudinal series of light emitters and light receivers, wherein flexible and/or elastic strips are configured in nested rings on the second cup, and wherein light from the light emitters received by the light receivers is analyzed to create an image of a breast and/or to identify breast tissue composition; a back strap 2112 across the person's back; an electronics housing 2108, wherein the electronics housing further comprises a battery 2111, data processor 2110, and a data transmitter 2109; and one or more electromagnetic energy pathways (e.g. undulating wires or conductive threads), 2113 and 2107, between one or more components in the electronics housing and the first and second cups.

The dotted oval in the upper portion of FIG. 21 provides a close-up view of one of flexible and/or elastic strips with a longitudinal series of light emitters and light receivers. In an example, flexible and/or elastic strips can be sewn into a cup in a plurality of (concentric) nested rings. In an example, light emitters on a ring can be activated at different times in a clockwise (or counterclockwise) sequence. In an example, a ring can comprise an alternating sequence of light emitters and light receivers.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 22:
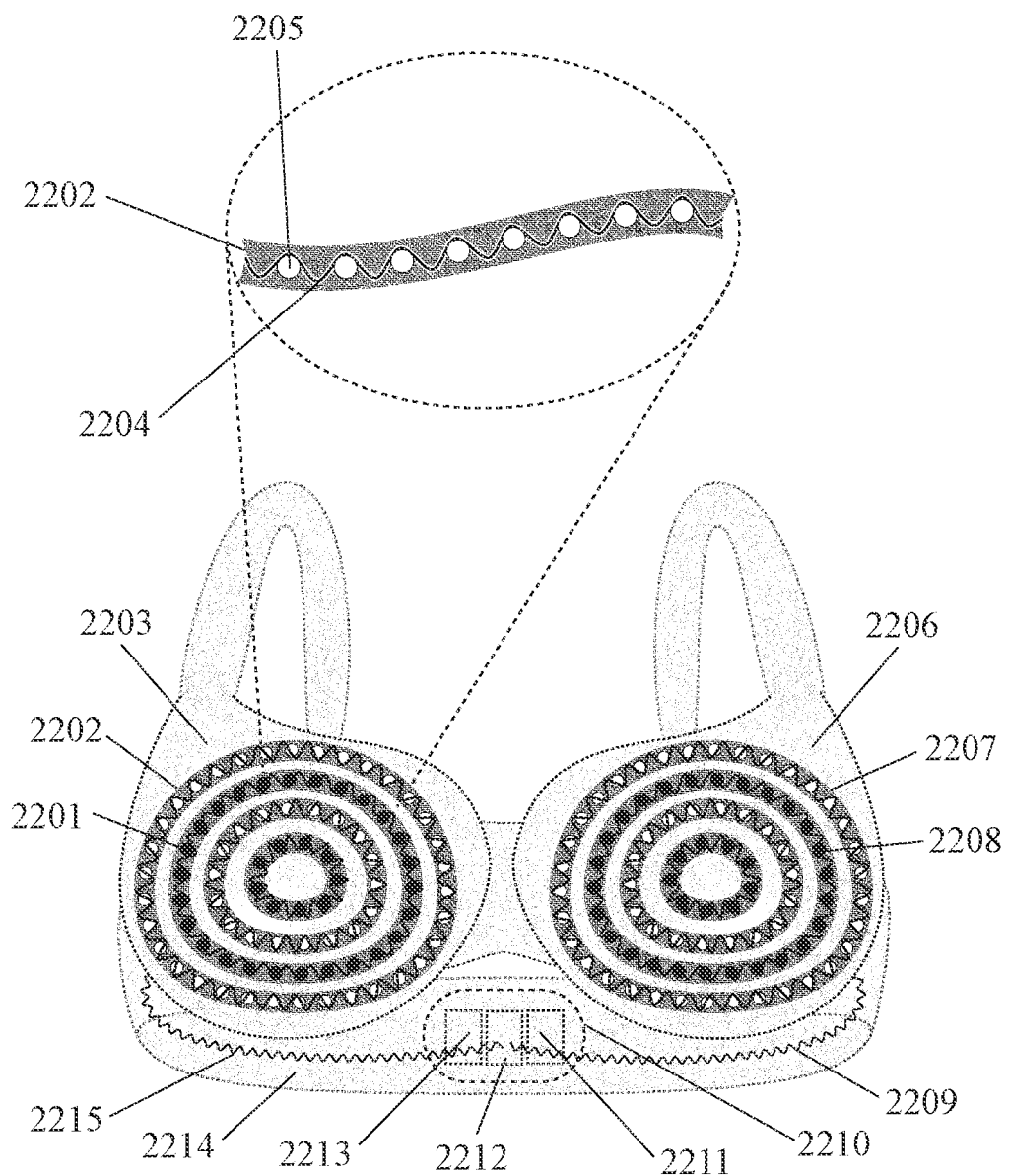
FIG. 22 shows a smart bra with flexible or elastic strips configured in nested rings, undulating wires or conductive threads, with light emitters on some rings and light receivers on other rings.

FIG. 22 shows an example of a smart bra for optical analysis of breast tissue comprising: a garment worn by a person, wherein the garment further comprises; a first cup 2203 worn on the person's right breast, wherein the first cup further comprises flexible and/or elastic strips including 2202 with longitudinal electroconductive pathways (e.g. undulating wires or conductive threads) including 2204 and longitudinal series of light emitters 2205 and light receivers including 2201, wherein flexible and/or elastic strips are configured in nested rings on the first cup, and wherein light from the light emitters received by the light receivers is analyzed to create an image of a breast and/or to identify breast tissue composition; a second cup 2206 worn on the person's left breast, wherein the second cup further comprises flexible and/or elastic strips including 2207 with longitudinal electroconductive pathways (e.g. undulating wires or conductive threads) and longitudinal series of light emitters and light receivers 2208, wherein flexible and/or elastic strips are configured in nested rings on the second cup, and wherein light from the light emitters received by the light receivers is analyzed to create an image of a breast and/or to identify breast tissue composition; a back strap 2214 across the person's back; an electronics housing 2210, wherein the electronics housing further comprises a battery 2213, data processor 2212, and a data transmitter 2211; and one or more electromagnetic energy pathways (e.g. undulating wires or conductive threads), 2215 and 2209, between one or more components in the electronics housing and the first and second cups.

The dotted oval in the upper portion of FIG. 21 provides a close-up view of one of flexible and/or elastic strips with a longitudinal series of light emitters or light receivers. In an example, flexible and/or elastic strips can be sewn into a cup in a plurality of (concentric) nested rings. In an example, light emitters on a ring can be activated at different times in a clockwise (or counterclockwise) sequence. In an example, a first ring can comprise only light emitters and a second ring can comprise only light receivers. In an example, a plurality of nested rings can alternate between rings with light emitters and rings with light receivers as one moves away from the center of the cup. In an example, rings which are farther from the center of the cup can have a greater number of light emitters or light receivers than rings which are closer to the center of the cup. In an example, light emitters and light receivers can be arranged in a hub-and-spoke configuration in the plurality of nested rings.

In an example, a light emitter can be an LED which emits near-infrared light and/or coherent light. In an example, a light emitter can emit light at different wavelengths at different times. In an example, different light emitters can emit light at different wavelengths. In an example, a light emitter can be positioned so as to emit light along a vector which is: substantially perpendicular to a breast surface; directed toward a breast centroid; and/or directed toward a particular light receiver. In an example, light from a light emitter can be received by multiple light emitters after diffusion through breast tissue. In an example, data from a garment can be used to create an image of a breast and/or to analyze the composition of breast tissue. In an example, data from a garment can be used to identify the presence and/or location of (potentially) malignant tissue. In an example, an electronics housing and/or an array of light emitters and receivers can be detached from a garment before washing and then reattached after washing.

Figure 23:
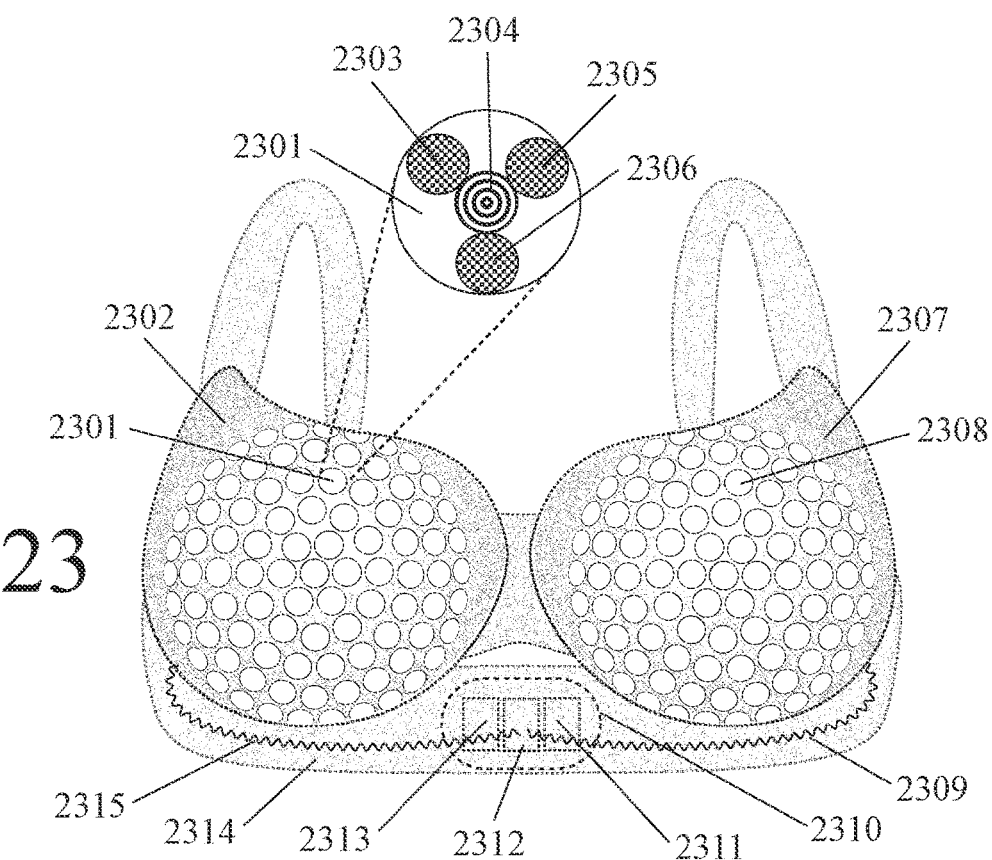
FIG. 23 shows a smart bra with a concave array of imaging components, wherein each component has three light emitters and one light receiver.

FIG. 23 shows an example of a smart bra for optical analysis of breast tissue comprising: a garment worn by a person, wherein the garment further comprises; a first cup 2302 worn on the person's right breast, wherein the first cup further comprises a concave array of imaging components including 2301, wherein each imaging component includes three light emitters (2303, 2305, and 2306) and a light receiver 2304, and wherein light from the light emitters received by the light receiver is analyzed as part of the creation of an image of a breast and/or identification of breast tissue composition; a second cup 2307 worn on the person's left breast, wherein the second cup further comprises a concave array of imaging components including 2308, wherein each imaging component includes three light emitters and a light receiver, and wherein light from the light emitters received by the light receiver is analyzed as part of the creation of an image of a breast and/or identification of breast tissue composition; a back strap 2314 across the person's back; an electronics housing 2310, wherein the electronics housing further comprises a battery 2312, data processor 2311, and a data transmitter 2313; and one or more electromagnetic energy pathways (e.g. undulating wires or conductive threads), 2315 and 2309, between one or more components in the electronics housing and the first and second cups. The dotted oval in the upper portion of FIG. 23 provides a close-up view of one of the imaging components.

In an example, light emitters in an imaging component can all be the same distance from the light receiver. In an example, different light emitters in an imaging component can be different distances from the light receiver. In an example, different light emitters in an imaging component can be at different angles and/or orientations relative to the light receiver. In an example, light emitters in an imaging component can be arranged in a circular array around a light receiver. In an example, light emitters in an imaging component can be arranged in a polygonal array around a light receiver. In an example, different light emitters in an imaging component can emit light at different frequencies. In an example, different light emitters in an imaging component can emit light at different times. In an example, the same light emitter can emit light at different frequencies at different times. In an example, imaging components which are closer to the center of a cup can be closer together than those which are farther from the center of the cup. In an example, imaging components which are father from the center of a cup can be closer together than those which are closer to the center of the cup.

In an example, a light emitter can be an LED which emits near-infrared light and/or coherent light. In an example, a light emitter can emit light along a vector which: perpendicular to a breast surface; toward a breast centroid; and/or toward a particular light receiver. In an example, changes and/or differences in the intensity and/or spectral distribution of light received by light receivers after traveling through breast tissue can be analyzed to create a (3D) image which shows (variation in) breast tissue density and/or composition. In an example, changes and/or differences in the spectrum of light received by light receivers after traveling through breast tissue can be analyzed to identify (potentially) malignant tissue. In an example, data from a garment can be used to create an image of a breast and/or to analyze the composition of breast tissue. In an example, data from a garment can be used to identify the presence and/or location of (potentially) malignant tissue.

Figure 24:
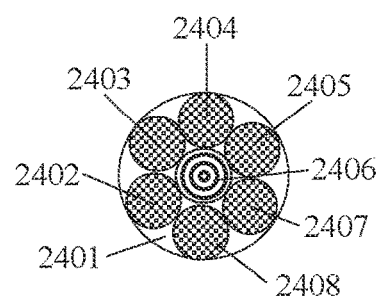
FIG. 24 shows a smart bra with a concave array of imaging components, wherein each component has six light emitters and one light receiver.

FIG. 24 shows another example of an imaging component. This imaging component can be part of a smart bra for optical analysis of breast tissue, like the one which is shown in FIG. 23. In this example, an imaging component 2401 includes six light emitters (2402, 2403, 2404, 2405, 2407, and 2408) around a light receiver 2406. In this example, the six light emitters in the imaging component are all the same distance from the light receiver. In this example, light emitters in the imaging component are in a hexagonal array around a light receiver. In an example, different light emitters in the imaging component can emit light at different frequencies. In an example, different light emitters in the imaging component can emit light at different times. In an example, the same light emitter can emit light at different frequencies at different times.

Figure 25:
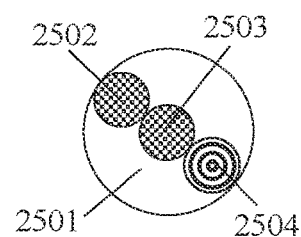
FIG. 25 shows a smart bra with a concave array of imaging components, wherein each component has two light emitters and one light receiver which are collinear.

FIG. 25 shows another example of an imaging component. This imaging component can be part of a smart bra for optical analysis of breast tissue, like the one which is shown in FIG. 23. In this example, an imaging component 2501 includes two light emitters (2502 and 2503) which are different distances from a light receiver 2504. In this example, the two light emitters and the light receiver in the imaging component are located along the same line. In an example, different light emitters in the imaging component can emit light at different frequencies. In an example, different light emitters in the imaging component can emit light at different times. In an example, the same light emitter can emit light at different frequencies at different times.

Figure 26:
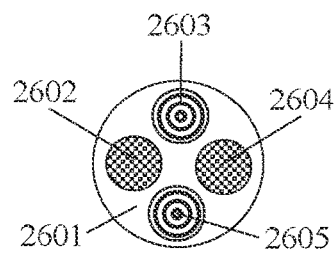
FIG. 26 shows a smart bra with a concave array of imaging components, wherein each component has two light emitters and two light receivers in a polygonal array.

FIG. 26 shows another example of an imaging component. This imaging component can be part of a smart bra for optical analysis of breast tissue, like the one which is shown in FIG. 23. In this example, an imaging component 2601 includes two light emitters (2602 and 2604) and two light receivers (2603 and 2605) in a polygonal array. In this example, the polygonal array is a square, wherein the light emitters are at opposite vertexes in the square. In an example, different light emitters in the imaging component can emit light at different frequencies. In an example, different light emitters in the imaging component can emit light at different times. In an example, the same light emitter can emit light at different frequencies at different times.

Figure 27:
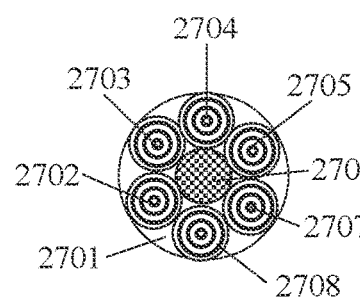
FIG. 27 shows a smart bra with a concave array of imaging components, wherein each component has one light emitter and six light receivers.

FIG. 27 shows another example of an imaging component. This imaging component can be part of a smart bra for optical analysis of breast tissue, like the one which is shown in FIG. 23. In this example, an imaging component 2701 includes six light receivers (2702, 2703, 2704, 2705, 2707, and 2708) around a light emitter 2706. In this example, the six light receivers in the imaging component are all the same distance from the light emitter.

Figure 28:
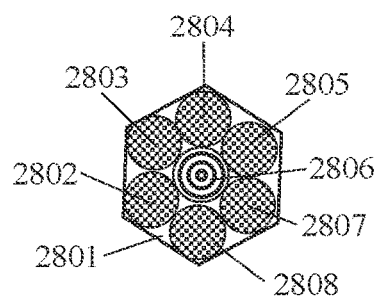
FIG. 28 shows a smart bra with a concave array of hexagonal imaging components, wherein each component has six light emitters and one light receiver.

FIG. 28 shows an example of an imaging component with a hexagonal shape. This hexagonal imaging component can be part of a smart bra for optical analysis of breast tissue, like the one which is shown in FIG. 23. In this example, a hexagonal imaging component 2801 includes six light emitters (2802, 2803, 2804, 2805, 2807, and 2808) around a light receiver 2806. In this example, the six light emitters in the hexagonal imaging component are all the same distance from the light receiver. In this example, light emitters in the hexagonal imaging component are in a hexagonal array around a light receiver. In an example, different light emitters in the hexagonal imaging component can emit light at different frequencies. In an example, different light emitters in the hexagonal imaging component can emit light at different times. In an example, the same light emitter can emit light at different frequencies at different times.

Figure 29:
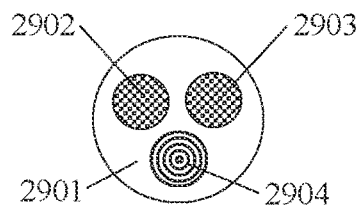
FIG. 29 shows a smart bra with a concave array of imaging components, wherein each component has two light emitters and one light receiver in a triangular array.

FIG. 29 shows another example of an imaging component. This imaging component can be part of a smart bra for optical analysis of breast tissue, like the one which is shown in FIG. 23. In this example, an imaging component 2901 includes two light emitters (2902 and 2903) which are the same distance from a light receiver 2904. In this example, the two light emitters and the one light receiver in the imaging component are located at the vertexes of a (virtual) triangle. In an example, different light emitters in the imaging component can emit light at different frequencies. In an example, different light emitters in the imaging component can emit light at different times. In an example, the same light emitter can emit light at different frequencies at different times.

Figure 30:
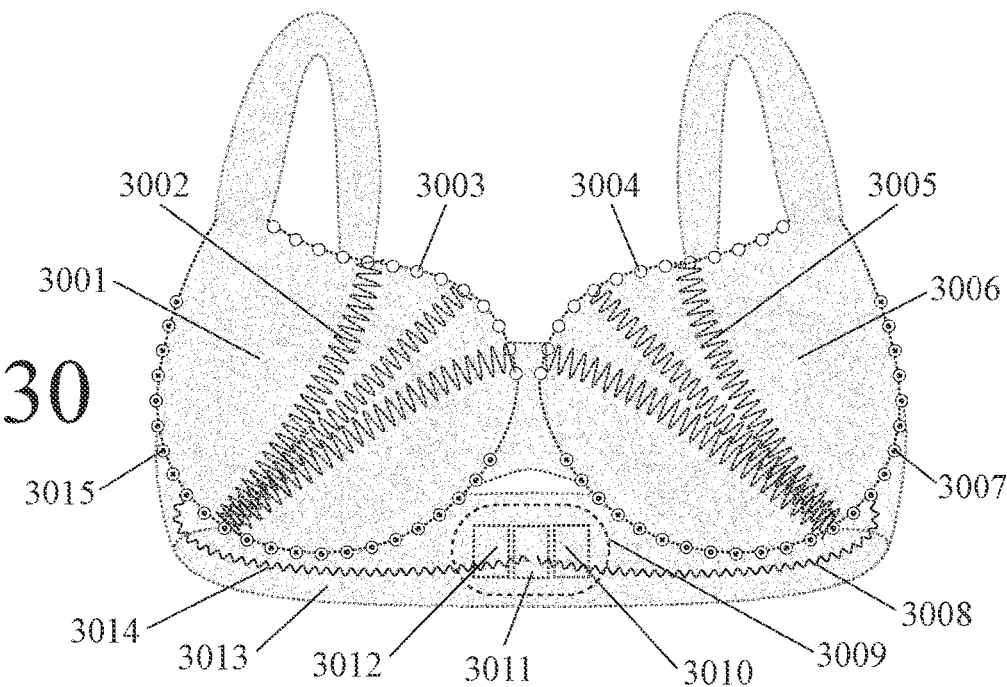
FIG. 30 shows a smart bra with a plurality of light emitters along a first side of a bra cup and a plurality of light receivers along a second side of the cup.

FIG. 30 shows an example of a smart bra for optical analysis of breast tissue comprising: a garment worn by a person, wherein the garment further comprises; a first cup 3001 worn on the person's right breast; a plurality of light emitters (including 3015) along a first side of the first cup and a plurality of light receivers (including 3003) along a second side of the first cup; wherein light rays (3002) emitted from a light receiver on the first side pass through breast tissue and are diffused by the breast tissue before they are received by a plurality of light receivers on the second side, and wherein the light rays received by the plurality of light receivers are analyzed to create an image of a breast and/or to identify breast tissue composition; a second cup 3006 worn on the person's left breast; a plurality of light emitters (including 3007) along a first side of the second cup and a plurality of light receivers (including 3004) along a second side of the second cup; wherein light rays (3005) emitted from a light receiver on the first side pass through breast tissue and are diffused by the breast tissue before they are received by a plurality of light receivers on the second side, and wherein the light rays received by the plurality of light receivers are analyzed to create an image of a breast and/or to identify breast tissue composition; a back strap 3013 across the person's back; an electronics housing 3009, wherein the electronics housing further comprises a battery 3012, a data processor 3011, and a data transmitter 3010; and one or more electromagnetic energy pathways (e.g. undulating wires or conductive threads), 3014 and 3008, between one or more components in the electronics housing and the first and second cups.

In an example, the garment can be a smart bra. In an example, portions of the garment can be made from elastic and/or stretchable material. In an example, there can be a layer of opaque fabric between light emitters and receivers and the outer surface of a cup. In an example, light emitters can be on a right side of a cup and light receivers can be on a left side of the cup, or vice versa. In an example, light emitters can be on an upper portion of a cup and light receivers can be on a lower portion of the cup, or vice versa. In an example, light emitters and light receivers can be distributed around the perimeter of a cup. In an example, light emitters and light receivers can be distributed around the entire concavity of a cup.

In an example, a light emitter can be an LED. In an example, a light emitter can emit near-infrared light. In an example, a light emitter can emit coherent light. In an example, a light emitter can emit light at different wavelengths at different times. In an example, different light emitters can emit light at different wavelengths. In an example, a light emitter can be oriented to emit light along a vector which is substantially perpendicular to a breast surface. In an example, a light emitter can be oriented to emit light toward the center of the breast. In an example, electromagnetic energy can be transmitted to a light emitter through an undulating wire, conductive thread, or conductive yarn. In an example, a garment can comprise elastic and/or stretchable conductive threads or yarns. In an example, a garment can comprise undulating, sinusoidal, and/or zigzagging conductive threads or yarns.

In an example, changes and/or differences in the intensity of light received by light receivers after traveling through breast tissue along different light paths can be analyzed to create a (3D) image which shows (variation in) breast tissue density. In an example, changes and/or differences in the spectrum of light received by light receivers after traveling through breast tissue along different light paths can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap. In an example, an electronics housing can be removably attached to a front of portion of a garment. In an alternative example, a battery, data processor, or data transmitter can be part of a garment at a location other than inside the electronics housing. In an example, an electronics housing can be removed from a garment before a garment is washed and reattached after washing. In an example, an electronics housing can fit into a pocket in a garment and be removed from the pocket before the garment is washed. In an example, an array of light emitters can be removed from a garment before the garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 31:
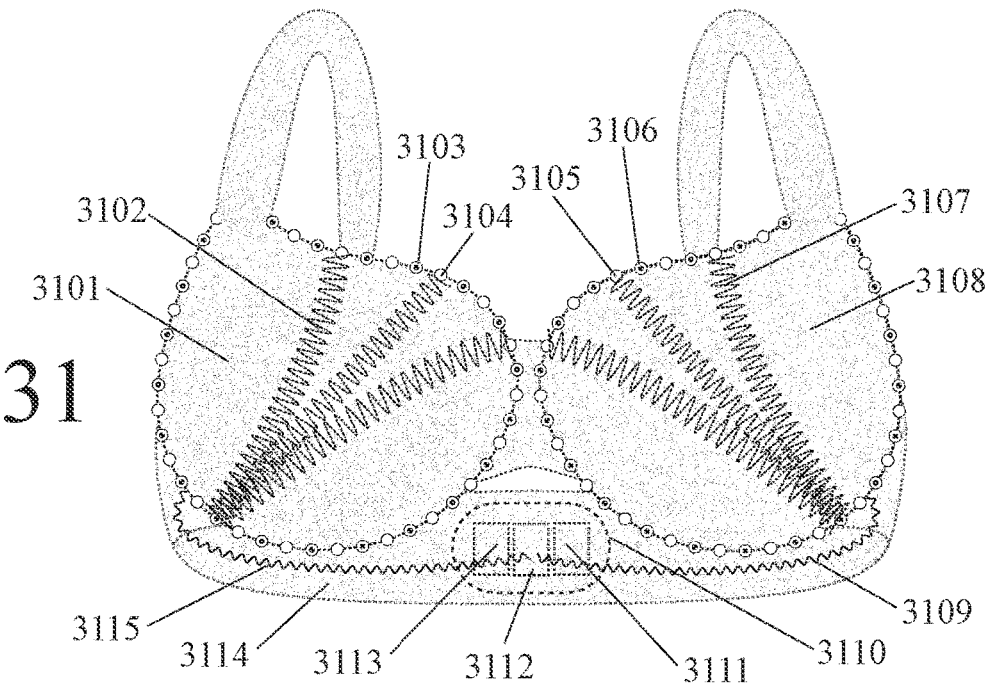
FIG. 31 shows a smart bra with an alternating sequence of light emitters and receivers around the perimeter of bra cup.

FIG. 31 shows an example of a smart bra for optical analysis of breast tissue comprising: a garment worn by a person, wherein the garment further comprises; a first cup 3101 worn on the person's right breast; an alternating sequence of light emitters (including 3103) and light receivers (including 3104) around the perimeter of the first cup; wherein light rays (3102) emitted from a light receiver pass through breast tissue and are diffused by the breast tissue before they are received by a plurality of light receivers, and wherein the light rays received by the plurality of light receivers are analyzed to create an image of a breast and/or to identify breast tissue composition; a second cup 3108 worn on the person's left breast; an alternating sequence of light emitters (including 3106) and light receivers (including 3105) around the perimeter of the second cup; wherein light rays (3107) emitted from a light receiver pass through breast tissue and are diffused by the breast tissue before they are received by a plurality of light receivers, and wherein the light rays received by the plurality of light receivers are analyzed to create an image of a breast and/or to identify breast tissue composition; a back strap 3114 across the person's back; an electronics housing 3110, wherein the electronics housing further comprises a battery 3113, a data processor 3112, and a data transmitter 3111; and one or more electromagnetic energy pathways (e.g. undulating wires or conductive threads), 3115 and 3109, between one or more components in the electronics housing and the first and second cups.

In an example, the garment can be a smart bra. In an example, portions of the garment can be made from elastic and/or stretchable material. In an example, there can be a layer of opaque fabric between light emitters and receivers and the outer surface of a cup. In an example, light emitters and light receivers can be distributed around the outer perimeter of a cup. In an example, light emitters and light receivers can be distributed around the concave surface of a cup.

In an example, a light emitter can be an LED. In an example, a light emitter can emit near-infrared light. In an example, a light emitter can emit coherent light. In an example, a light emitter can emit light at different wavelengths at different times. In an example, different light emitters can emit light at different wavelengths. In an example, a light emitter can be oriented to emit light along a vector which is substantially perpendicular to a breast surface. In an example, a light emitter can be oriented to emit light toward the center of the breast. In an example, electromagnetic energy can be transmitted to a light emitter through an undulating wire, conductive thread, or conductive yarn. In an example, a garment can comprise elastic and/or stretchable conductive threads or yarns. In an example, a garment can comprise undulating, sinusoidal, and/or zigzagging conductive threads or yarns.

In an example, changes and/or differences in the intensity of light received by light receivers after traveling through breast tissue along different light paths can be analyzed to create a (3D) image which shows (variation in) breast tissue density. In an example, changes and/or differences in the spectrum of light received by light receivers after traveling through breast tissue along different light paths can be analyzed to create a (3D) image which shows (variation in) breast tissue composition. In an example, changes and/or differences in the spectrum of light received by light receivers after traveling through breast tissue can be analyzed to identify (potentially) malignant tissue.

In an example, an electronics housing can be removably attached to a back strap. In an example, an electronics housing can be removably attached to a front of portion of a garment. In an alternative example, a battery, data processor, or data transmitter can be part of a garment at a location other than inside the electronics housing. In an example, an electronics housing can be removed from a garment before a garment is washed and reattached after washing. In an example, an electronics housing can fit into a pocket in a garment and be removed from the pocket before the garment is washed. In an example, an array of light emitters can be removed from a garment before the garment is washed and reattached after washing. In an example, a data transmitter can be in wireless communication with a cell phone, smart watch, smart glasses, tablet computer, or laptop computer. In an example, data from a garment can be used to create an image of a breast and/or analyze the composition of breast tissue. In an example, data from a garment can be used to identify the presence and/or location of (potentially) malignant tissue.

Figure 32:
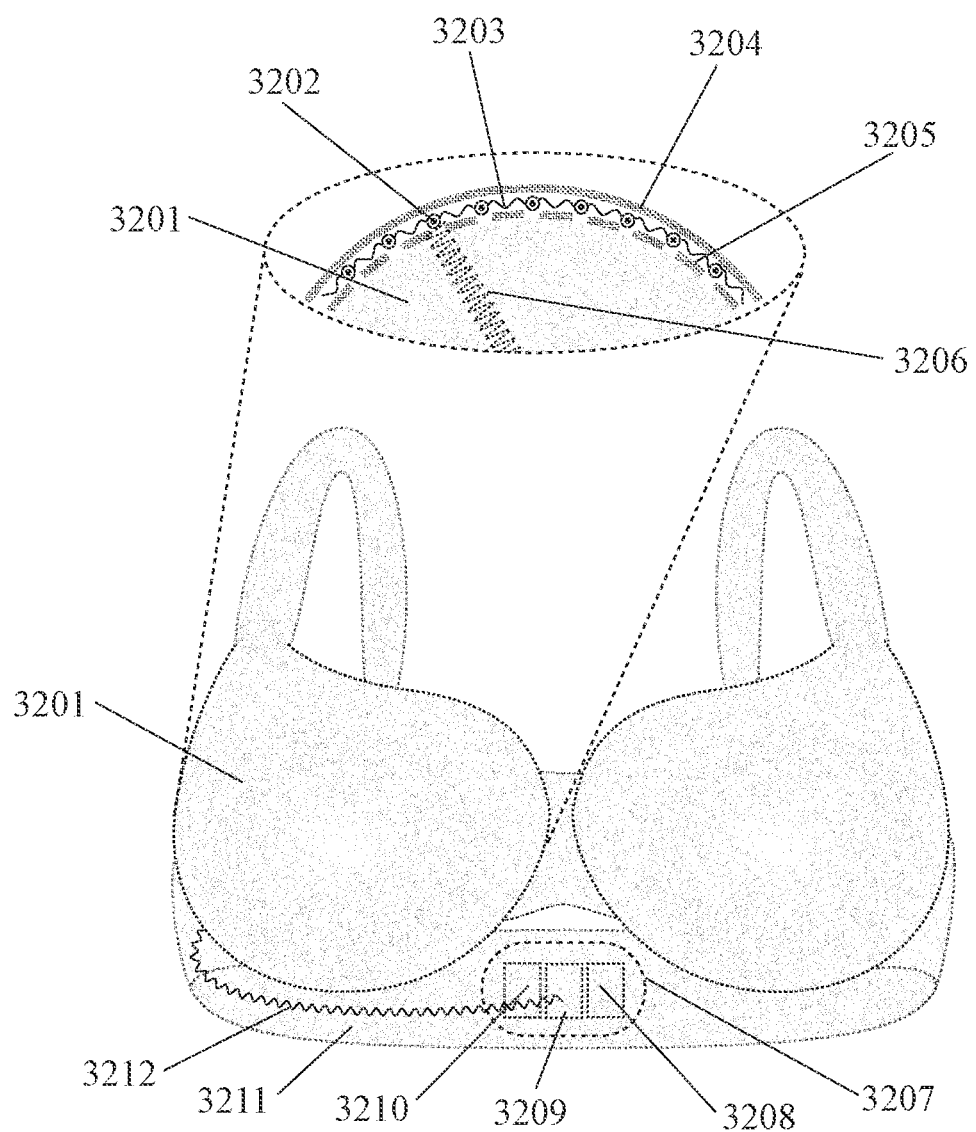
FIG. 32 shows a smart bra with a cup with an inner layer with openings, holes, or transparent sections through which light from light emitters travel to a person's body.

FIG. 32 shows an example of a smart bra for optical analysis of breast tissue comprising: a garment worn by a person, wherein the garment further comprises; a cup 3201 worn on one of the person's breasts; wherein the cup has an inner layer 3205 with openings, holes, or transparent sections through which light can travel; wherein the cup has a middle layer with electroconductive pathways (including 3203) and light emitters (including 3202); wherein the cup has an opaque outer layer 3204; and wherein light rays (including 3206) from the light emitters travel through the through the openings, holes, or transparent sections; are received by light receivers; and are analyzed to create an image of a breast and/or to identify breast tissue composition; a back strap 3211 across the person's back; an electronics housing 3207, wherein the electronics housing further comprises a battery 3210, a data processor 3209, and a data transmitter 3208; and an electromagnetic energy pathway (e.g. undulating wire or conductive thread) 3212 between one or more components in the electronics housing and the cup. In an example, a similar structure can be incorporated into a cup on the other breast.

The dotted oval in the upper portion of FIG. 32 provides a close-up cross-sectional view of a portion of cup 3201, including: an inner layer 3205 with openings, holes, or transparent sections through which light can travel; a middle layer with electroconductive pathways (including 3203) and light emitters (including 3202); and an opaque outer layer 3204.

Figure 33:
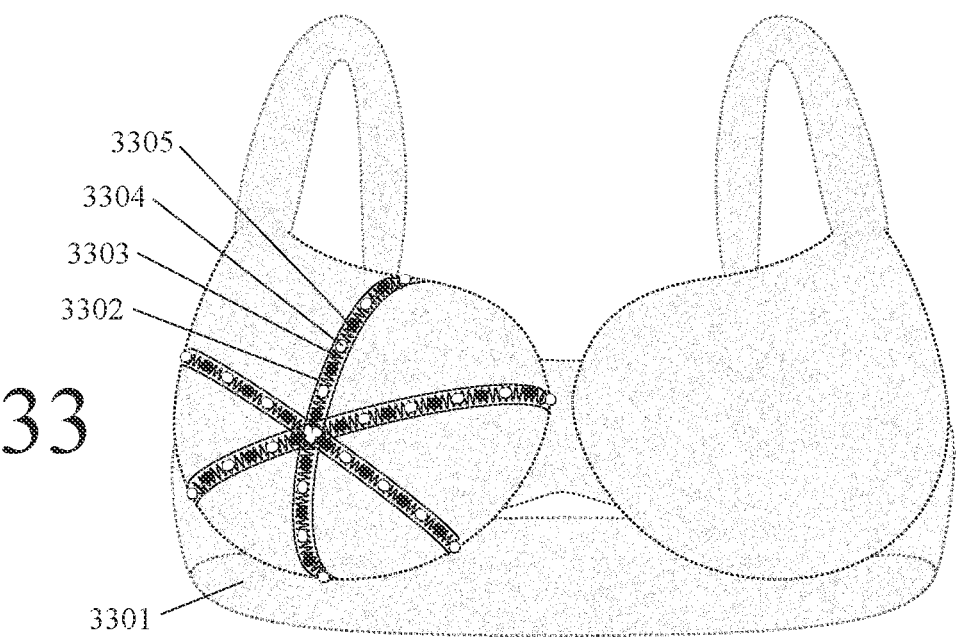
FIG. 33 shows a smart bra with: a concave hub-and-spoke array of elastic strands (or bands) with undulating wires; and light emitters and receivers connected to the wires.

FIG. 33 shows an example of a smart bra to detect abnormal breast tissue comprising: a smart bra 3301 (or other conformable wearable device) which is worn on a person's breasts; wherein the smart bra further comprises a concave hub-and-spoke array of elastic strands (or bands) 3302 containing undulating (e.g. sinusoidal) wires 3303; wherein the array further comprises a plurality of light emitters 3304 connected to the wires, wherein the light emitters transmit (near-infrared) light into breast tissue; and a plurality of light receivers 3305 connected to the wires, wherein the light receivers receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 34:
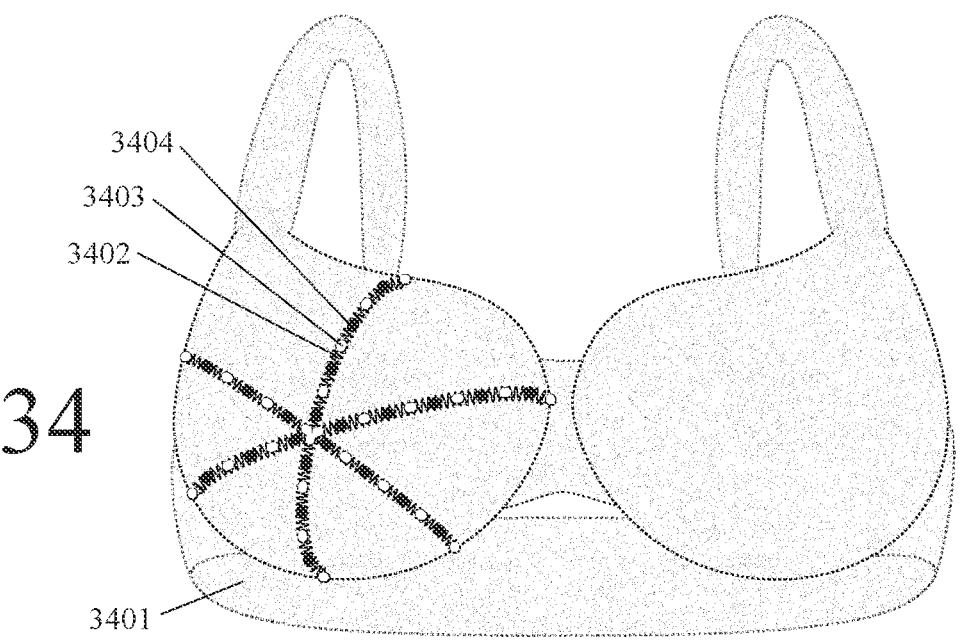
FIG. 34 shows a smart bra with: a concave hub-and-spoke array of undulating wires; and light emitters and receivers connected to the wires.

FIG. 34 shows an example of a smart bra to detect abnormal breast tissue comprising: a smart bra 3401 (or other conformable wearable device) which is worn on a person's breasts; wherein the smart bra further comprises a concave hub-and-spoke array of undulating (e.g. sinusoidal) wires 3402; a plurality of light emitters 3403 connected to the wires, wherein the light emitters which transmit (near-infrared) light into breast tissue; and a plurality of light receivers 3404 connected to the wires, wherein the light receivers receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 35:
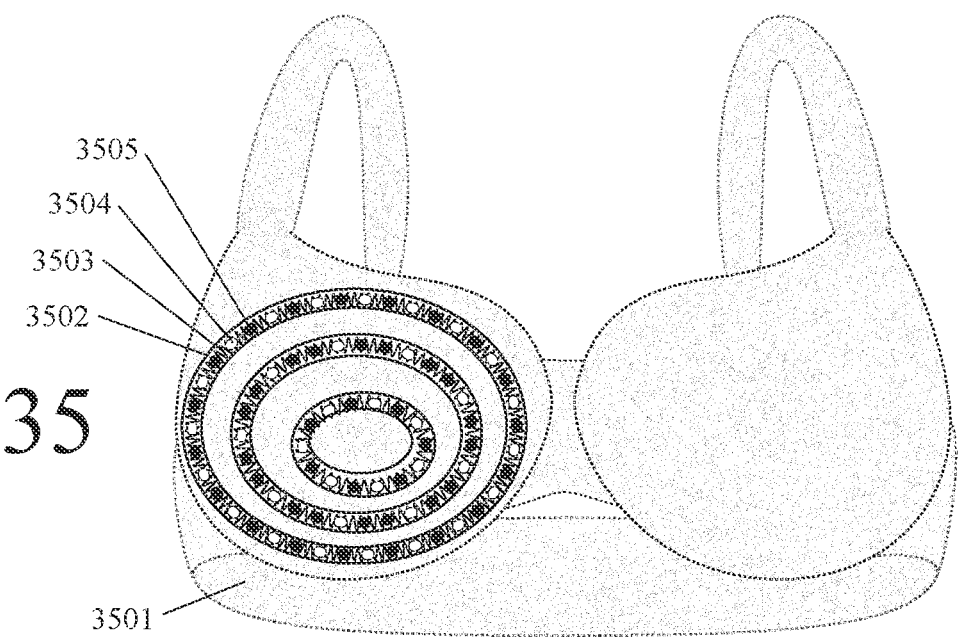
FIG. 35 shows a smart bra with: a concave nested-rings array of elastic strands (or bands) with undulating wires; and light emitters and receivers connected to the wires.

FIG. 35 shows an example of a smart bra to detect abnormal breast tissue comprising: a smart bra 3501 (or other conformable wearable device) which is worn on a person's breasts; wherein the smart bra further comprises a concave nested-rings array of elastic strands (or bands) 3502 containing undulating (e.g. sinusoidal) wires 3503; wherein the array further comprises a plurality of light emitters 3504, connected to the wires, wherein the light emitters transmit (near-infrared) light into breast tissue and a plurality of light receivers 3505, connected to the wires, wherein the light receivers receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 36:
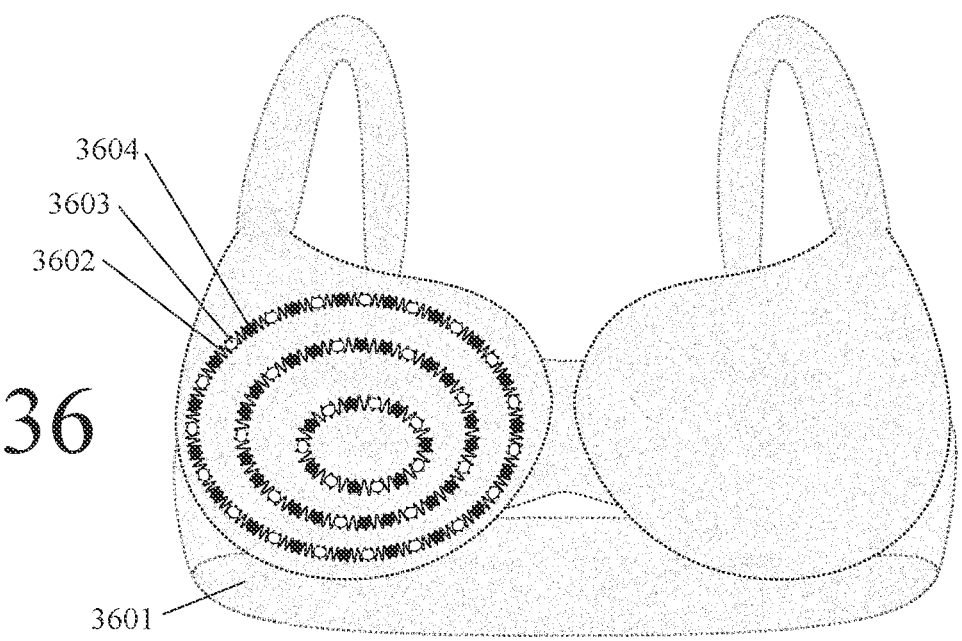
FIG. 36 shows a smart bra with: a concave nested-rings array of undulating wires; and light emitters and receivers connected to the wires.

FIG. 36 shows an example of a smart bra to detect abnormal breast tissue comprising: a smart bra 3601 (or other conformable wearable device) which is worn on a person's breasts; wherein the smart bra further comprises a concave nested-rings array of undulating (e.g. sinusoidal) wires 3602; a plurality of light emitters 3603, connected to the wires, wherein the light emitters transmit (near-infrared) light into breast tissue; and a plurality of light receivers 3604, connected to the wires, wherein the light receivers receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 37:
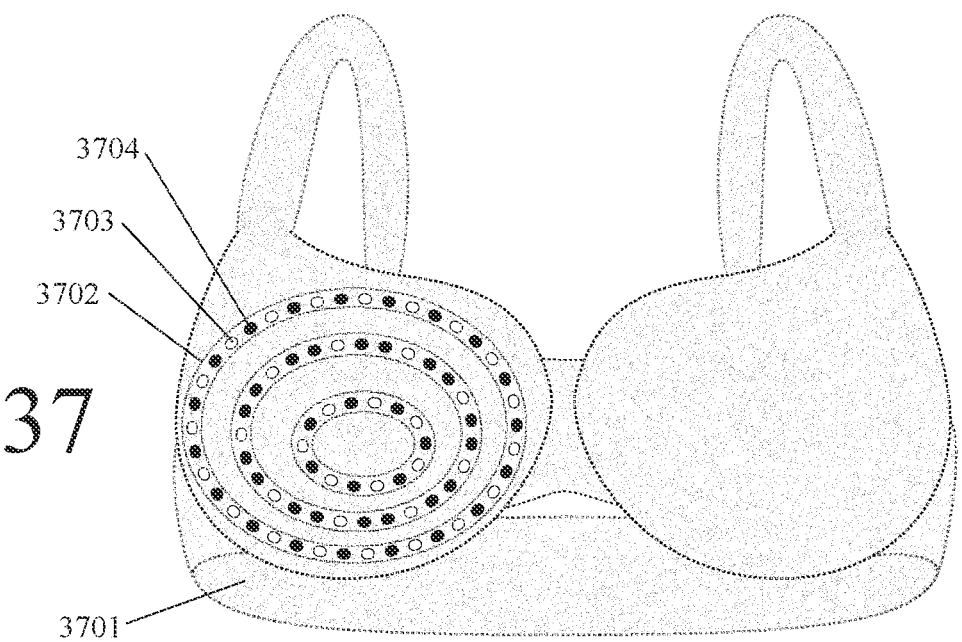
FIG. 37 shows a smart bra with a concave array of elastomeric electroconductive polymer strands; and light emitters and receivers connected to the strands.

FIG. 37 shows an example of a smart bra to detect abnormal breast tissue comprising: a smart bra 3701 (or other conformable wearable device) which is worn on a person's breasts; wherein the smart bra further comprises a concave array of strands (or bands) of elastomeric electroconductive polymer (e.g. metal-doped PDMS) 3702; wherein the array further comprises a plurality of light emitters 3703, connected to the strands, wherein the light emitters transmit (near-infrared) light into breast tissue and a plurality of light receivers 3704, connected to the strands, wherein the light receivers receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 38:
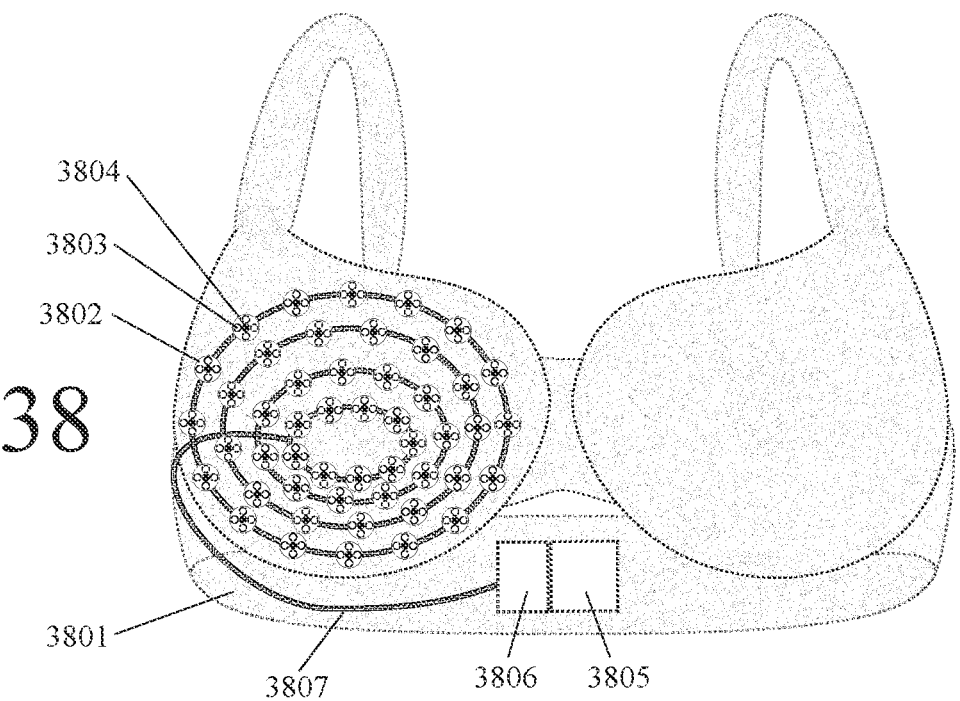
FIG. 38 shows a smart bra with a concave array of optical sensor clusters, wherein each cluster has a light emitter and a light receiver connected to a power source and a data processor by electroconductive yarns, threads, or filaments.

FIG. 38 shows an example of a smart bra to detect abnormal breast tissue comprising: a smart bra 3801 (or other conformable wearable device) which is worn on a person's breasts; wherein the smart bra further comprises a concave array of optical sensor clusters 3802; wherein each optical sensor cluster further comprises one or more light emitters 3803 which transmit (near-infrared) light into breast tissue and/or one or more light receivers 3804 which receive the light after it has passed through breast tissue, wherein changes (e.g. changes in light intensity or spectral distribution) in the light caused by passing through the breast tissue are used to identify abnormal breast tissue; a power source 3805; and a data processor 3806; wherein the smart bra further comprises elastic electroconductive yarns, threads, or filaments 3807; and wherein the optical sensor clusters are connected to the power source and to the data processor by the yarns, threads, or filaments. The same optical sensor configuration shown in the right bra cup can also be embodied in the right bra cup. Design variations discussed elsewhere in this disclosure or in priority-linked disclosures can also be applied to this example where relevant.

Figure 39:
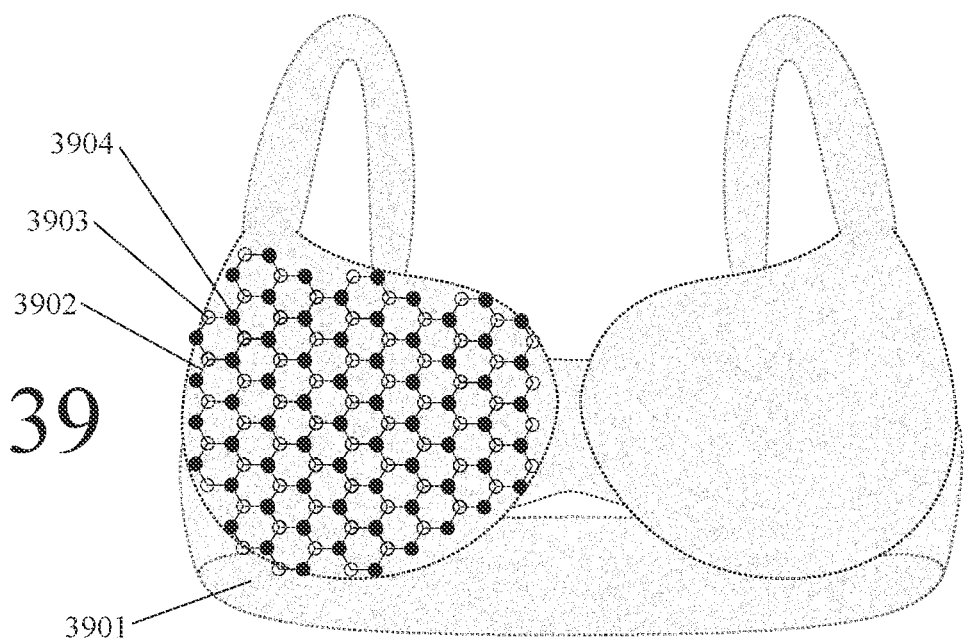
FIG. 39 shows a smart bra with a hexagonal mesh, with light emitters and receivers located at nodes in the mesh.

FIG. 39 shows an example of a smart bra to detect abnormal breast tissue comprising: a smart bra 3901 (or other conformable wearable device) which is worn on a person's breasts; wherein the smart bra further comprises a hexagonal mesh (or lattice) 3902 with a plurality of light emitters 3903 located at nodes in the hexagonal mesh (or lattice) which transmit (near-infrared) light into breast tissue and a plurality of light receivers 3904 located at nodes in the hexagonal mesh (or lattice) which receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 40:
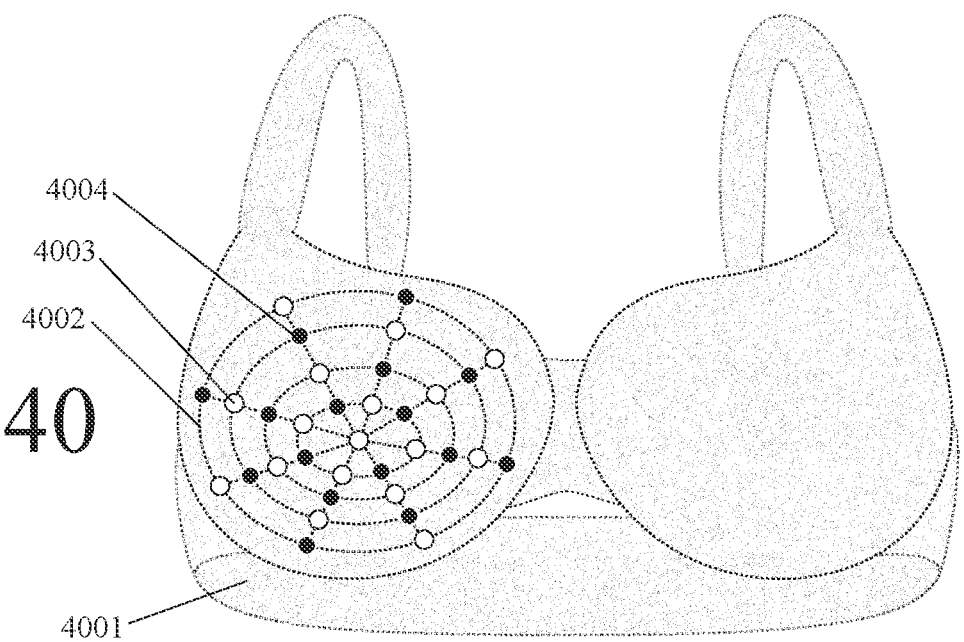
FIG. 40 shows a smart bra with a latitude-and-longitude mesh, with light emitters and receivers located at nodes in the mesh.

FIG. 40 shows an example of a smart bra to detect abnormal breast tissue comprising: a smart bra 4001 (or other conformable wearable device) which is worn on a person's breasts; wherein the smart bra further comprises a latitude-and-longitude mesh (or lattice) 4002 with a plurality of light emitters 4003 located at nodes in the latitude-and-longitude mesh (or lattice) which transmit (near-infrared) light into breast tissue and a plurality of light receivers 4004 located at nodes in the latitude-and-longitude mesh (or lattice) which receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 41:
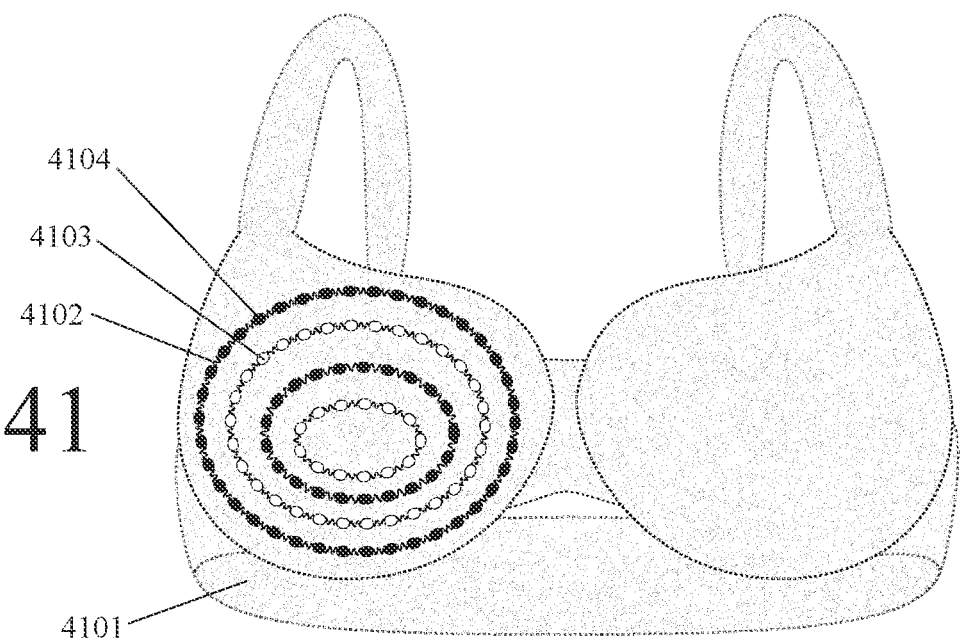
FIG. 41 shows a smart bra with a plurality of nested rings, wherein an inner-to-outer sequence of rings alternates between rings with light emitters and rings with light receivers.

FIG. 41 shows an example of a smart bra to detect abnormal breast tissue comprising: a smart bra 4101 (or other conformable wearable device) which is worn on a person's breasts; wherein the smart bra further comprises a plurality of nested rings 4102, wherein an inner-to-outer sequence of rings alternate between rings having light emitters 4103 which transmit (near-infrared) light into breast tissue and rings having light receivers 4104 which receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 42:
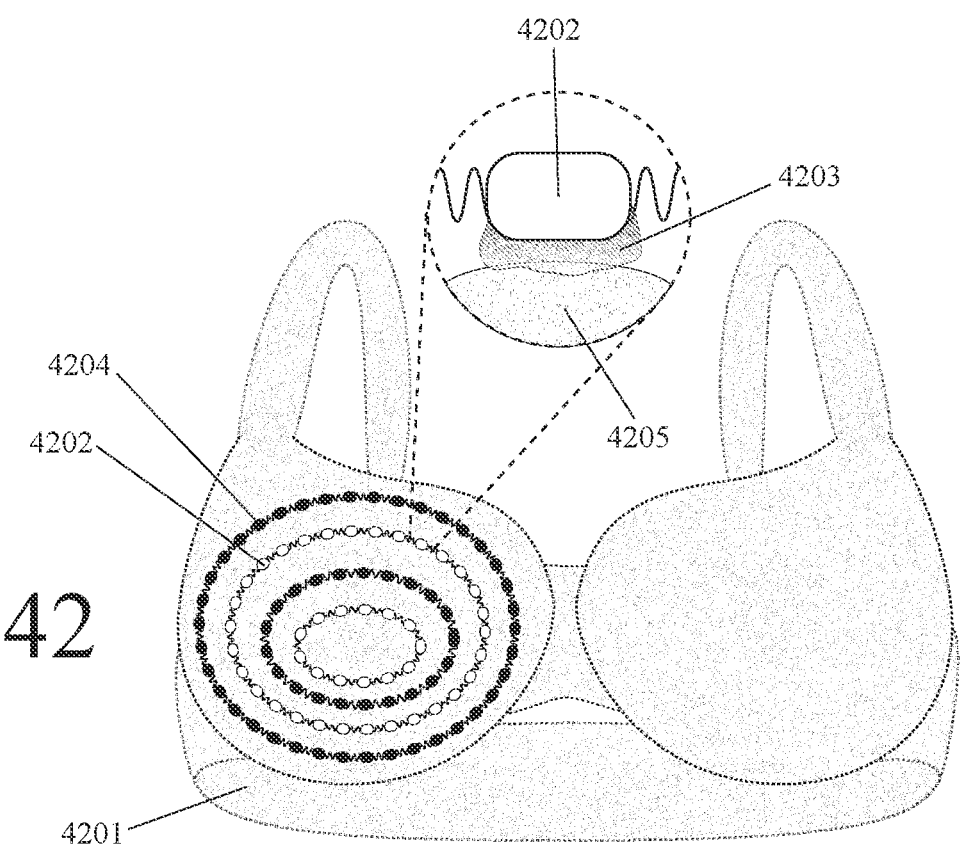
FIG. 42 shows a smart bra with light emitters, conformable transparent light guides between the light emitters and the person's body, and light receivers.

FIG. 42 shows an example of a smart bra to detect abnormal breast tissue comprising: a smart bra 4201 (or other conformable wearable device) which is worn on a person's breasts; wherein the smart bra further comprises a plurality of light emitters 4202 which transmit (near-infrared) light into breast tissue; wherein the smart bra further comprises a plurality of conformable transparent light guides 4203 between the light emitters and the person's body 4205; wherein the smart bra further comprises a plurality of light receivers 4204 which receive the light after it has passed through breast tissue; and wherein changes (e.g. changes in light intensity or spectral distribution) in the light caused by passing through the breast tissue are used to identify abnormal breast tissue. The dotted-line circle in the upper portion of FIG. 42 shows a close-up side (cross-sectional) view of a conformable transparent light guide 4203 between a light emitter 4202 and the person's body 4205. The same optical sensor configuration shown in the right bra cup can also be embodied in the right bra cup. Design variations discussed elsewhere in this disclosure or in priority-linked disclosures can also be applied to this example where relevant.

Figure 43:
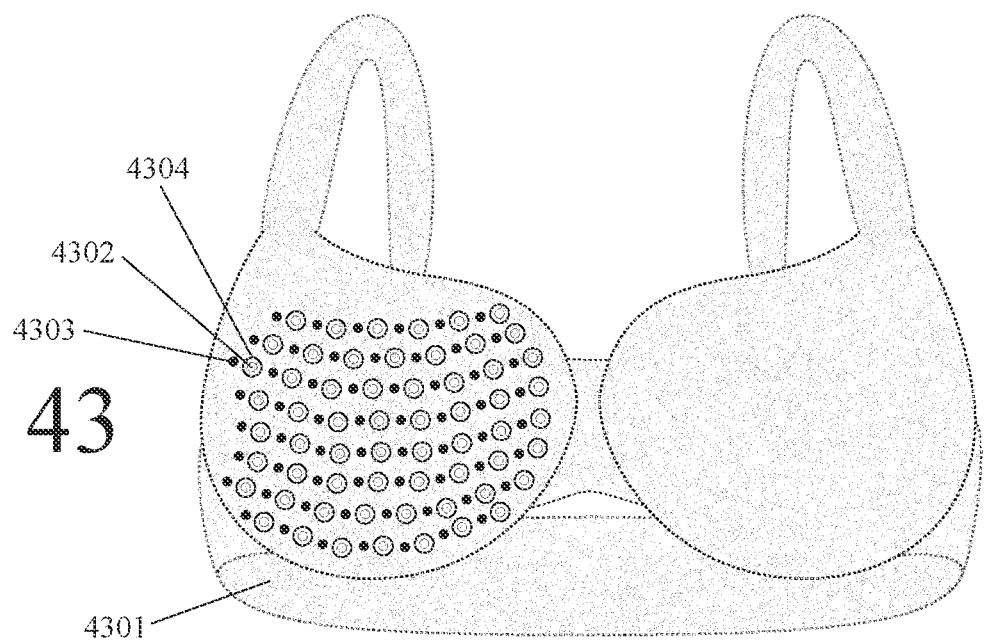
FIG. 43 shows a smart bra with light emitters, light receivers, and opaque compressible and elastomeric partitions between the light emitters and receivers.

FIG. 43 shows an example of a smart bra to detect abnormal breast tissue comprising: a smart bra 4301 (or other conformable wearable device) which is worn on a person's breasts; wherein the smart bra further comprises a plurality of light emitters 4302 which transmit (near-infrared) light into breast tissue; wherein the smart bra further comprises a plurality of light receivers 4303 which receive the light after it has passed through breast tissue; and a plurality of opaque compressible and/elastomeric partitions 4304 between light emitters and light receivers; wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 44:
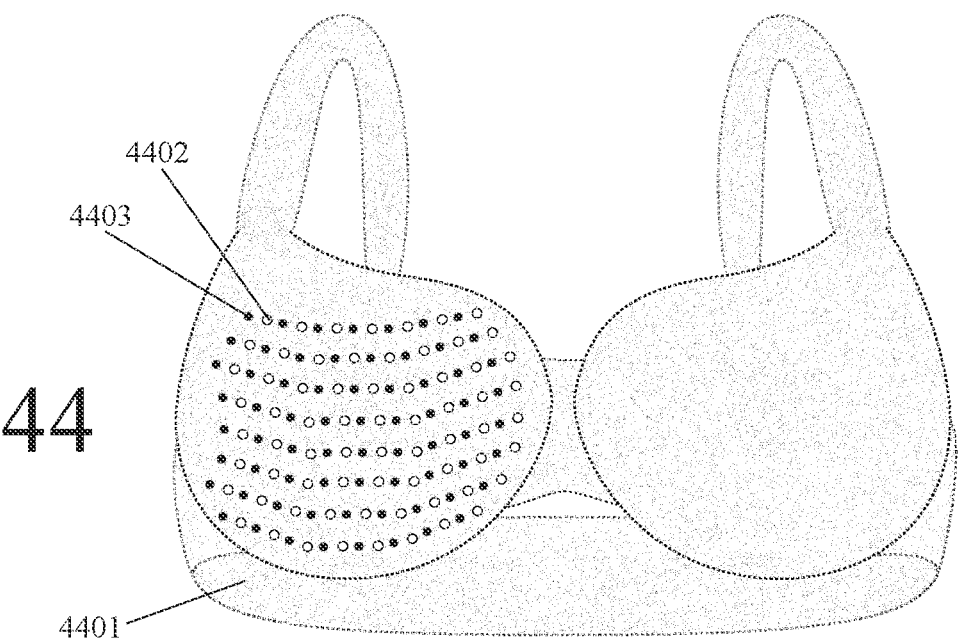
FIG. 44 shows a smart bra with light emitter and receivers distributed in an equidistant manner across the concavity of a bra cup.

FIG. 44 shows an example of a smart bra to detect abnormal breast tissue comprising: a smart bra 4401 (or other conformable wearable device) which is worn on a person's breasts; wherein the smart bra further comprises a plurality of light emitters 4402 which transmit (near-infrared) light into breast tissue, wherein light emitters are distributed in a substantially equidistant manner across the concavity of the bra cup; wherein the smart bra further comprises a plurality of light receivers 4403 which receive the light after it has passed through breast tissue; and wherein changes (e.g. changes in light intensity or spectral distribution) in the light caused by passing through the breast tissue are used to identify abnormal breast tissue. The same optical sensor configuration shown in the right bra cup can also be embodied in the right bra cup. Design variations discussed elsewhere in this disclosure or in priority-linked disclosures can also be applied to this example where relevant.

Figure 45:
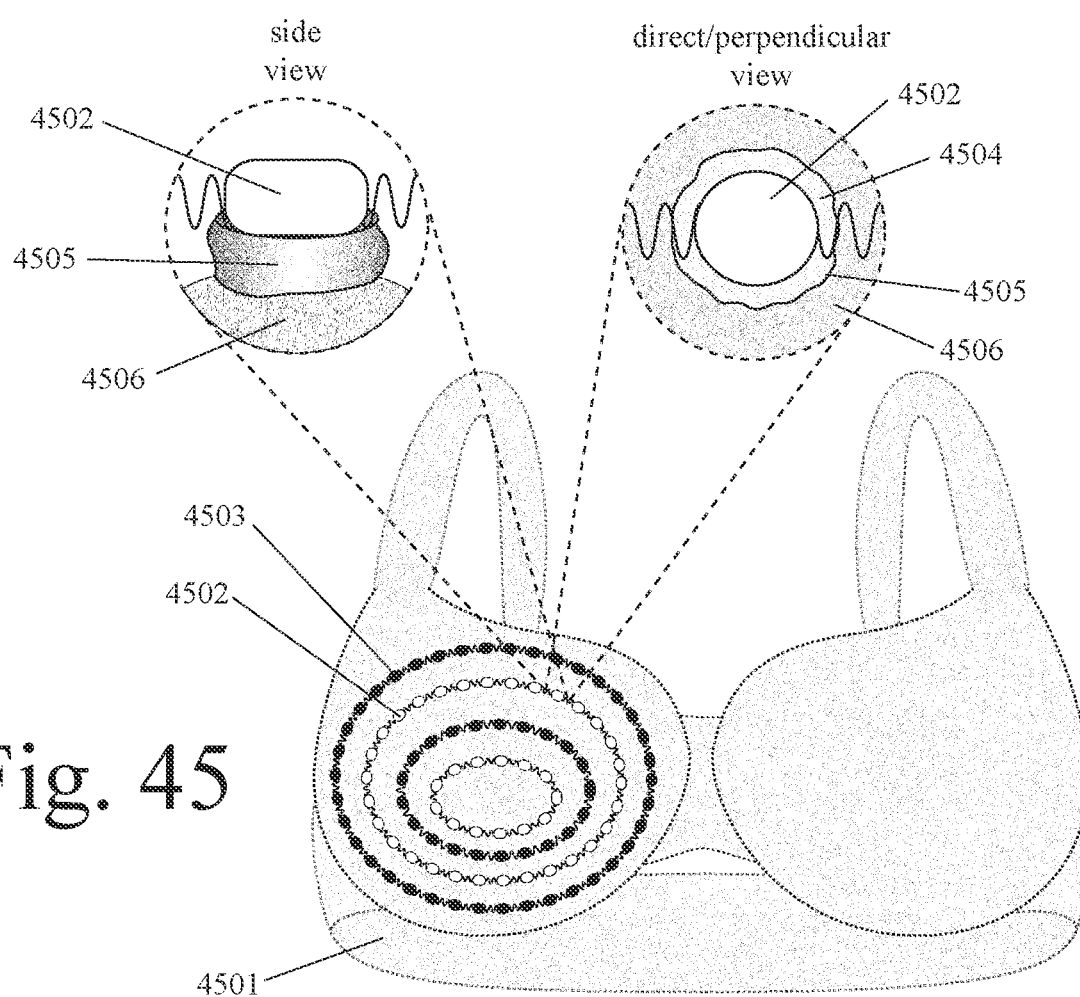
FIG. 45 shows a smart bra with light emitters, conformable light guides (with transparent cores and opaque perimeters) between the light emitters and the person's body, and light receivers.

FIG. 45 shows an example of a smart bra to detect abnormal breast tissue comprising: a smart bra 4501 (or other conformable wearable device) which is worn on a person's breasts; wherein the smart bra further comprises a plurality of light emitters 4502 which transmit (near-infrared) light into breast tissue; wherein the smart bra further comprises a plurality of light receivers 4503 which receive the light after it has passed through breast tissue; wherein the smart bra further comprises a plurality of conformable light guides with transparent central portions 4504 and opaque perimeters 4505 between the light emitters and/or the light receivers and the surface of the person's body 4506; and wherein changes (e.g. changes in light intensity or spectral distribution) in the light caused by passing through the breast tissue are used to identify abnormal breast tissue. The dotted-line circle in the upper left portion of FIG. 45 shows a close-up side (cross-sectional) view of a conformable transparent light guide with an opaque perimeter 4505 between a light emitter 4502 and the person's body 4506. The dotted-line circle in the upper right portion of FIG. 45 shows a close-up direct (perpendicular to body) view of the conformable transparent light guide with a transparent central portion 4504 and an opaque perimeter 4505 between a light emitter 4502 and the person's body 4506. The same optical sensor configuration shown in the right bra cup can also be embodied in the right bra cup. Design variations discussed elsewhere in this disclosure or in priority-linked disclosures can also be applied to this example where relevant.

In an example, a wearable device to detect abnormal breast tissue can comprise: a conformable device which is worn on a person's breasts; wherein the conformable device further comprises a plurality of light emitters which transmit (near-infrared) light into breast tissue; wherein the conformable device further comprises a plurality of light receivers which receive the light after it has passed through breast tissue; and wherein changes (e.g. changes in light intensity or spectral distribution) in the light caused by passing through the breast tissue are used to identify abnormal breast tissue. In an example, a smart bra to detect abnormal breast tissue can comprise: a smart bra (or other conformable wearable device) which is worn on a person's breasts; wherein a cup on the smart bra can be divided into eight sections by eight lines which extend out radially from the apex of the cup; wherein the smart bra further comprises at least one light emitter in each section which transmits (near-infrared) light into breast tissue; wherein the smart bra further comprises at least one light receiver in each section which receives the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises a light emitter which transmits (near-infrared) light into breast tissue and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands. In another example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmits (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises electroconductive PDMS strands; and wherein the optical sensor clusters are connected to the power source and to the data processor by the strands.

In an example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises three light emitters which transmit (near-infrared) light into breast tissue at different times and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands. Alternatively, a smart bra to detect abnormal breast tissue can comprise: a smart bra (or other conformable wearable device) which is worn on a person's breasts; wherein the smart bra further comprises a concave hub-and-spoke array of undulating (e.g. sinusoidal) wires; a plurality of light emitters connected to the wires, wherein the light emitters which transmit (near-infrared) light into breast tissue; and a plurality of light receivers connected to the wires, wherein the light receivers receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a concave matrix of light emitters which transmit (near-infrared) light into breast tissue; wherein the smart bra further comprises a concave matrix of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a first quantity of light emitters which transmit (near-infrared) light into breast tissue; wherein the smart bra further comprises a second quantity of light receivers which receive the light after it has passed through breast tissue; wherein the second quantity is greater than the first quantity; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a helical elastic strand with undulating (e.g. sinusoidal) wires, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a hexagonal mesh (or lattice) with a plurality of light emitters located at nodes in the hexagonal mesh (or lattice) which transmit (near-infrared) light into breast tissue and a plurality of light receivers located at nodes in the hexagonal mesh (or lattice) which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue and light receivers which receive the light after it has passed through breast tissue, wherein the array has 6 spokes; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue, wherein the array has 8 spokes; wherein the smart bra further comprises a hub-and-spoke array of light receivers which receive the light after it has passed through breast tissue, wherein the array has 8 spokes; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a light emitter which transmits a rotating beam of (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a nested arcuate array of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of elastic nested rings, wherein an inner-to-outer sequence of rings alternate between rings having light emitters which transmit (near-infrared) light into breast tissue and rings having light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of complementary metal-oxide-semiconductor (CMOS) image sensors which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; a power source; and a data processor; wherein the smart bra further comprises a plurality of elastic electroconductive strands (e.g. made with metal-doped elastomeric polymer) which supply the light emitters with power and which connect the light receivers to the data processor; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of opaque elastomeric polymer rings (or polygons) around the light emitters; wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create a three-dimensional image of breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create an image of breast tissue oxygenation.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 1098 and 1103 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit light in a range between 1798 and 1803 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 698 and 703 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, a third light emitter which emits light in a range between 903 and 908 nanometers, and a fourth light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 848 and 853 nanometers, a third light emitter which emits light in a range between 903 and 908 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 783 and 788 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 806 and 811 nanometers, a second light emitter which emits light in a range between 848 and 853 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 848 and 853 nanometers, a second light emitter which emits light in a range between 903 and 908 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light at a first angle and/or vector relative to the surface of the breast and a second light emitter in the plurality emits light at a second (different) angle and/or vector relative to the surface of the breast; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first polarization and a second light emitter in the plurality emits light with a second (different) polarization; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first collimation level at a first time and emits light with a second (different) collimation level at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue at angles relative to the breast surface in the range of 45 to 90 degrees; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein there are at least 50% more emitters than receivers; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the angles at which light emitters direct light into breast tissue are closer to 90 degrees for light receivers which are farther from the center of a bra cup than for light receivers which are closer to the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein light receivers are distributed in a substantially equidistant manner across the concavity of the bra cup; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters above a virtual horizontal plane through a bra cup which transmit (near-infrared) light into breast tissue; wherein the smart bra further comprises a plurality of light receivers below the horizontal plane which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein proximal pairs of light emitters are separated by 30 degrees around the circumference of a circular or elliptical ring; wherein the smart bra further comprises a plurality of light receivers which receive the light after it has passed through breast tissue, wherein proximal pairs of light receivers are separated by 30 degrees around the circumference of a circular or elliptical ring; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are less than 2 mm apart; wherein the smart bra further comprises a plurality of light receivers which receive the light after it has passed through breast tissue, wherein closest pairs of light receivers are less than 2 mm apart; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are between 5 and 10 mm apart; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the majority of these light emitters on a bra cup are located to the left of a virtual vertical plane which intersects the apex of the bra cup; wherein the smart bra further comprises a plurality of light receivers on the bra cup which receive the light after it has passed through breast tissue, wherein the majority of these light receivers are located to the right of the virtual vertical plane; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters on the perimeter of a bra cup which transmit (near-infrared) light into breast tissue; wherein the smart bra further comprises a plurality of light receivers on the concave portion of the bra cup which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein light emitters are distributed in a substantially equidistant manner across the concavity of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the average distance of light emitters from center of a bra cup is less than average distance of light receivers from the center of the bra cup; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of adjustable piezoelectric actuators which selectively compel individual light emitters and/or light receivers toward breast tissue to achieve desired pressure levels; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue;

wherein the smart bra further comprises a plurality of light receivers which receive the light after it has passed through breast tissue; wherein the smart bra further comprises a plurality of elastic and/or undulating electroconductive threads, yarns, or filaments connected to the light emitters and/or light receivers; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastomeric polymer light guides with transparent cores and opaque perimeters between the light emitters and/or the light receivers and the surface of the person's body; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent conformable light guides between the light emitters and the surface of the person's body and/or between the light receivers and the surface of the person's body; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent gel-filled micro-bladders between the light emitters and/or the light receivers and breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of undulating (e.g. sinusoidal) electroconductive threads, yarns, or filaments connected to the light emitters and/or light receivers; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises one or more electromagnetic actuators which automatically adjust the amount of pressure which the light emitters and/or the light receivers exert against breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein there is an alternating sequence of light emitters and light receivers around a circular or elliptical ring on a bra cup; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of silicon-based photodiodes and/or amorphous silicon thin-film transistors which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of transparent polydimethylsiloxane (PDMS) light guides between the light emitters and the person's body; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises between 10 and 30 light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of optical sensor clusters; wherein each cluster further comprises a first quantity of light emitters which transmit (near-infrared) light into breast tissue; wherein each cluster further comprises a second quantity of light receivers which receive the light after it has passed through breast tissue; wherein the second quantity is greater than the first quantity; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises one light emitter which transmits (near-infrared) light into breast tissue and three light receivers which receive light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of pairs of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of vertically-stacked light emitter clusters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a removable array of light emitters which transmit (near-infrared) light into breast tissue and light receivers which receive the light after it has passed through breast tissue; wherein the array can be removed before the smart bra is washed and can be reattached afterwards; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue and light receivers which receive the light after it has passed through breast tissue, wherein the array has 8 radial lines; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue and light receivers which receive the light after it has passed through breast tissue, wherein the array has 6 arms; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a strand of elastic miniature rope lighting, wherein the rope lighting further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a target-shaped array of elastic strands, wherein the array further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises an elastic strand with undulating (e.g. sinusoidal) wires, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an first array of light emitters on the upper surface of a bra cup which transmit (near-infrared) light into breast tissue; wherein the smart bra further comprises a second array of light receivers on the lower surface of the bra cup which receive the light after it has passed through breast tissue, wherein the second array is horizontally-symmetric relative to the first array; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises an undulating (e.g. sinusoidal) electroconductive strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises between 10 and 30 light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises four or more elastic nested circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises nested semi-circular arrays of light emitters on the lower surface of a bra cup which transmit (near-infrared) light into breast tissue; wherein the smart bra further comprises nested semi-circular arrays of light receivers on the upper surface of a bra cup which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises two concave arrays of light emitters which transmit (near-infrared) light into breast tissue; wherein the smart bra further comprises two concave arrays of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein a cup on the smart bra can be divided into four sections by four lines which extend out radially from the apex of the cup; wherein the smart bra further comprises at least one light emitter in each section which transmits (near-infrared) light into breast tissue; wherein the smart bra further comprises at least one light receiver in each section which receives the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a stretchable and/or flexible garment which is worn on a person's breasts; wherein the garment further comprises a plurality of light emitters which transmit (near-infrared) light into breast tissue; wherein the garment further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises four or more light emitters which transmit (near-infrared) light into breast tissue and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands. Alternatively, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmits (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastomeric polymer which has been doped with metal; and wherein the optical sensor clusters are connected to the power source and to the data processor by the strands.

In another embodiment, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises two light emitters which transmit (near-infrared) light into breast tissue and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands.

In another example, a smart bra to detect abnormal breast tissue can comprise: a smart bra (or other conformable wearable device) which is worn on a person's breasts; wherein the smart bra further comprises a concave hub-and-spoke array of elastic strands (or bands) containing undulating (e.g. sinusoidal) wires; wherein the array further comprises a plurality of light emitters connected to the wires, wherein the light emitters transmit (near-infrared) light into breast tissue; and a plurality of light receivers connected to the wires, wherein the light receivers receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a concave nested-rings array of undulating (e.g. sinusoidal) wires; a plurality of light emitters, connected to the wires, wherein the light emitters transmit (near-infrared) light into breast tissue; and a plurality of light receivers, connected to the wires, wherein the light receivers receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a first quantity of light emitters which transmit (near-infrared) light into breast tissue; wherein the smart bra further comprises a second quantity of light receivers which receive the light after it has passed through breast tissue; wherein the second quantity is less than the first quantity; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a helical elastomeric conductive polymer strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a hexagonal mesh or grid with a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue In another embodiment, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue and light receivers which receive the light after it has passed through breast tissue, wherein the array has 8 spokes; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a latitude-and-longitude array of elastic strands with undulating (e.g. sinusoidal) wires, wherein the array further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a light emitter which transmits a radially-rotating beam of (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a nested arcuate array of light emitters which transmit (near-infrared) light into breast tissue; wherein the smart bra further comprises a nested arcuate array of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of encapsulated, infrared, monochromatic, near infrared, and/or tunable LEDs which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of conformable transparent light guides between the light emitters and the person's body; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of contact sensors; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of pressure sensors which measure the amount of pressure exerted by the smart bra on the person's breasts; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create an image of breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to detect abnormal breast tissue by analyzing the levels of oxygen, hemoglobin, oxyhemoglobin, and/or deoxyhemoglobin in the breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 1208 and 1213 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 598 and 603 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit light in a range between 748 and 753 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, and a third light emitter which emits light in a range between 848 and 853 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 848 and 853 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 798 and 803 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 806 and 811 nanometers, a second light emitter which emits light in a range between 903 and 908 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 903 and 908 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first coherence level and a second light emitter in the plurality emits light with a second (different) coherence level; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first wavelength, frequency, and/or spectral distribution and a second light emitter in the plurality emits light with a second (different) wavelength, frequency, and/or spectral distribution; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first pulse duration at a first time and emits light with a second (different) pulse duration at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the angles of light transmission relative to the breast surface are changed automatically by an actuator; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein there are at least 50% more receivers than emitters; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein light receivers which are closer to the center of a bra cup are more perpendicular to the surface of a breast than light receivers which are farther from the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein emitters which are closer the center of a bra cup are farther apart than emitters which are farther from the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters below a virtual horizontal plane through a bra cup which transmit (near-infrared) light into breast tissue; wherein the smart bra further comprises a plurality of light receivers above the horizontal plane which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein proximal pairs of light emitters are separated by 60 degrees around the circumference of a circular or elliptical ring; wherein the smart bra further comprises a plurality of light receivers which receive the light after it has passed through breast tissue, wherein proximal pairs of light receivers are separated by 60 degrees around the circumference of a circular or elliptical ring; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are less than 2 mm apart; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are between 9 and 15 mm apart; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters on the right side of a bra cup which transmit (near-infrared) light into breast tissue; wherein the smart bra further comprises a plurality of light receivers on the left side of the bra cup which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters on the concave portion of a bra cup which transmit (near-infrared) light into breast tissue; wherein the smart bra further comprises a plurality of light receivers on the perimeter of the bra cup which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of adjustable springs which selectively compel individual light emitters and/or light receivers into close contact with breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of conformable light guides with transparent central portions and opaque perimeters between the light emitters and/or the light receivers and the surface of the person's body; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastic electroconductive strands (e.g. made with metal-doped elastomeric polymer) connected to the light emitters and/or light receivers; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of electroconductive threads, yarns, or filaments connected to the light emitters and/or light receivers; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent elastomeric-polymer light guides between the light emitters and the surface of the person's body and/or between the light receivers and the surface of the person's body; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent liquid-filled microbladders between the light emitters and/or the light receivers and breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a pneumatic or hydraulic mechanism which adjusts the amount of pressure which the light emitters and/or the light receivers exert against breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises one or more electromagnetic, pneumatic, or hydraulic actuators which adjust the amount of pressure which the smart bra exerts against breast tissue in order to gently compress breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of metasurface light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of stacked photodetectors, multi-layer photodetectors, and/or vertical nanowire arrays which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of transparent elastomeric polymer light guides between the light emitters and the person's body; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises between 20 and 50 light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of optical sensor clusters; wherein each cluster further comprises a first quantity of light emitters which transmit (near-infrared) light into breast tissue; wherein each cluster further comprises a second quantity of light receivers which receive the light after it has passed through breast tissue; wherein the second quantity is less than the first quantity; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises one light emitter which transmits (near-infrared) light into breast tissue and six light receivers which receive light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of pairs of light emitters which transmit (near-infrared) light into breast tissue and light receivers which receive the light after it has passed through breast tissue, wherein a light emitter and a light receiver in a pair are on opposite (right vs. left) sides of a breast cup; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a polar-coordinate array of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a removable array of light emitters which transmit (near-infrared) light into breast tissue and light receivers which receive the light after it has passed through breast tissue; wherein the array can be removed from a pocket in the smart bra before the smart bra is washed and can be reinserted into the pocket afterwards; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue, wherein the array has 12 radial lines; wherein the smart bra further comprises a starburst array of light receivers which receive the light after it has passed through breast tissue, wherein the array has 12 radial lines; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue and light receivers which receive the light after it has passed through breast tissue, wherein the array has 8 arms; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a strand of elastic miniature rope lighting (with a plurality of light emitters) which transmits (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an elastic conductive strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises an elastomeric conductive polymer strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an first array of light emitters on the lower surface of a bra cup which transmit (near-infrared) light into breast tissue; wherein the smart bra further comprises a second array of light receivers on the upper surface of the bra cup which receive the light after it has passed through breast tissue, wherein the second array is horizontally-symmetric relative to the first array; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises at least one light emitter which transmits (near-infrared) light into breast tissue; wherein the smart bra further comprises a helical and/or spiral array of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises between 20 and 50 light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises more than 50 light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises nested semi-circular arrays of light emitters on the left side of a bra cup which transmit (near-infrared) light into breast tissue; wherein the smart bra further comprises nested semi-circular arrays of light receivers on the right side of a bra cup which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises two conic section arrays of light emitters which transmit (near-infrared) light into breast tissue; wherein the smart bra further comprises two conic section arrays of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein a cup on the smart bra can be divided into quadrants by four lines extending radially from the apex of the cup; wherein the smart bra further comprises at least one light emitter in each quadrant which transmits (near-infrared) light into breast tissue; wherein the smart bra further comprises at least one light receiver in each quadrant which receives the light after it has passed through breast tissue; and wherein changes (e.g. changes in light intensity or spectral distribution) in the light caused by passing through the breast tissue are used to identify abnormal breast tissue. In another example, a wearable device to detect abnormal breast tissue can comprise: a garment which is worn on a person's breasts; wherein the garment further comprises a plurality of light emitters which transmit (near-infrared) light into breast tissue; wherein the garment further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises four or more light emitters which transmit (near-infrared) light into breast tissue at different times and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands.

Alternatively, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmit (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises elastic electroconductive yarns, threads, or filaments; and wherein the optical sensor clusters are connected to the power source and to the data processor by the yarns, threads, or filaments.

In another embodiment, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises two light emitters which transmit (near-infrared) light into breast tissue at different times and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands. In another example, a smart bra to detect abnormal breast tissue can comprise: a smart bra (or other conformable wearable device) which is worn on a person's breasts; wherein the smart bra further comprises a concave hub-and-spoke array of strands of elastomeric electroconductive polymer (e.g. metal-doped PDMS); wherein the array further comprises a plurality of light emitters connected to the strands which transmit (near-infrared) light into breast tissue and a plurality of light receivers connected to the strands which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a concave nested-rings array of elastic strands (or bands) containing undulating (e.g. sinusoidal) wires; wherein the array further comprises a plurality of light emitters, connected to the wires, wherein the light emitters transmit (near-infrared) light into breast tissue and a plurality of light receivers, connected to the wires, wherein the light receivers receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a helical and/or spiral array of light emitters which transmit (near-infrared) light into breast and light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a helical elastomeric conductive polymer strand with a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a hexagonal mesh or grid with a plurality of light emitters on mesh or grid nodes which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a hub-and-spoke array of elastic strands with undulating (e.g. sinusoidal) wires, wherein the array further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a latitude-and-longitude mesh (or lattice) with a plurality of light emitters located at nodes in the latitude-and-longitude mesh (or lattice) which transmit (near-infrared) light into breast tissue and a plurality of light receivers located at nodes in the latitude-and-longitude mesh (or lattice) which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a light emitter which transmits a revolving beam of (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a parabolic array of light emitters which transmit (near-infrared) light into breast tissue; wherein the smart bra further comprises a parabolic array of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of lasers which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of conformable transparent light guides between the light emitters and the person's body; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of opaque compressible and/or elastomeric partitions between light emitters and light receivers; wherein changes (e.g. changes in light intensity or spectral distribution) in the light caused by passing through the breast tissue are used to identify abnormal breast tissue.

In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a power source; wherein the smart bra further comprises a plurality of elastic electroconductive strands (e.g. made with metal-doped elastomeric polymer) which connect the light emitters to the power source; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create an image of breast tissue density. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to detect abnormal breast tissue by analyzing increased or disorganized vasculature in the breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 1398 and 1403 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit light in a range between 658 and 663 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, a third light emitter which emits light in a range between 848 and 853 nanometers, a fourth light emitter which emits light in a range between 903 and 908 nanometers, and a fifth light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, and a third light emitter which emits light in a range between 903 and 908 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 903 and 908 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit light in a range between 806 and 811 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit light in a range between 825 and 830 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 916 and 921 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first collimation level and a second light emitter in the plurality emits light with a second (different) collimation level; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first amplitude and/or intensity at a first time and emits light with a second (different) amplitude and/or intensity at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first polarization t a first time and emits light with a second (different) polarization at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the angles of light transmission relative to the breast surface are changed automatically by moving micromirrors and/or electromagnetic actuators; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein receivers which are closer to the center of a bra cup are closer together than receivers which are farther from the center of the bra cup; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein light receivers which are farther from the center of a bra cup are more perpendicular to the surface of a breast than light receivers which are closer to the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters on a first side (e.g. the right side) of a bra cup which transmit (near-infrared) light into breast tissue; wherein the smart bra further comprises a plurality of light receivers on the opposite side (e.g. the left side) of the bra cup which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the light emitters are separated by equal radial degrees around the circumference of a circular or elliptical ring; wherein the smart bra further comprises a plurality of light receivers which receive the light after it has passed through breast tissue, wherein the light receivers are separated by equal radial degrees around the circumference of a circular or elliptical ring; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein proximal pairs of light emitters are separated by 60 degrees around the circumference of a circular or elliptical ring; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein closest pairs of light receivers are less than 2 mm apart; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the majority of these light emitters are located above a virtual horizontal plane which intersects the apex of a bra cup; wherein the smart bra further comprises a plurality of light receivers which receive the light after it has passed through breast tissue, wherein the majority of these light receivers are located below the virtual horizontal plane; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters on the left side of a bra cup which transmit (near-infrared) light into breast tissue; wherein the smart bra further comprises a plurality of light receivers on the right side of the bra cup which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light of varying wavelengths over time into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein changes (e.g. changes in light intensity or spectral distribution) in the light caused by passing through the breast tissue are used to identify abnormal breast tissue; a power source; and a plurality of electroconductive polydimethylsiloxane (PDMS) connections between a power source and the light emitters.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of adjustable springs which selectively compel individual light emitters and/or light receivers toward breast tissue at a desired pressure level; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of conformable light guides with transparent central portions and opaque perimeters between the light emitters and/or the light receivers and the surface of the person's body; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastic electroconductive strands (e.g. made with metal-doped polydimethylsiloxane) connected to the light emitters and/or light receivers; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light different wavelengths into breast tissue; wherein the smart bra further comprises a plurality of light receivers which receive the light after it has passed through breast tissue; wherein the smart bra further comprises a plurality of electroconductive threads, yarns, or filaments connected to the light emitters and/or light receivers; and wherein changes (e.g. changes in light intensity or spectral distribution) in the light at different wavelengths caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent polydimethylsiloxane (PDMS) light guides between the light emitters and the surface of the person's body and/or between the light receivers and the surface of the person's body; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent air-filled micro-bladders between the light emitters and/or the light receivers and breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a pneumatic or hydraulic mechanism which automatically adjusts the amount of pressure which the light emitters and/or the light receivers exert against breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises one or more electromagnetic, piezoelectric, pneumatic, hydraulic mechanisms which adjust the amount of pressure which the smart bra exerts against breast tissue in order to obtain close contact between the light emitters and/or light receivers and breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of multi-layer photodetectors which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of stacked photodetectors which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of vertical nanowire arrays which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises more than 50 light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises a plurality of light emitters which transmit (near-infrared) light into breast tissue and a plurality of light receivers which receive light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises six light emitters which transmit (near-infrared) light into breast tissue and one light receiver which receives light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of pairs of light emitters which transmit (near-infrared) light into breast tissue and light receivers which receive the light after it has passed through breast tissue, wherein a light emitter and a light receiver in a pair are on opposite (upper vs. lower) surfaces of a breast cup; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a quadrilateral mesh (or lattice) with a plurality of light emitters located at nodes in the quadrilateral mesh (or lattice) which transmit (near-infrared) light into breast tissue and a plurality of light receivers located at nodes in the quadrilateral mesh (or lattice) which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a rows-and-columns array of light emitters which transmit (near-infrared) light into breast tissue; wherein the smart bra further comprises a rows-and-columns array of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue, wherein the array has 6 radial lines; wherein the smart bra further comprises a starburst array of light receivers which receive the light after it has passed through breast tissue, wherein the array has 6 radial lines; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue, wherein the array has 12 arms; wherein the smart bra further comprises a star-shaped array of light receivers which receive the light after it has passed through breast tissue, wherein the array has 12 arms; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a strand of electroconductive polydimethylsiloxane (PDMS), wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an elastic conductive strand with a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises an elastomeric conductive polymer strand with a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an oval or elliptical array of light emitters which transmit (near-infrared) light into breast tissue; wherein the smart bra further comprises an oval or elliptical array of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises at least one semicircular array of light emitters which transmit (near-infrared) light into breast tissue; wherein the smart bra further comprises at least one semicircular array of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises elastic concentric rings with (sinusoidal) undulations; wherein each ring has light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises nested semi-circular arrays of light emitters which transmit (near-infrared) light into breast tissue; wherein the smart bra further comprises nested semi-circular arrays of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises three elastic circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein a cup on the smart bra can be divided into six hextants by six lines extending radially away from the apex of the cup; wherein the smart bra further comprises at least one light emitter in each hextant which transmits (near-infrared) light into breast tissue; wherein the smart bra further comprises at least one light receiver in each hextant which receives the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a concave array of elastic strands containing undulating (e.g. sinusoidal) wires; wherein the array further comprises a plurality of light emitters connected to the wires which transmit (near-infrared) light into breast tissue and a plurality of light receivers connected to the wires which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmits (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises undulating (e.g. sinusoidal) wires; and wherein the optical sensor clusters are connected to the power source and to the data processor by the wires.

In an example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmits (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises elastic electroconductive yarns, threads, or filaments; and wherein the optical sensor clusters are connected to the power source and to the data processor by the yarns, threads, or filaments.

In another example, a smart bra to detect abnormal breast tissue can comprise: a smart bra (or other conformable wearable device) which is worn on a person's breasts; wherein the smart bra further comprises a concave array of strands (or bands) of elastomeric electroconductive polymer (e.g. metal-doped PDMS); wherein the array further comprises a plurality of light emitters, connected to the strands, wherein the light emitters transmit (near-infrared) light into breast tissue and a plurality of light receivers, connected to the strands, wherein the light receivers receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a concave hub-and-spoke array of elastic strands containing undulating (e.g. sinusoidal) wires; wherein the array further comprises a plurality of light emitters connected to the wires which transmit (near-infrared) light into breast tissue and a plurality of light receivers connected to the wires which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a first quantity of light emitters which transmit (near-infrared) light into breast tissue; wherein the smart bra further comprises a second quantity of light receivers which receive the light after it has passed through breast tissue; wherein the ratio of the first quantity to the second quantity is between 2 and 5; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a helical and/or spiral array of light emitters which transmit (near-infrared) light into breast tissue; wherein the smart bra further comprises a helical and/or spiral array of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a hemispherical array of light emitters which transmit (near-infrared) light into breast tissue; wherein the smart bra further comprises a hemispherical array of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a hexagonal mesh or grid with a plurality of light emitters which transmit (near-infrared) light into breast tissue and a plurality of light receivers on mesh or grid nodes which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue, wherein the array has 12 spokes; wherein the smart bra further comprises a hub-and-spoke array of light receivers which receive the light after it has passed through breast tissue, wherein the array has 12 spokes; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a latitude-and-longitude mesh (or lattice) with a plurality of light emitters located at nodes in the latitude-and-longitude mesh (or lattice) which transmit (near-infrared) light into breast tissue and a plurality of light receivers located at nodes in the latitude-and-longitude mesh (or lattice) which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a miniature rope lighting strand with a plurality of light emitters which transmits (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of continuous wave, diode, dye, multi-wavelength, sapphire, and/or super-luminescent lasers which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of avalanche photo diodes (APDs), PIN photodiodes, photodetectors, and/or other photodetectors which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; a power source; a data processor; and a wireless data transmitter; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of opaque compressible and/elastomeric partitions between light emitters and light receivers; wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a wireless data transmitter and receiver; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create an image of breast tissue composition.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to detect abnormal breast tissue by analyzing the levels of adipose tissue, collagen, and/or lipids in the breast tissue. In another example, a smart bra to detect abnormal breast tissue can comprise: a smart bra (or other conformable wearable device) which is worn on a person's breasts; wherein the smart bra further comprises a plurality of light emitters which transmit light in a range between 1501 and 1506 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 668 and 673 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, a third light emitter which emits light in a range between 848 and 853 nanometers, and a fourth light emitter which emits light in a range between 903 and 908 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, and a third light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 763 and 768 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 806 and 811 nanometers, a second light emitter which emits light in a range between 848 and 853 nanometers, a third light emitter which emits light in a range between 903 and 908 nanometers, and a fourth light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit light in a range between 828 and 833 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 978 and 983 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first pulse duration and a second light emitter in the plurality emits light with a second (different) pulse duration; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light at a first angle and/or vector relative to the surface of the breast at a first time and emits light at a second (different) angle and/or vector relative to the surface of the breast at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first wavelength, frequency, and/or spectral distribution at a first time and emits light with a second (different) wavelength, frequency, and/or spectral distribution at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the light emitters are arranged in a first set of arcs; wherein the smart bra further comprises a plurality of light receivers which receive the light after it has passed through breast tissue, wherein the light receivers are arranged in a second set of arcs, and wherein the first set of arcs and the second set of arcs are symmetric with respect to a horizontal plane through a bra cup; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the angles at which light emitters direct light into breast tissue are different for light receivers which are closer to the center of a bra cup than for light receivers which are farther from the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein receivers which are closer the center of a bra cup are farther apart than receivers which are farther from the center of the bra cup; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters on first portion (e.g. an upper portion) of a bra cup which transmit (near-infrared) light into breast tissue; wherein the smart bra further comprises a plurality of light receivers on the opposite portion (e.g. a lower portion) which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein proximal light emitters are separated by equal distances around the circumference of a circular or elliptical ring; wherein the smart bra further comprises a plurality of light receivers which receive the light after it has passed through breast tissue, wherein proximal light receivers are separated by equal distances around the circumference of a circular or elliptical ring; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue, wherein proximal pairs of light receivers are separated by 60 degrees around the circumference of a circular or elliptical ring; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are between 10 and 20 mm apart; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the majority of these light emitters are located below a virtual horizontal plane which intersects the apex of a bra cup; wherein the smart bra further comprises a plurality of light receivers which receive the light after it has passed through breast tissue, wherein the majority of these light receivers are located above the virtual horizontal plane; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters along an upper perimeter of a bra cup which transmit (near-infrared) light into breast tissue; wherein the smart bra further comprises a plurality of light receivers along a lower perimeter of the bra cup which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light of time-varying wavelengths within a selected range into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein changes (e.g. changes in light intensity or spectral distribution) in the light caused by passing through the breast tissue are used to identify abnormal breast tissue; a power source; and a plurality of electroconductive elastomeric polymer connections between a power source and the light emitters. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of adjustable electromagnetic actuators which selectively compel individual light emitters and/or light receivers toward breast tissue to achieve desired pressure levels; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of conformable light guides with transparent central portions and opaque perimeters between the light emitters and/or the light receivers and the surface of the person's body; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastomeric cushions which push the light emitters and/or the light receivers into close contact with breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of low-durometer (e.g. durometer less than 50) light guides with transparent cores and opaque perimeters between the light emitters and/or the light receivers and the surface of the person's body; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent low-durometer (e.g. durometer less than 20) light guides between the light emitters and the surface of the person's body and/or between the light receivers and the surface of the person's body; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of undulating (e.g. sinusoidal) electroconductive wires connected to the light emitters and/or light receivers; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a pneumatic or hydraulic mechanism which selectively adjusts the amounts of pressure which individual light emitters and/or individual light receivers exert against breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein there are at least twice as many light emitters as light receivers; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of phased-array or other spectrophotometers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of three-dimensionally-stacked light receiver clusters which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of vertically-stacked light receiver clusters which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of metasurface light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises at least one light emitter which transmits (near-infrared) light into breast tissue and at least one light receiver which receives light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises three light emitters which transmit (near-infrared) light into breast tissue and one light receiver which receives light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of semicircular arrays of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a quadrilateral mesh or lattice with light emitters which transmit (near-infrared) light into breast tissue and light receivers which receive the light after it has passed through breast tissue; wherein the light emitters and light receivers are located at nodes (or intersections) in the mesh or lattice; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue and light receivers which receive the light after it has passed through breast tissue, wherein the array has 12 radial lines; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue, wherein the array has 8 radial lines; wherein the smart bra further comprises a starburst array of light receivers which receive the light after it has passed through breast tissue, wherein the array has 8 radial lines; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue, wherein the array has 6 arms; wherein the smart bra further comprises a star-shaped array of light receivers which receive the light after it has passed through breast tissue, wherein the array has 6 arms; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a strand of electroconductive polydimethylsiloxane (PDMS) with a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises an elastic helical and/or spiral array of light emitters which transmit (near-infrared) light into breast and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an first array of light emitters on the right side of a bra cup which transmit (near-infrared) light into breast tissue; wherein the smart bra further comprises a second array of light receivers on the left side of the bra cup which receive the light after it has passed through breast tissue, wherein the second array is vertically-symmetric relative to the first array; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises an undulating (and/or sinusoidal) and centrally-helical array of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises at least ten sensor clusters; wherein each cluster further comprises a first quantity of light emitters which transmit (near-infrared) light into breast tissue; wherein each cluster further comprises a second quantity of light receivers which receive the light after it has passed through breast tissue; wherein the second quantity is greater than the first quantity; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises four or more elastic circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises nested semi-circular arrays of light emitters on the right side of a bra cup which transmit (near-infrared) light into breast tissue; wherein the smart bra further comprises nested semi-circular arrays of light receivers on the left side of a bra cup which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises three elastic concentric circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein a cup on the smart bra can be divided into six sections by six lines which extend out radially from the apex of the cup; wherein the smart bra further comprises at least one light emitter in each section which transmits (near-infrared) light into breast tissue; wherein the smart bra further comprises at least one light receiver in each section which receives the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises a light emitter which transmits (near-infrared) light into breast tissue or a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands.

In another embodiment, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises one or more light emitters which transmits (near-infrared) light into breast tissue and/or one or more light receivers which receive the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises electroconductive polymer strands; and wherein the optical sensor clusters are connected to the power source and to the data processor by the strands. Alternatively, a smart bra to detect abnormal breast tissue can comprise: a smart bra (or other conformable wearable device) which is worn on a person's breasts; wherein the smart bra further comprises a concave array of optical sensor clusters; wherein each optical sensor cluster further comprises three light emitters which transmit (near-infrared) light into breast tissue and a light receiver which receives the light after it has passed through breast tissue, wherein changes (e.g. changes in light intensity or spectral distribution) in the light caused by passing through the breast tissue are used to identify abnormal breast tissue; a power source; and a data processor; wherein the smart bra further comprises strands of elastic and/or undulating electroconductive strands; and wherein the optical sensor clusters are connected to the power source and to the data processor by the strands.

In an example, a smart bra to detect abnormal breast tissue can comprise: a smart bra (or other conformable wearable device) which is worn on a person's breasts; wherein the smart bra further comprises a concave array of strands of elastomeric electroconductive polymer (e.g. metal-doped PDMS); wherein the array further comprises a plurality of light emitters connected to the strands which transmit (near-infrared) light into breast tissue and a plurality of light receivers connected to the strands which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a concave matrix of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a first quantity of light emitters which transmit (near-infrared) light into breast tissue; wherein the smart bra further comprises a second quantity of light receivers which receive the light after it has passed through breast tissue; wherein the ratio of the second quantity to the first quantity is between 2 and 5; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a helical and/or spiral array of light emitters which transmit (near-infrared) light into breast tissue; wherein the smart bra further comprises at least one light receiver which receives the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a hexagonal mesh (or lattice) with a plurality of light emitters located at nodes in the hexagonal mesh (or lattice) which transmit (near-infrared) light into breast tissue and a plurality of light receivers located at nodes in the hexagonal mesh (or lattice) which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue and light receivers which receive the light after it has passed through breast tissue, wherein the array has 12 spokes; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a hub-and-spoke array of light emitters which transmit (near-infrared) light into breast tissue, wherein the array has 6 spokes; wherein the smart bra further comprises a hub-and-spoke array of light receivers which receive the light after it has passed through breast tissue, wherein the array has 6 spokes; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a latitude-and-longitude array of light emitters which transmit (near-infrared) light into breast tissue; wherein the smart bra further comprises a latitude-and-longitude array of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a miniature rope-lighting strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of elastic nested rings, wherein each ring has an alternating series of light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of charge-coupled device (CCDs) and/or detector arrays which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; a power source; and a plurality of elastic electroconductive connections between the power source and the light emitters; wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and a plurality of opaque elastomeric polymer (e.g. polydimethylsiloxane) partitions between the light emitters and the light receivers; wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and pressure sensors which measure the level of pressure and/or degree of contact between the light emitters and the person's body; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to create an image of breast tissue vasculature. Alternatively, a smart bra to detect abnormal breast tissue can comprise: a smart bra (or other conformable wearable device) which is worn on a person's breasts; wherein the smart bra further comprises a plurality of Light Emitting Diodes (LEDs) which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit light in a range between 1698 and 1703 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit light in a range between 688 and 693 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 806 and 811 nanometers, a third light emitter which emits light in a range between 848 and 853 nanometers, and a fourth light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 748 and 753 nanometers, a second light emitter which emits light in a range between 848 and 853 nanometers, a third light emitter which emits light in a range between 903 and 908 nanometers, and a fourth light emitter which emits light in a range between 978 and 983 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit light in a range between 778 and 783 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the plurality further comprises a first light emitter which emits light in a range between 806 and 811 nanometers, a second light emitter which emits light in a range between 848 and 853 nanometers, and a third light emitter which emits light in a range between 903 and 908 nanometers; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit light in a range between 848 and 853 nanometers into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light with a first amplitude and/or intensity and a second light emitter in the plurality emits light with a second (different) amplitude and/or intensity; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a first light emitter in the plurality emits light at a first time and a second light emitter in the plurality emits light at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein a light emitter in the plurality emits light with a first coherence level at a first time and emits light with a second (different) coherence level at a second time; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue at angles relative to the breast surface in the range of 85 to 95 degrees; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the light emitters are arranged in a first set of arcs; wherein the smart bra further comprises a plurality of light receivers which receive the light after it has passed through breast tissue, wherein the light receivers are arranged in a second set of arcs, and wherein the first set of arcs and the second set of arcs are symmetric with respect to a vertical plane through a bra cup; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the angles at which light emitters direct light into breast tissue are closer to 90 degrees for light receivers which are closer to the center of a bra cup than for light receivers which are farther from the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein emitters which are closer to the center of a bra cup are closer together than emitters which are farther from the center of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters on a first side (e.g. the right side) of a virtual vertical plane through a bra cup which transmit (near-infrared) light into breast tissue; wherein the smart bra further comprises a plurality of light receivers on the opposite side (e.g. the left side) of the vertical plane which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein proximal pairs of light emitters are separated by 120 degrees around the circumference of a circular or elliptical ring; wherein the smart bra further comprises a plurality of light receivers which receive the light after it has passed through breast tissue, wherein proximal pairs of light receivers are separated by 120 degrees around the circumference of a circular or elliptical ring; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters configured in circular or elliptical rings which transmit (near-infrared) light into breast tissue, wherein light emitters on inner circular or elliptical rings are closer together than light emitters on outer circular or elliptical rings; wherein the smart bra further comprises a plurality of light receivers configured in circular or elliptical rings which receive the light after it has passed through breast tissue, wherein light receivers on inner circular or elliptical rings are closer together than light receivers on outer circular or elliptical rings; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein closest pairs of light emitters are between 1 and 3 mm apart; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein the majority of these light emitters on a bra cup are located to the right of a virtual vertical plane which intersects the apex of the bra cup; wherein the smart bra further comprises a plurality of light receivers on the bra cup which receive the light after it has passed through breast tissue, wherein the majority of these light receivers are located to the left of the virtual vertical plane; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters along a lower perimeter of a bra cup which transmit (near-infrared) light into breast tissue; wherein the smart bra further comprises a plurality of light receivers along an upper perimeter of the bra cup which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue, wherein light emitters are distributed in a substantially equidistant manner across the concavity of the bra cup; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the average distance of light emitters from center of a bra cup is greater than average distance of light receivers from the center of the bra cup; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of adjustable pneumatic or hydraulic actuators which selectively compel individual light emitters and/or light receivers toward breast tissue to achieve desired pressure levels; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastic and/or stretchable electroconductive threads, yarns, or filaments connected to the light emitters and/or light receivers; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of elastomeric polymer light guides with transparent cores and opaque circumferences between the light emitters and/or the light receivers and the surface of the person's body; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of springs which compel the light emitters and/or the light receivers into close contact with breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts;

wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of transparent low-durometer (e.g. durometer less than 50) light guides between the light emitters and the surface of the person's body and/or between the light receivers and the surface of the person's body; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises a plurality of undulating (e.g. sinusoidal) electroconductive strands connected to the light emitters and/or light receivers; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein the smart bra further comprises one or more electromagnetic actuators which adjust the amount of pressure which the light emitters and/or the light receivers exert against breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of light receivers which receive the light after it has passed through breast tissue; wherein there are at least twice as many light receivers as light emitters; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of photomultiplier tubes which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises a plurality of transparent liquid microbladders between the light emitters and the person's body; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of light emitters which transmit (near-infrared) light into breast tissue; wherein the smart bra further comprises an undulating (and/or sinusoidal) and centrally-helical array of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of nested rings, wherein an inner-to-outer sequence of rings alternate between rings having light emitters which transmit (near-infrared) light into breast tissue and rings having light receivers which receive the light after it has passed through breast tissue; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises one light emitter which transmits (near-infrared) light into breast tissue and two light receivers which receive light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a plurality of optical sensor clusters; wherein the majority of sensor clusters each further comprises two light emitters which transmit (near-infrared) light into breast tissue and one light receiver which receives light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a plurality of three-dimensionally-stacked light emitter clusters which transmit (near-infrared) light into breast tissue; wherein the smart bra further comprises a plurality of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises a radial-spoke array of elastic strands with undulating (e.g. sinusoidal) wires, wherein the array further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises a starburst array of light emitters which transmit (near-infrared) light into breast tissue and light receivers which receive the light after it has passed through breast tissue, wherein the array has 6 radial lines; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue and light receivers which receive the light after it has passed through breast tissue, wherein the array has 12 arms; and wherein changes (e.g. changes in light intensity or spectral distribution) in the light caused by passing through the breast tissue are used to identify abnormal breast tissue.

In another embodiment, a smart bra to detect abnormal breast tissue can comprise: a smart bra (or other conformable wearable device) which is worn on a person's breasts; wherein the smart bra further comprises a star-shaped array of light emitters which transmit (near-infrared) light into breast tissue, wherein the array has 8 arms; wherein the smart bra further comprises a star-shaped array of light receivers which receive the light after it has passed through breast tissue, wherein the array has 8 arms; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises a strand of polydimethylsiloxane (PDMS) which has been doped with metal particles, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an elastic helical and/or spiral array of light emitters which transmit (near-infrared) light into breast tissue; wherein the smart bra further comprises a helical and/or spiral array of light receivers which receive the light after it has passed through breast tissue; and wherein changes (e.g. changes in light intensity or spectral distribution) in the light caused by passing through the breast tissue are used to identify abnormal breast tissue. In another example, a smart bra to detect abnormal breast tissue can comprise: a smart bra (or other conformable wearable device) which is worn on a person's breasts; wherein the smart bra further comprises an first array of light emitters on the left side of a bra cup which transmit (near-infrared) light into breast tissue; wherein the smart bra further comprises a second array of light receivers on the right side of the bra cup which receive the light after it has passed through breast tissue, wherein the second array is vertically-symmetric relative to the first array; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises an undulating (e.g. sinusoidal) elastic electroconductive-polymer (e.g. polydimethylsiloxane (PDMS) impregnated with metal particles) strand, wherein the strand further comprises a plurality of light emitters which transmit (near-infrared) light into breast tissue and a plurality of light receivers which receive the light after it has passed through breast tissue; and wherein changes (e.g. changes in light intensity or spectral distribution) in the light caused by passing through the breast tissue are used to identify abnormal breast tissue. Alternatively, a smart bra to detect abnormal breast tissue can comprise: a smart bra (or other conformable wearable device) which is worn on a person's breasts; wherein the smart bra further comprises at least ten sensor clusters; wherein each cluster further comprises a first quantity of light emitters which transmit (near-infrared) light into breast tissue; wherein each cluster further comprises a second quantity of light receivers which receive the light after it has passed through breast tissue; wherein the second quantity is less than the first quantity; and wherein changes (e.g. changes in light intensity or spectral distribution) in the light caused by passing through the breast tissue are used to identify abnormal breast tissue.

In an example, a smart bra to detect abnormal breast tissue can comprise: a smart bra (or other conformable wearable device) which is worn on a person's breasts; wherein the smart bra further comprises four or more elastic concentric circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In another example, a smart bra to detect abnormal breast tissue can comprise: a smart bra (or other conformable wearable device) which is worn on a person's breasts; wherein the smart bra further comprises nested semi-circular arrays of light emitters on the upper surface of a bra cup which transmit (near-infrared) light into breast tissue; wherein the smart bra further comprises nested semi-circular arrays of light receivers on the lower surface of a bra cup which receive the light after it has passed through breast tissue; and wherein changes (e.g. changes in light intensity or spectral distribution) in the light caused by passing through the breast tissue are used to identify abnormal breast tissue.

Alternatively, a smart bra to detect abnormal breast tissue can comprise: a smart bra (or other conformable wearable device) which is worn on a person's breasts; wherein the smart bra further comprises three elastic nested circular or elliptical rings with light emitters which transmit (near-infrared) light into breast tissue and light receivers which receive the light after it has passed through breast tissue; and wherein changes (e.g. changes in light intensity or spectral distribution) in the light caused by passing through the breast tissue are used to identify abnormal breast tissue.

In an example, a smart bra to detect abnormal breast tissue can comprise: a smart bra which is configured to be worn on a person's breasts; wherein the smart bra further comprises a concave hub-and-spoke array of undulating wires; wherein the smart bra further comprises a plurality of light emitters connected to the wires and wherein the light emitters transmit light into breast tissue; and wherein the smart bra further comprises a plurality of light receivers connected to the wires and wherein the light receivers receive the light after it has passed through breast tissue; and wherein changes in the light caused by passing through the breast tissue are used to identify abnormal breast tissue.

In an example, a smart bra to detect abnormal breast tissue can comprise: a smart bra which is configured to be worn on a person's breasts; wherein the smart bra further comprises a concave array of optical sensor clusters; wherein an optical sensor cluster further comprises one or more light emitters which transmit light into breast tissue and/or one or more light receivers which receive the light after it has passed through breast tissue; wherein changes in the light caused by passing through the breast tissue are used to identify abnormal breast tissue; wherein the smart bra further comprises a power source; and wherein the smart bra further comprises a data processor; wherein the smart bra further comprises elastic electroconductive yarns, threads, or filaments; and wherein the optical sensor clusters are connected to the power source and/or to the data processor by the yarns, threads, or filaments.

In an example, a smart bra to detect abnormal breast tissue can comprise: a smart bra which is configured to be worn on a person's breasts; wherein the smart bra further comprises a plurality of light emitters which transmit light into breast tissue; wherein the smart bra further comprises a plurality of conformable transparent light guides which are configured to be between the light emitters and the person's body; wherein the smart bra further comprises a plurality of light receivers which receive the light after it has passed through breast tissue; and wherein changes in the light caused by passing through the breast tissue are used to identify abnormal breast tissue.

I claim:

1. A smart bra to detect abnormal breast tissue comprising:
    a smart bra which is configured to be worn on a person's breasts;
    wherein the smart bra further comprises a concave hub-and-spoke array of sinusoidal wires, wherein central ends of different spokes in the array are different distances from a center of the array;
    wherein the smart bra further comprises a plurality of light emitters connected to the wires and wherein the light emitters are configured to transmit light into breast tissue; and
    wherein the smart bra further comprises a plurality of light receivers connected to the wires and wherein the light receivers are configured to receive the light after it has passed through breast tissue.

2. A smart bra to detect abnormal breast tissue comprising:
    a smart bra which is configured to be worn on a person's breasts;
    wherein the smart bra further comprises a concave array of optical sensor clusters;
    wherein a cluster in the concave array of optical sensor clusters further comprises a first quantity of light emitters which are configured to transmit near-infrared light into breast tissue and a second quantity of light receivers which are configured to receive the light after it has passed through breast tissue, wherein the second quantity is less than the first quantity;
    wherein each cluster further comprises a first quantity of light emitters which are configured to transmit near-infrared light into breast tissue, wherein each cluster further comprises a second quantity of light receivers which are configured to receive the light after it has passed through breast tissue, and wherein the second quantity is less than the first quantity;
    wherein the smart bra further comprises a power source; and
    wherein the smart bra further comprises a data processor;
    wherein the smart bra further comprises elastic electroconductive yarns, threads, or filaments; and
    wherein the optical sensor clusters are connected to the power source and/or to the data processor by the yarns, threads, or filaments.

3. A smart bra to detect abnormal breast tissue comprising:
    a smart bra which is configured to be worn on a person's breasts;
    wherein the smart bra further comprises a plurality of light emitters which are configured to transmit light into breast tissue;
    wherein the smart bra further comprises a plurality of light receivers which are configured to receive the light after it has passed through breast tissue; and
    wherein the smart bra further comprises a plurality of transparent light guides with a durometer level less than 50 which are configured to be between the light emitters and the surface of the person's body and/or between the light receivers and the surface of the person's body.

* * * * *